US009376481B2

(12) United States Patent
Gonias et al.

(10) Patent No.: US 9,376,481 B2
(45) Date of Patent: Jun. 28, 2016

(54) METHODS OF PROMOTING CNS NEURONAL REPAIR BY INHIBITING LRP-1

(75) Inventors: Steven L. Gonias, San Diego, CA (US); Travis Stiles, La Jolla, CA (US); Alban Gaultier, Charlottesville, VA (US); Wendy M. Campana, La Jolla, CA (US); Katerina Akassoglou, San Francisco, CA (US)

(73) Assignees: The Regents of the University of California, Oakland, CA (US); J. David Gladsone Institutes, San Francisco, CA (US)

( * ) Notice: Subject to any disclaimer, the term of this patent is extended or adjusted under 35 U.S.C. 154(b) by 0 days.

(21) Appl. No.: 14/113,626

(22) PCT Filed: Apr. 26, 2012

(86) PCT No.: PCT/US2012/035125

§ 371 (c)(1), (2), (4) Date: Feb. 18, 2014

(87) PCT Pub. No.: WO2012/149111

PCT Pub. Date: Nov. 1, 2012

(65) Prior Publication Data

US 2014/0161807 A1 Jun. 12, 2014

Related U.S. Application Data

(60) Provisional application No. 61/479,210, filed on Apr. 26, 2011.

(51) Int. Cl.

| | |
|---|---|
| ***C07K 14/705*** | (2006.01) |
| ***A61K 38/17*** | (2006.01) |
| ***A61K 38/18*** | (2006.01) |
| ***A61K 45/06*** | (2006.01) |
| ***C07K 16/28*** | (2006.01) |
| ***C12N 15/113*** | (2010.01) |
| ***C12N 15/86*** | (2006.01) |

(52) U.S. Cl.

CPC ............ *C07K 14/705* (2013.01); *A61K 38/177* (2013.01); *A61K 38/18* (2013.01); *A61K 45/06* (2013.01); *C07K 16/28* (2013.01); *C12N 15/1138* (2013.01); *C12N 15/86* (2013.01)

(58) Field of Classification Search

None

See application file for complete search history.

(56) References Cited

FOREIGN PATENT DOCUMENTS

| | | | |
|---|---|---|---|
| RU | 2173151 | C2 | 10/2001 |
| WO | 9714437 | A1 | 4/1997 |
| WO | 2007/044325 | A2 | 4/2007 |

OTHER PUBLICATIONS

Lillis et al., LDL Receptor-Related Protein 1: Unique Tissue-Specific Functions Revealed by Selective Gene Knockout Studies, 2008, Physiol. Rev. 88: 887-918.*

Polavarapu et al., Tissue-type plasminogen activator—mediated shedding of astrocytic low-density lipoprotein receptor—related protein increases the permeability of the neurovascular unit, Apr. 15, 2007, Blood 109(8):3270-3278.*

PCT/US2012/035125 International Search Report mailed on Sep. 27, 2012.

Gaultier et al. "Low-density lipoprotein receptor-related protein 1 is an essential receptor for myelin phagocytosis." J. Cell Science, 2009, 122(8):1155-1162.

Martin et al. "The Functional Role of the Second NPXY Motif of the LRP1 β-Chain in Tissue-type Plasminogen Activator-mediated Activation of N-Methyl-D-aspartate Receptors." The Journal of Biological Chemistry, 2008, 283 (18):12004-12013.

Caroni and Schwab. "Antibody Against Myelin-Associated Inhibitor of Neurite Growth Neutralizes Nonpermissive Substrate Properties of CNS White Matter," Mar. 1988, Neuron, vol. 1, 85-96.

Gozenbach et al. "Delayed Anti-Nogo-A Antibody Application after Spinal Cord Injury Shows Progressive Loss of Responsiveness," Journal of Neurotrauma, Feb. 2012, 29:567-578.

Bregman et al. "Recovery from Spinal Cord Injury Mediated by Antibodies to Neurite Growth Inhibitors," Nov. 1995, Nature, vol. 378, 498-501.

Liebscher et al. "Nogo-A Antibody Improves Regeneration and Locomotion of Spinal Cord-Injured Rats," 2005, Ann Neurol, 58:706-719.

Sengottuvel et al. "Taxol Facilitates Axon Regeneration in the Mature CNS," Feb. 2011, J. Neurosci., 31 (7):2688-2699.

Ruschel et al. "Systemic Administration of Epothilone B Promotes Axon Regeneration After Spinal Cord Injury," 2015, Sciencexpress Reports, 10.1126:1-8.

Winton et al. "Characterization of New Cell Permeable C3-like Proteins That Inactivate Rho and Stimulate Neurite Outgrowth on Inhibitory Substrates," 2002, Journal of Biological Chemistry, vol. 277, No. 36; 32820-32829.

Boato et al. "C3 Peptide Enhances Recovery from Spinal Cord Injury by Improved Regenerative Growth of Descending Fiber Tracts," 2010, Journal of Cell Science, 123(10), 1652-1662.

Fehlings et al. "A Phase I/IIa Clinical Trial of a Recombinant Rho Protein Antagonist in Acute Spinal Cord Injury," May 2011, Journal of Neurotrauma, 28:787-796.

* cited by examiner

*Primary Examiner* — John Ulm

(74) *Attorney, Agent, or Firm* — Wagenknecht IP Law Group PC

(57) ABSTRACT

This invention provides methods for promoting and/or restoring neurite outgrowth and neuronal regeneration by contacting an injured neuron with an inhibitor of low density lipoprotein receptor-related protein-1 (LRP-1).

16 Claims, 11 Drawing Sheets

MIFLATLPLFWIMISASRGGHWGAWMPSTISAFEGTCVSIPCRFDFPDELRPAVVH
GVWYFNSPYPKNYPPVVFKSRTQVVHESFQGRSRLLGDLGLRNCTLLLSTLSPEL
GGKYYFRGDLGGYNQYTFSEHSVLDIVNTPNIVVPPEVVAGTEVEVSCMVPDNC
PELRPELSWLGHEGLGEPTVLGRLREDEGTWVQVSLLHFVPTREANGHRLGCQA
AFPNTTLQFEGYASLDVKYPPVIVEMNSSVEAIEGSHVSLLCGADSNPPPLLTWM
RDGMVLREAVAKSLYLDLEEVTPGEDGVYACLAENAYGQDNRTVELSVMYAP
WKPTVNGTVVAVEGETVSILCSTQSNPDPILTIFKEKQILATVIYESQLQLELPAVT
PEDDGEYWCVAENQYGQRATAFNLSVEFAPIILLESHCAAARDTVQCLCVVKSN
PEPSVAFELPSRNVTVNETEREFVYSERSGLLLTSILTIRGQAQAPPRVICTSRNLY
GTQSLELPFQGAHRLMWAKIGPVGAVVAFAILIAIVCYITQTRRKKNVTESSSFSG
GDNPHVLYSPEFRISGAPDKYESEKRLGSERRLLGLRGESPELDLSYSHSDLGKRP
TKDSYTLTEELAEYAEIRVK

*Fig. 2*

METHODS OF PROMOTING CNS NEURONAL REPAIR BY INHIBITING LRP-1

CROSS-REFERENCE TO RELATED APPLICATIONS

This application is a 35 U.S.C. §371 National Stage of International Application No. PCT/US2012/035125, filed Apr. 26, 2012, and claims the benefit under 25 U.S.C. §119(e) of U.S. Ser. No. 61/479,210, filed on Apr. 26, 2011, the content of each of which is hereby incorporated herein by reference in their entirety for all purposes.

STATEMENT OF GOVERNMENTAL SUPPORT

This invention was made with government support under Grant Nos. R01 NS057456, R01 NS054571, awarded by the National Institutes of Health (NIH), National Institute of Neurological Disorders and Stroke (NINDS). The United States government has certain rights in the invention.

SEQUENCE LISTING

The instant application contains a Sequence Listing which has been submitted electronically in ASCII format and is hereby incorporated by reference in its entirety. Said ASCII copy, created on Jan. 23, 2014, is named CA206392_SL.txt and is 85,365 bytes in size.

FIELD OF THE INVENTION

The present invention relates to reducing or inhibiting the function and/or signaling through the low density lipoprotein receptor-related protein-1 (LRP-1) to promote, enhance and/or restore neuron regeneration and/or nerve growth in the presence of injury to the CNS, e.g., to counteract CNS damage resulting from spinal cord injury or traumatic brain injury.

BACKGROUND OF THE INVENTION

Recovery from CNS injury is limited by macromolecules that accumulate in the micro-environment of damaged neurons and inhibit axonal regeneration (Berry (1982). *Bibliotheca anatomica*, 1-11; Ng, et al., (1996). *Brain Res* 720:17-24; Yiu and He, (2006). Nat Rev Neurosci 7: 617-627). In the acute phase of CNS injury, myelin-derived proteins are principally responsible for regenerative failure. The inhibitory proteins include myelin-associated glycoprotein (MAG) (Tang, et al., (1997). *Mol Cell Neurosci* 9:333-346), oligodendrocyte myelin glycoprotein (OMgp) (Wang, et al., (2002). *Nature* 417:941-944), and Nogo (Fournier, (2001) *Nature* 409:341-346; Filbin, (2003). *Nat Rev Neurosci* 4:703-713). Later in the course of CNS injury, chondroitin sulfate proteoglycans (CSPGs) in the glial scar inhibit axonal regeneration (Oohira, et al., (1991). *J Neurosci* 11:822-827.; Hynds and Snow, (1999). *Experimental Neurology* 160:244-255). MAG, OMgp, and Nogo bind to the neuronal receptors, Nogo-66 receptor (NgR1) (Fournier et al., 2001, supra) and paired immunoglobulin-like receptor B (PirB) (Atwal et al., (2008). *Science* 322:967-970.). MAG also binds gangliosides which might play a role in inhibition (Vyas, et al., *Proc Natl Acad Sci USA*. 2002 Jun. 11; 99(12): 8412-7). Co-receptors, including p75NTR (Wong et al., (2002). *Nat Neurosci* 5:1302-1308), Nogo-66 receptor 1 (NgR1) and LINGO1 (Mi et al., (2004). *Nat Neurosci* 7:221-228), are recruited into the Nogo receptor complex and neuronal signaling to RhoA is initiated (Yamashita et al., (2002). *J Cell Biol* 157:565-570). In certain instances, TAJ/TROY binds to NgR1 and can replace p75NTR in the p75NTR/NgR1/LINGO-1 complex to activate RhoA in the presence of myelin inhibitors (Shao, et al., *Neuron* (2005) 45(3):353-9). Activated RhoA causes growth cone collapse and inhibits neurite outgrowth (Kozma et al., (1997). *Mol Cell Biol* 17:1201-1211; Kuhn et al., (1999). *J Neurosci* 19:1965-1975; Madura et al., (2004). *EMBO Reports* 5:412-417).

Low density lipoprotein receptor-related protein-1 (LRP1) is a type-1 transmembrane receptor that binds over forty structurally and functionally distinct ligands, mediating their endocytosis and delivery to lysosomes (Strickland et al., (2002). *Trends Endocrinol Metab* 13:66-74). LRP1 also functions in phagocytosis of large particles, including myelin vesicles (Lillis et al., (2008). *J Immunol* 181:364-373; Gaultier et al., (2009). *J Cell Sci* 122: 1155-1162). Neurons in the CNS and PNS express LRP1 (Wolf et al., (1992). *Am J Pathol* 141, 37-42; Bu et al., (1994). *J Biol Chem* 269:18521-18528; Campana et al., (2006). *J Neurosci* 26: 11197-11207). At the subcellular level, LRP1 has been localized in dendritic shafts and spines, consistent with its known ability to interact with post-synaptic density proteins and regulate long-term potentiation (Brown et al., (1997). *Brain Res* 747:313-317.; May et al., (2004). *Mol Cell Biol* 24:8872-8883) and in neuronal growth cones, both in intercellular vesicles and at the cell surface (Steuble et al., (2010). *Proteomics* 10:3775-3788).

In neurons and neuron-like cell lines, binding and endocytosis of specific LRP1 ligands is coupled with activation of cell-signaling (Qiu et al., (2004). *J Biol Chem* 279:34948-34956; Hayashi et al., (2007). *J Neurosci* 27:1933-1941; Fuentealba et al., (2009). *J Biol Chem* 284:34045-34053; Mantuano, et al., (2008). *J Neurosci* 28:11571-11582; Shi et al., (2009). *Sci Signal* 2:ra18). Src family kinases (SFKs), which are activated downstream of LRP1, transactivate Trk receptors, accounting mechanistically for the ability of LRP1 ligands to induce neurite outgrowth (Shi et al., 2009, supra). However, LRP1 also regulates cell-signaling by serving as a co-receptor or by regulating the trafficking of other receptors, such as uPAR, TNFR1, and PDGF receptor (Webb et al., (2001). *J Cell Biol* 152:741-752; Boucher et al., (2003). *Science* 300:329-332; Gaultier et al., (2008). Blood 111: 5316-5325). The function of LRP1 in conjunction with other cell-signaling receptors explains the activity of LRP1 in regulation of inflammation, atherogenesis, and cell growth.

Our previous work demonstrating myelin phagocytosis by LRP1 (Gaultier et al., (2009). *J Cell Sci* 122: 1155-1162) prompted us to examine the role of LRP1 in pathways by which myelin-associated proteins inhibit axonal regeneration. We demonstrate that LRP1 is an endocytic receptor for myelin-associated inhibitory proteins, including e.g., MAG, OMgp, and Nogo isoforms. Binding of MAG to LRP1 recruits p75NTR into complex with LRP1. Both p75NTR and LRP1 are required for RhoA activation and inhibition of neurite outgrowth. Multiple strategies for inactivating LRP1 were effective at reversing the effects of MAG and purified myelin on neurite outgrowth. Our results suggest that LRP1 is essential for inhibitory myelin signaling. LRP1 emerges as a possible target for neutralizing inhibitory myelin-associated inhibitory proteins in the injured CNS.

SUMMARY OF THE INVENTION

In one aspect, the invention provides methods for increasing, promoting, restoring or enhancing nerve growth and/or neuronal regeneration, comprising contacting a neuron with an inhibitor or antagonist of low density lipoprotein receptor-related protein-1 (LRP-1) in the presence of a myelin-associated inhibitor protein (a.k.a, myelin-associated inhibitory factor (MAIF)).

In another aspect, the invention provides methods for increasing, promoting, restoring or enhancing nerve growth and/or neuronal regeneration in a subject in need thereof, comprising administering to the subject an effective amount of an inhibitor or antagonist of low density lipoprotein receptor-related protein-1 (LRP-1).

In a further aspect, the invention provides methods for inhibiting CNS myelin-mediated neurite outgrowth inhibition and/or for promoting or restoring axonal regeneration. In some embodiments, the methods comprise contacting a neuron with a LRP-1 inhibitor or antagonist, wherein the LRP-1 inhibitor or antagonist inhibits CNS myelin-induced neurite outgrowth inhibition and/or promotes axonal regeneration. In various embodiments, the LRP-1 inhibitor or antagonist competitively displaces, reduces, inhibits and/or prevents binding of myelin-associated inhibitory proteins (e.g., myelin associated glycoprotein (MAG), oligodendrocyte myelin glycoprotein (OMgp), Nogo-A, Nogo-B, Nogo-C and/or fragments thereof) to LRP-1.

In a further aspect, the invention provides methods for increasing, promoting, restoring or enhancing neurite outgrowth or axonal regeneration in a subject. In some embodiments, the methods comprise administering to a subject in need thereof an effective amount of a LRP-1 inhibitor or antagonist, wherein the LRP-1 inhibitor or antagonist increases, promotes or enhances neurite outgrowth or axonal regeneration in the subject.

In a further aspect, the invention provides methods of treating a central nervous system disease, disorder or injury in a subject. In some embodiments, the methods comprise administering to a subject in need thereof an effective amount of a LRP-1 inhibitor or antagonist; wherein the LRP-1 inhibitor or antagonist inhibits CNS myelin-induced neurite outgrowth inhibition and/or promotes axonal regeneration.

In a related aspect, the invention provides methods for inhibiting degeneration of a neuron, the method comprising contacting the neuron with an inhibitor or antagonist of LRP-1, thereby inhibiting degeneration of the neuron.

With respect to the embodiments of the methods, in some embodiments, the neuron is a central nervous system neuron. The neuron can be in vitro or in vivo.

In various embodiments, the myelin-associated inhbitory protein is selected from the group consisting of myelin associated glycoprotein (MAG), oligodendrocyte myelin glycoprotein (OMgp), Nogo-A, Nogo-B, Nogo-C, ephrin-B3, Sema4D/CD100, repulsive guidance molecule b, and/or fragments thereof.

In some embodiments, the inhibitor of LRP-1 is receptor associated protein (RAP). As appropriate, RAP can be delivered to the neuron as a polypeptide (or variants or fragments thereof), or as a polynucleotide encoding RAP (e.g., in a plasmid or viral vector).

In various embodiments, the inhibitor of LRP-1 is a soluble extracellular ligand binding domain of LRP-1. As appropriate, the soluble extracellular ligand binding domain of LRP-1 can be delivered to the neuron as a polypeptide (or variants or fragments thereof), or as a polynucleotide encoding the soluble extracellular ligand binding domain of LRP-1(e.g., in a plasmid or viral vector). In some embodiments, the soluble extracellular ligand binding domain of LRP-1 is selected from the group consisting of LRP-1(6-94) (SEQ ID NO:3), LRP 1 (787-1164) (SEQ ID NO:4), LRP-1(804-1185) (SEQ ID NO:5), LRP-1(2462-2923) (SEQ ID NO:6), LRP-1(3274-3764) (SEQ ID NO:7), LRP 1 (3331-3778) (SEQ ID NO:8), and fragments thereof. In some embodiments, the soluble extracellular ligand binding domain of LRP-1 is selected from the group consisting of LRP-1(787-1164) (SEQ ID NO:4), LRP-1(804-1185) (SEQ ID NO:5), LRP-1(3274-3764) (SEQ ID NO:7), LRP 1 (3331-3778) (SEQ ID NO:8), and fragments thereof. In some embodiments, the soluble extracellular ligand binding domain of LRP-1 has at least 80%, 85%, 90%, 93%, 95%, 97% or 99% sequence identity to a soluble extracellular ligand binding domain of LRP-1 selected from the group consisting of LRP-1(6-94) (SEQ ID NO:3), LRP 1 (787-1164) (SEQ ID NO:4), LRP-1(804-1185) (SEQ ID NO:5), LRP-1(2462-2923) (SEQ ID NO:6), LRP-1 (3274-3764) (SEQ ID NO:7), LRP 1 (3331-3778) (SEQ ID NO:8), and fragments thereof. In some embodiments, the soluble extracellular ligand binding domain of LRP-1 comprises one or more of the LRP-1 CII domain (LRP-1(804-1185) (SEQ ID NO:5)) and the LRP-1 CIV domain LRP 1 (3331-3778) (SEQ ID NO:8)). In various embodiments, one or more soluble extracellular ligand binding domains of LRP-1 can be fused together. In some embodiments, the soluble extracellular ligand binding domain of LRP-1 is attached (e.g., conjugated or fused) to an immunoglobulin Fc domain. In various embodiments, the soluble extracellular ligand binding domain of LRP-1 competitively displaces myelin-associated inhibitory proteins (e.g., myelin associated glycoprotein (MAG), oligodendrocyte myelin glycoprotein (OMgp), Nogo-A, Nogo-B, Nogo-C and/or fragments thereof), thereby inhibiting, reducing and/or preventing myelin-associated inhibitory proteins (e.g., myelin associated glycoprotein (MAG), oligodendrocyte myelin glycoprotein (OMgp), Nogo-A, Nogo-B, Nogo-C and/or fragments thereof) from binding to LRP-1.

In some embodiments, the inhibitor of LRP-1 is an inhibitory nucleic acid that inhibits the expression of LRP-1. For example, the inhibitory nucleic acid that inhibits the expression of LRP-1 can be a siRNA, a shRNA, an antisense RNA or a ribozyme. As appropriate, the inhibitory nucleic acid can be delivered in a viral vector, for example, a neurotropic viral vector. In some embodiments, the inhibitor of LRP-1 is a siRNA or shRNA that specifically inhibits the expression of LRP-1. As appropriate, the siRNA or shRNA can be delivered in a lentiviral vector, a herpesvirus vector or an adenoviral vector.

In some embodiments, the inhibitor of LRP-1 reduces or inhibits binding and/or endocytosis of myelin. In some embodiments, the inhibitor of LRP-1 reduces or inhibits binding and/or endocytosis of one or more myelin-associated inhibitory proteins (e.g., myelin associated glycoprotein (MAG), oligodendrocyte myelin glycoprotein (OMgp), Nogo-A, Nogo-B, Nogo-C and/or fragments thereof). In some embodiments, the inhibitor of LRP-1 inhibits myelin associated glycoprotein (MAG) activation of Rho or association with p75NTR (a.k.a., NGFR or nerve growth factor receptor; Ref Seq No. NM_002507.3→NP_002498.1). In some embodiments, the inhibitor of LRP-1 inhibits LRP-1 association with the p75NTR.

In various embodiments, the subject has experienced an injury to the central nervous system. For example, the subject may have a neurodegenerative disease. In some embodiments, has experienced a surgical resection, spinal cord injury or a traumatic brain injury. In some embodiments, the central nervous system disease, disorder or injury is selected from the group consisting of cranial or cerebral trauma, spinal cord injury, CNS injury resulting from tumor resection, transverse myelitis, optical myelitis, Guillain-Barré syndrome (GBS), stroke, multiple sclerosis, monophasic demyelination, encephalomyelitis, multifocal leukoencephalopathy, panencephalitis, Marchiafava-Bignami disease, pontine myelinolysis, adrenoleukodystrophy, Pelizaeus-Merzbacher disease, Spongy degeneration, Alexander's disease, Canavan's disease, metachromatic leukodystrophy, and Krabbe's disease.

In some embodiments, the inhibitor of LRP-1 is administered directly to injury.

In some embodiments, the subject is a human.

In a further aspect, the invention provides methods of identifying an agent for use in for increasing, promoting or enhancing neurite outgrowth and/or axonal regeneration and/or inhibiting degeneration of a neuron, the method comprising: (a) contacting a neuronal cell with a candidate agent; (b) determining a level of LRP-1 function; and (c) measuring the level of neurite outgrowth. Candidate agents of interest reduce or inhibit LRP-1 function and increase the level of neurite growth of the neuronal cell.

Definitions

The term "low density lipoprotein receptor-related protein 1" or "LRP-1" interchangeably refer to nucleic acids and polypeptide polymorphic variants, alleles, mutants, and interspecies homologs that: (1) have an amino acid sequence that has greater than about 90% amino acid sequence identity, for example, 91%, 92%, 93%, 94%, 95%, 96%, 97%, 98% or 99% or greater amino acid sequence identity, preferably over a region of at least about 25, 50, 100, 200, 300, 400, or more amino acids, or over the full-length, to an amino acid sequence encoded by a LRP-1 nucleic acid (see, e.g., GenBank Accession No. NM_002332.2) or to an amino acid sequence of a LRP-1 polypeptide (see, e.g., GenBank Accession No. NP_002323.2); (2) bind to antibodies, e.g., polyclonal antibodies, raised against an immunogen comprising an amino acid sequence of a LRP-1 polypeptide (e.g., LRP-1 polypeptides described herein); or an amino acid sequence encoded by a LRP-1 nucleic acid (e.g., LRP-1 polynucleotides described herein), and conservatively modified variants thereof; (3) specifically hybridize under stringent hybridization conditions to an anti-sense strand corresponding to a nucleic acid sequence encoding a LRP-1 protein, and conservatively modified variants thereof; (4) have a nucleic acid sequence that has greater than about 90%, preferably greater than about 91%, 92%, 93%, 94%, 95%, 96%, 97%, 98%, 99%, or higher nucleotide sequence identity, preferably over a region of at least about 25, 50, 100, 200, 500, 1000, 2000 or more nucleotides, or over the full-length, to a LRP-1 nucleic acid (e.g., LRP-1 polynucleotides, as described herein, and LRP-1 polynucleotides that encode LRP-1 polypeptides, as described herein).

The terms "low density lipoprotein receptor-related protein associated protein 1", "LRPAP1," "alpha-2-macroglobulin receptor-associated protein," and "RAP" interchangeably refer to nucleic acids and polypeptide polymorphic variants, alleles, mutants, and interspecies homologs that: (1) have an amino acid sequence that has greater than about 90% amino acid sequence identity, for example, 91%, 92%, 93%, 94%, 95%, 96%, 97%, 98% or 99% or greater amino acid sequence identity, preferably over a region of at least about 25, 50, 100, 200, 300, 400, or more amino acids, or over the full-length, to an amino acid sequence encoded by a RAP nucleic acid (see, e.g., GenBank Accession No. NM_002337.2) or to an amino acid sequence of a RAP polypeptide (see, e.g., GenBank Accession No. NP_002328.1); (2) bind to antibodies, e.g., polyclonal antibodies, raised against an immunogen comprising an amino acid sequence of a RAP polypeptide (e.g., RAP polypeptides described herein); or an amino acid sequence encoded by a RAP nucleic acid (e.g., RAP polynucleotides described herein), and conservatively modified variants thereof; (3) specifically hybridize under stringent hybridization conditions to an anti-sense strand corresponding to a nucleic acid sequence encoding a RAP protein, and conservatively modified variants thereof; (4) have a nucleic acid sequence that has greater than about 90%, preferably greater than about 91%, 92%, 93%, 94%, 95%, 96%, 97%, 98%, 99%, or higher nucleotide sequence identity, preferably over a region of at least about 25, 50, 100, 200, 500, 1000, 2000 or more nucleotides, or over the full-length, to a RAP nucleic acid (e.g., RAP polynucleotides, as described herein, and RAP polynucleotides that encode RAP polypeptides, as described herein).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, $\alpha$-carboxyglutamate, and O-phosphoserine. Amino acid analogs refers to compounds that have the same basic chemical structure as a naturally occurring amino acid, i.e., an $\alpha$ carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W); and
7) Serine (S), Threonine (T)

(see, e.g., Creighton, Proteins (1984)).

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

The terms "identical" or percent "identity," in the context of two or more nucleic acids or polypeptide sequences, refer to two or more sequences or subsequences that are the same or have a specified percentage of amino acid residues or nucleotides that are the same (i.e., share at least about 80% identity, for example, at least about 85%, 90%, 91%, 92%, 93%, 94%, 95%, 96%, 97%, 98%, 99% identity over a specified region to a reference sequence, e.g., a LRP-1 polynucleotide or polypeptide sequence or fragment thereof as described herein (e.g., SEQ ID NOs: 1, 2, 3, 4, 5, 6, 7, 8), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, for example, over a region that is 50-100 amino acids or nucleotides in length, or over the full-length of a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to LRP-1 nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48:443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., eds., Current Protocols in Molecular Biology (1995 supplement)).

Examples of algorithms that are suitable for determining percent sequence identity and sequence similarity are the BLAST and BLAST 2.0 algorithms, which are described in Altschul et al., J. Mol. Biol. 215:403-410 (1990) and Altschul et al., Nucleic Acids Res. 25:3389-3402 (1977), respectively. Software for performing BLAST analyses is publicly available through the National Center for Biotechnology Information (on the worldwide web at ncbi.nlm.nih.gov/). The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89: 10915 (1989)).

The BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "individual," "patient,", "subject" interchangeably refer to a mammal, for example, a human, a non-human primate, a domesticated mammal (e.g., a canine or a feline), an agricultural mammal (e.g., equine, bovine, ovine, porcine), or a laboratory mammal (e.g., rattus, murine, lagomorpha, hamster).

The term "antibody" as used herein refers to polyclonal and monoclonal antibodies and fragments thereof, and immunologic binding equivalents thereof. The term "antibody" refers to a homogeneous molecular entity, or a mixture such as a polyclonal serum product made up of a plurality of different molecular entities, and broadly encompasses naturally-occurring forms of antibodies (for example, IgG, IgA, IgM, IgE) and recombinant antibodies such as single-chain antibodies, chimeric and humanized antibodies and multi-specific antibodies. The term "antibody" also refers to fragments and derivatives of all of the foregoing, and may further comprise any modified or derivatised variants thereof that retains the ability to specifically bind an epitope. Antibody derivatives may comprise a protein or chemical moiety conjugated to an antibody. A monoclonal antibody is capable of selectively binding to a target antigen or epitope. Antibodies may include, but are not limited to polyclonal antibodies, monoclonal antibodies (mAbs), humanized or chimeric antibodies, camelized antibodies, single chain antibodies (scFvs), Fab fragments, $F(ab')_2$ fragments, disulfide-linked Fvs (sdFv) fragments, for example, as produced by a Fab expression library, anti-idiotypic (anti-Id) antibodies, intrabodies, nanobodies, synthetic antibodies, and epitope-binding fragments of any of the above.

The terms "systemic administration" and "systemically administered" refer to a method of administering an inhibitor of LRP-1 to a mammal so that the inhibitor is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration.

The term "co-administer" and "co-administering" and variants thereof refer to the simultaneous presence of two or more active agents in the blood of an individual. The active agents that are co-administered can be concurrently or sequentially delivered. As used herein, inhibitors of LRP-1 can be co-administered with another active agent efficacious in promoting neuronal regeneration in the CNS.

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

The terms "treating" and "treatment" and variants thereof refer to delaying the onset of, retarding or reversing the progress of, alleviating or preventing either the disease or condition to which the term applies (injury or damage to the CNS, e.g., resulting from surgical resection, spinal cord injury or traumatic brain injury), or one or more symptoms of such disease or condition. Treating and treatment also refers to increasing, enhancing and promoting neuron regeneration and/or nerve growth in the presence of injury to the CNS. Treating and treatment encompass both therapeutic and prophylactic treatment regimens.

The term "effective amount" or "therapeutically effective amount" refers to the amount of an active agent sufficient to induce a desired biological result (e.g., inhibition of function of LRP-1, promotion and/or restoration of neuronal regeneration and/or neurite growth). That result may be alleviation of the signs, symptoms, or causes of a disease, or any other desired alteration of a biological system. The term "therapeutically effective amount" is used herein to denote any amount of the formulation which causes a substantial improvement in a disease condition when applied to the affected areas repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "increasing," "promoting," "enhancing" refers to increasing the neurite growth and/or neuronal regeneration in the CNS in a subject by a measurable amount using any method known in the art. The neurite growth and/or neuronal regeneration in the CNS is increased, promoted or enhanced if the neurite growth and/or neuronal regeneration is at least about 10%, 20%, 30%, 50%, 80%, or 100% increased in comparison to the neurite growth and/or neuronal regeneration prior to administration of an inhibitor of LRP-1. In some embodiments, the neurite growth and/or neuronal regeneration is increased, promoted or enhanced by at least about 1-fold, 2-fold, 3-fold, 4-fold, or more in comparison to the neurite growth and/or neuronal regeneration prior to administration of the inhibitor of LRP-1.

The terms "inhibiting," "reducing," "decreasing" with respect to LRP-1 function refers to inhibiting the function of LRP-1 in a subject by a measurable amount using any method known in the art (e.g., binding and/or endocytosis of myelin; cell-signaling mediated downstream of LRP-1, e.g., myelin associated glycoprotein (MAG) activation of Rho or association with p75NTR). The LRP-1 function is inhibited, reduced or decreased if the measurable amount of LRP-1 function, e.g., of ligand binding and/or downstream signaling, is at least about 10%, 20%, 30%, 50%, 80%, or 100% reduced in comparison to the measurable amount of LRP-1 function prior to administration of an inhibitor of LRP-1. In some embodiments, the LRP-1 function is inhibited, reduced or decreased by at least about 1-fold, 2-fold, 3-fold, 4-fold, or more in comparison to the LRP-1 function prior to administration of the inhibitor of LRP-1.

The term "selective inhibition" or "selectively inhibit" as referred to a biologically active agent refers to the agent's ability to preferentially reduce the target signaling activity as compared to off-target signaling activity, via direct or indirect interaction with the target. In various embodiments, the inhibitory agent inhibits, reduces or prevents the binding between LRP1 and the specific inhibitory components of myelin, e.g., the binding between LRP1 and myelin-associated glycoprotein (MAG).

The term "candidate agent" refers to any molecule of any composition, including proteins, peptides, nucleic acids, lipids, carbohydrates, organic molecules, inorganic molecules, and/or combinations of molecules which are suspected to be capable of inhibiting a measured parameter (e.g., LRP-1 activity, expression, signal transduction, binding between LRP1 and the specific inhibitory components of myelin, e.g., the binding between LRP1 and myelin-associated glycoprotein (MAG), neuron regeneration, neurite growth) in a treated cell, tissue or subject in comparison to an untreated cell, tissue or subject.

The term "antagonist" or "inhibitor" as used herein refers to a molecule having the ability to inhibit a biological function of a target polypeptide (i.e., LRP-1). Accordingly, the term "antagonist" is defined in the context of the biological role of the target polypeptide. While preferred antagonists herein specifically interact with (e.g. bind to) the target, molecules that inhibit a biological activity of the target polypeptide by interacting with other members of the signal transduction pathway of which the target polypeptide is a member are also specifically included within this definition. Antagonists, as defined herein, without limitation, include antibodies and immunoglobulin variants, peptides, peptidomimetics, non-peptide small molecules, inhibitory nucleic acids, and oligonucleotide decoys. In various embodiments, the inhibitory agent (e.g., antagonist or inhibitor) competitively displaces inhibitory components of myelin, e.g., myelin-associated glycoprotein (MAG) from binding to LRP1 and thereby inhibits, reduces or prevents the binding between LRP1 and the specific inhibitory components of myelin, e.g., the binding between LRP1 and myelin-associated glycoprotein (MAG).

BRIEF DESCRIPTION OF THE DRAWINGS

FIG. 2 illustrates the sequence coverage for MAG as determined by LC/MS-MS identified by our CII/CIV affinity precipitation of proteins from purified myelin. Residues underlined were identified by automated database search of the peptides associated with CII and CIV. Sequence coverage is 19.46%. FIG. 2 discloses SEQ ID NO: 10.

DETAILED DESCRIPTION

1. Introduction

Figures 1A, 1B, 1C:
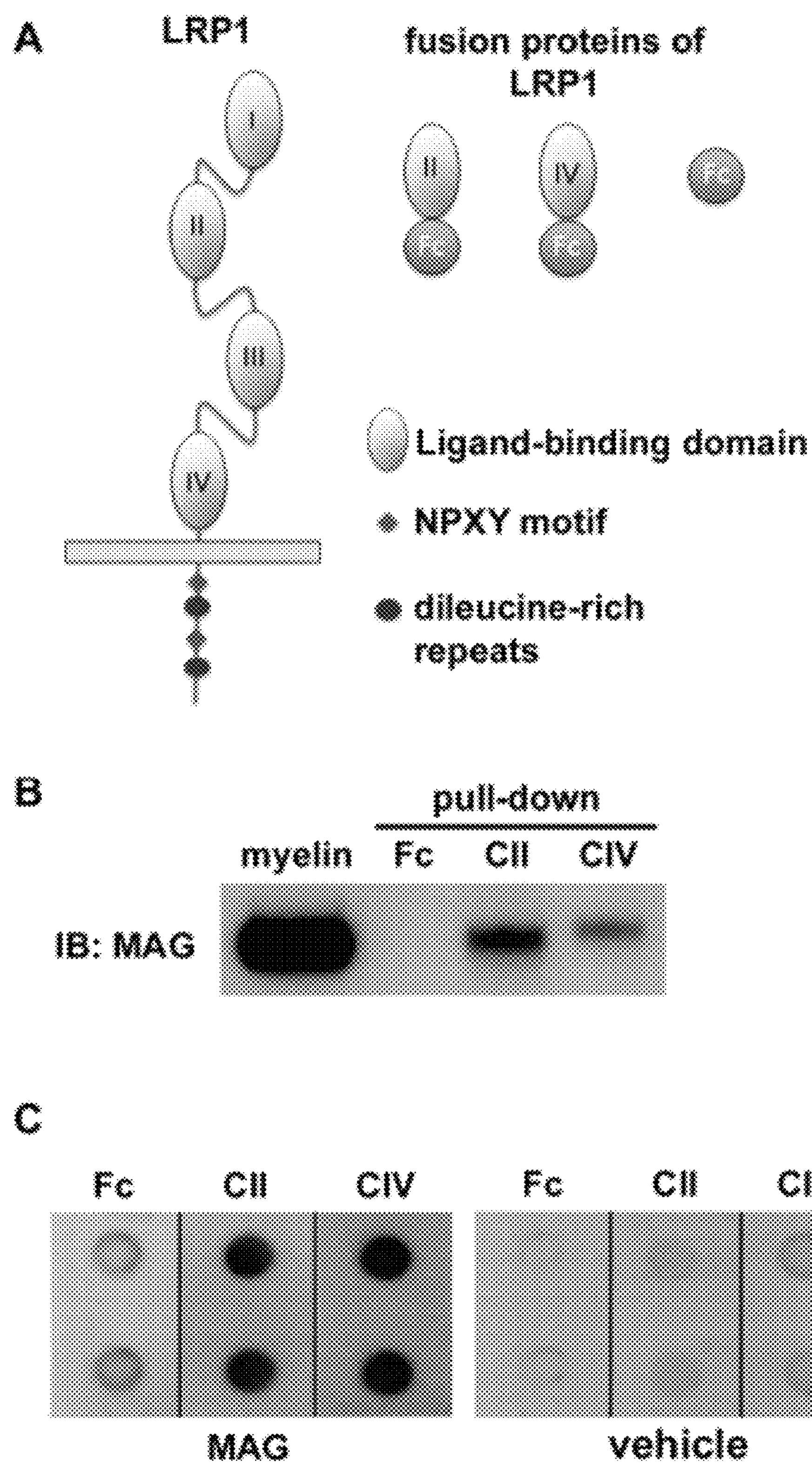
FIGS. 1A-1G illustrate that LRP1 is a receptor for MAG (A) Schematic diagram showing the relationship of CII-Fc and CIV-Fc to the intact structure of LRP1. (B) CII-Fc, CIV-Fc, and Fc were incubated with purified myelin. The Fc proteins and associated myelin-derived proteins were precipitated with Protein A-Sepharose. Immunoblot analysis was performed to detect MAG. (C) CII-Fc, CIV-Fc, and Fc (1 μg) were immobilized in duplicate on nitrocellulose membranes and incubated with MAG-Fc (10 μg/ml) or vehicle. MAG-binding was detected using MAG-specific antibody. Lack of binding to immobilized Fc was evidence for specificity. (D) N2a cell extracts were incubated with MAG-Fc or Fc, which were pre-immobilized on Protein A-Sepharose beads. LRP1 was detected in the pull-down by immunoblot analysis. The two left-hand lanes show an immunoblot analysis for LRP1 in whole cell extracts from N2a cells (LRP1+) and N2a cells in which LRP1 was silenced with shRNA (LRP1−). The absence of LRP1 in the LRP1-extracts proves the specificity of the antibody. LRP1 was not detected when immobilized MAG-Fc or Fc were incubated with extraction buffer (vehicle, no cells) as a control (middle lanes). (E) N20.1 cell extracts were treated with 200 nM GST-RAP or with GST and then affinity precipitated with MAG-Fc coupled to Protein A-Sepharose. Affinity-precipitated samples were subjected to immunoblot analysis for LRP1. N20.1 whole cell extracts were subjected to SDS-PAGE and immune-blot analysis, without affinity precipitation, as a control (left-hand lane). (F) Recombinant MAG-Fc or Fc was immobilized on Protein A-Sepharose and incubated with purified LRP1 or with vehicle. Affinity precipitated proteins were subjected to immune-blot analysis for LRP1. (G) LRP1-expressing and -deficient N2a cells were incubated with 25 nM $^{125}$I-MAG-Fc, in the presence or absence of a 50-fold molar excess of unlabeled MAG-Fc. Specific MAG-Fc internalization was determined (*, $p<0.01$).

The present invention is based, in part, on the discovery that inhibition of the function and/or signaling through LRP-1 is a target in treatment of multiple injuries to the CNS neurons, including without limitation trauma, multiple sclerosis, and various forms of neurodegeneration. Disrupting of LRP-1 function in neurons is an approach that allows for the disruption of myelin signaling to RhoA without directly influencing regulatory molecules of the cell such as PTEN. Additionally, while antibodies directed against myelin-associated inhibitory proteins (e.g., myelin associated glycoprotein (MAG), oligodendrocyte myelin glycoprotein (OMgp), Nogo-A, Nogo-B, Nogo-C and/or fragments thereof) may yield some benefit, no single antibody can be directed against all inhibitory components. LRP-1 disruption represents an approach which accomplishes this task, likely yielding superior regenerative results. Disruption of receptor binding is a long-standing pharmacologic approach in humans and the risk of adverse reaction is very likely to be less than the use of antibodies or inhibitors of PTEN or ROCK. Because disruption of LRP-1 function has been shown to restore the growth capacity of neurons on myelin, as well as disrupt myelin signaling to RhoA, we believe LRP-1 represents a superior therapeutic target compared to previously discovered participating receptors.

It was demonstrated that low density lipoprotein receptor-related protein-1 (LRP-1) is capable of inducing neurite outgrowth via trans-activation of Trk receptors. This work demonstrated a role of LRP-1 in neuronal differentiation. However, LRP-1 has also recently been demonstrated as the principle receptor needed for the phagocytosis of myelin debris. Therefore, LRP-1 may be participating in myelin-mediated neurite outgrowth inhibition. Because LRP-1 is known to have a neurotrophic capacity, it is counterintuitive to think that LRP-1 could be participating in an inhibitory process. However, contrary to the anticipated result, the present application shows that disturbing LRP-1 function in neuronal cells has a tremendous capacity for restoring the ability of neurons to extend neurites in the presence of myelin. The data presented herein demonstrates that LRP-1 potently influences the growth state of neurons and mediates the inhibitory effects of myelin on nerve growth. Accordingly, LRP-1 is identified as a novel target in neuronal regeneration.

2. Subjects Amenable to the Present Methods

Inhibiting the function of LRP-1 and inhibitors of LRP-1 can be used in methods for inhibiting neuron (e.g., axon) degeneration and promoting neuron regeneration and/or neurite growth. Inhibition of the function of LRP-1 is useful in the therapy of, for example, (i) disorders of the nervous system (e.g., neurodegenerative diseases), (ii) conditions of the nervous system that are secondary to a disease, condition, or therapy having a primary effect outside of the nervous system, (iii) injuries to the nervous system, particularly the central nervous system, e.g., caused by physical, mechanical, or chemical trauma, (iv) pain, (v) ocular-related neurodegeneration, (vi) memory loss, and (vii) psychiatric disorders. Non-limiting examples of some of these diseases, conditions, and injuries are provided below.

Examples of neurodegenerative diseases and conditions that can be prevented or treated according to the invention include amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, progressive bulbar palsy, inherited muscular atrophy, invertebrate disk syndromes (e.g., herniated, ruptured, and prolapsed disk syndromes), cervical spondylosis, plexus disorders, thoracic outlet destruction syndromes, peripheral neuropathies, prophyria, mild cognitive impairment, Alzheimer's disease, Huntington's disease, Parkinson's disease, Parkinson's-plus diseases (e.g., multiple system atrophy, progressive supranuclear palsy, and corticobasal degeneration), dementia with Lewy bodies, frontotemporal dementia, demyelinating diseases (e.g., Guillain-Barre syndrome and multiple sclerosis), Charcot-Marie-Tooth disease (CMT; also known as Hereditary Motor and Sensory Neuropathy (HMSN), Hereditary Sensorimotor Neuropathy (HSMN), and Peroneal Muscular Atrophy), prion disease (e.g., Creutzfeldt-Jakob disease, Gerstmann-Straussler-Scheinker syndrome (GSS), fatal familial insomnia (FFI), and bovine spongiform encephalopathy (BSE, commonly known as mad cow disease)), Pick's disease, epilepsy, and AIDS demential complex (also known as HIV dementia, HIV encephalopathy, and HIV-associated dementia).

Inhibitors of LRP-1 function find use in promoting neuron regeneration and neurite growth in the presence of injury to the CNS. Exemplary CNS diseases, disorders or injuries include, but are not limited to, multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease) and Wallerian Degeneration, optic neuritis, transverse myelitis, amylotrophic lateral sclerosis (ALS), Huntington's disease, Alzheimer's disease, Parkinson's disease, surgical resection, spinal cord injury, CNS injury resulting from tumor resection, transverse myelitis, optical myelitis, Guillain-Barré syndrome (GBS), stroke, traumatic brain injury, post radiation injury, neurologic complications of chemotherapy, stroke, acute ischemic optic neuropathy, vitamin E deficiency, isolated vitamin E deficiency syndrome, Bassen-Kornzweig syndrome, Marchiafava-Bignami syndrome, metachromatic leukodystrophy, trigeminal neuralgia, epilepsy and Bell's palsy.

3. Inhibitors of LRP-1 Function

Inhibitors of LRP-1 function are known in the art and find use. Illustrative inhibitors of LRP-1 function, soluble LRP-1 receptor polypeptides, inhibitory nucleic acids that inhibit expression of LRP-1, or anti-LRP-1 antibodies. Inhibitors of use may reduce, inhibit or eliminate, ligand binding function (particularly binding to myelin-associated inhibitory proteins, e.g., myelin associated glycoprotein (MAG), oligodendrocyte myelin glycoprotein (OMgp), Nogo-A, Nogo-B, Nogo-C and/or fragments thereof), signaling function and/or expression of LRP-1. Illustrative molecules that interfere with ligand binding to LRP-1 include without limitation receptor associated protein (RAP), lactoferrin, suramin, α2-macroglobulin and soluble LRP-1 receptor polypeptides (e.g., LRP-1 mini-receptors). Moreover, Nelfinavir has been found to reduce protein levels of LRP-1.

In various embodiments, the inhibitors competitively displace, reduce, inhibit and/or eliminate the binding of myelin-associated inhibitory proteins (e.g., myelin associated glycoprotein (MAG), oligodendrocyte myelin glycoprotein (OMgp), Nogo-A, Nogo-B, Nogo-C and/or fragments thereof) to LRP-1. In various embodiments, the inhibitor of LRP-1 function, e.g., binding to myelin-associated inhibitory proteins (e.g., myelin associated glycoprotein (MAG), oligodendrocyte myelin glycoprotein (OMgp), Nogo-A, Nogo-B, Nogo-C and/or fragments thereof) is a soluble ligand binding domain of LRP-1(e.g., a soluble mini-receptor of LRP-1). Soluble LRP-1 mini-receptors are known in the art, and have been described, e.g., in Obermoeller-McCormick, et. al., *J Cell Sci*. (2001) 114:899-908; and Bu, *J Biol Chem*. (1996) 271:22218-24. Illustrative soluble ligand binding domains of LRP-1 include, e.g., LRP-1(6-94) (SEQ ID NO:3), LRP 1 (787-1164) (SEQ ID NO:4), LRP-1(804-1185) (SEQ ID NO:5), LRP-1 (2462-2923) (SEQ ID NO:6), LRP-1(3274-3764) (SEQ ID NO:7), LRP 1 (3331-3778) (SEQ ID NO:8), and fragments thereof. In some embodiments, the soluble extracellular ligand binding domain of LRP-1 is selected from the group consisting of LRP-1(787-1164) (SEQ ID NO:4), LRP-1(804-1185) (SEQ ID NO:5), LRP-1(3274-3764) (SEQ ID NO:7), LRP 1 (3331-3778) (SEQ ID NO:8), and fragments thereof. In some embodiments, the soluble extracellular ligand binding domain of LRP-1 comprises one or more of the LRP-1 CII domain (LRP-1(804-1185) (SEQ ID NO:5)) and the LRP-1 CIV domain LRP 1 (3331-3778) (SEQ ID NO:8)). In various embodiments, one or more soluble extracellular ligand binding domains of LRP-1 can be fused together, e.g., expressed as a fusion protein. In some embodiments, the soluble extracellular ligand binding domain of LRP-1 has at least 80%, 85%, 90%, 93%, 95%, 97% or 99% sequence identity to a soluble extracellular ligand binding domain of LRP-1 selected from the group consisting of LRP-1(6-94) (SEQ ID NO:3), LRP-1(787-1164) (SEQ ID NO:4), LRP-1(804-1185) (SEQ ID NO:5), LRP-1(2462-2923) (SEQ ID NO:6), LRP-1(3274-3764) (SEQ ID NO:7), LRP-1(3331-3778) (SEQ ID NO:8), and fragments thereof.

Antibodies and antibody fragments that competitively disrupt, reduce and/or inhibit binding of myelin-associated inhibitory proteins (e.g., myelin associated glycoprotein (MAG), oligodendrocyte myelin glycoprotein (OMgp), Nogo-A, Nogo-B, Nogo-C and/or fragments thereof) to LRP-1 also find use. In various embodiments, the antibodies specifically bind to an extracellular ligand (e.g. myelin-associated inhibitory proteins, including without limitation myelin associated glycoprotein (MAG), oligodendrocyte myelin glycoprotein (OMgp), Nogo-A, Nogo-B, Nogo-C and/or fragments thereof) binding domain of LRP-1, e.g. the CII and/or CIV domains, e.g., to an epitope within LRP-1 (787-1164) (SEQ ID NO:4), LRP-1(804-1185) (SEQ ID NO:5), LRP-1(3274-3764) (SEQ ID NO:7), LRP-1(3331-3778) (SEQ ID NO:8). In other embodiments, the antibodies may specifically bind to one or more myelin-associated inhibitory proteins, including without limitation myelin associated glycoprotein (MAG), oligodendrocyte myelin glycoprotein (OMgp), Nogo-A, Nogo-B, Nogo-C, ephrin-B3, Sema4D/CD100, repulsive guidance molecule b, and/or fragments thereof.

In some embodiments, the inhibitor of LRP-1 is an inhibitory nucleic acid that specifically inhibits the expression of LRP-1. An "inhibitory nucleic acid" means an RNA, DNA, or combination thereof that interferes or interrupts the translation of mRNA. Inhibitory nucleic acids can be single or double stranded. The nucleotides of the inhibitory nucleic acid can be chemically modified, natural or artificial. The terms "short-inhibitory RNA" and "siRNA" interchangeably refer to short double-stranded RNA oligonucleotides that mediate RNA interference (also referred to as "RNA-mediated interference," or RNAi). RNAi is a highly conserved gene silencing event functioning through targeted destruction of individual mRNA by a homologous double-stranded small interfering RNA (siRNA) (Fire, A. et al., Nature 391:806-811 (1998)). Mechanisms for RNAi are reviewed, for example, in Bayne and Allshire, Trends in Genetics (2005) 21:370-73; Morris, Cell Mol Life Sci (2005) 62:3057-66; Filipowicz, et al., Current Opinion in Structural Biology (2005) 15:331-41.

Methods for the design of siRNA or shRNA target sequences have been described in the art. Among the factors to be considered include: siRNA target sequences should be specific to the gene of interest and have about 20-50% GC content (Henshel et al., Nucl. Acids Res., 32: 113-20 (2004); G/C at the 5' end of the sense strand; A/U at the 5' end of the antisense strand; at least 5 A/U residues in the first 7 bases of the 5' terminal of the antisense strand; and no runs of more than 9 G/C residues (Ui-Tei et al., Nucl. Acids Res., 3: 936-48 (2004)). Additionally, primer design rules specific to the RNA polymerase will apply. For example, for RNA polymerase III, the polymerase that transcribes from the U6 promoter, the preferred target sequence is 5'-GN18-3'. Runs of 4 or more Ts (or As on the other strand) will serve as terminator sequences for RNA polymerase III and should be avoided. In addition, regions with a run of any single base should be avoided (Czauderna et al., Nucl. Acids Res., 31: 2705-16 (2003)). It has also been generally recommended that the mRNA target site be at least 50-200 bases downstream of the start codon (Sui et al., Proc. Natl. Acad. Sci. USA, 99: 5515-20 (2002); Elbashir et al., Methods, 26: 199-213 (2002); Duxbury and Whang, J. Surg. Res., 117: 339-44 (2004) to avoid regions in which regulatory proteins might bind. Additionally, a number of computer programs are available to aid in the design of suitable siRNA and shRNAs for use in suppressing expression of LRP-1, e.g., encoded by the nucleic sequence of GenBank Ref. NM_002332.2.

A program, siDESIGN from Dharmacon, Inc. (Lafayette, Colo.), permits predicting siRNAs for any nucleic acid sequence, and is available on the World Wide Web at dharmacon.com. Programs for designing siRNAs are also available from others, including Genscript (available on the Web at genscript.com/ssl-bin/app/rnai) and, to academic and non-profit researchers, from the Whitehead Institute for Biomedical Research found on the worldwide web at "jura.wi.mit-.edu/pubint/http://iona.wi.mit.edu/siRNAext/."

Ribozymes that cleave mRNA at site-specific recognition sequences can be used to destroy target mRNAs, particularly through the use of hammerhead ribozymes. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art.

Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a target mRNA. In addition, ribozymes possess highly specific endoribonuclease activity, which autocatalytically cleaves the target sense mRNA.

With regard to antisense, siRNA or ribozyme oligonucleotides, phosphorothioate oligonucleotides can be used. Modifications of the phosphodiester linkage as well as of the heterocycle or the sugar may provide an increase in efficiency. Phophorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

4. Formulation and Administration of Inhibitors of LRP-1 Function

Compositions within the scope of the present invention include all compositions wherein one or more of the inhibitors of the present invention are contained in an amount which is effective to achieve its intended purpose (e.g., inhibition of LRP-1 function; promotion and/or restoration of neuron regeneration and/or neurite growth). While individual needs vary, determination of optimal ranges of effective amounts of each component is within the expertise of those of ordinary skill in the art.

Inhibitors within the scope of the present invention (e.g., RAP and/or other LRP-1 receptor antagonists, soluble LRP-1 receptor polypeptides, inhibitory nucleic acids that inhibit expression of LRP-1, or anti-LRP-1 antibodies) may be combined with one or more additional therapeutic agents useful to promote neuron regeneration and/or neurite growth in therapeutically effective amounts. In addition to active agents, the compositions can optionally comprise one or more pharmaceutical excipients well-known in the relevant arts. The optimal amounts of each active agent in the composition can be determined by the clinical practitioner using routine methods known to the ordinarily skilled artisan based on the guidance provided herein and in view of the information that is readily available in the art.

The inhibitors of LRP-1 may be administered as part of a pharmaceutical composition comprising one or more therapeutic agents and one or more suitable pharmaceutically acceptable carriers, such as one or more excipients or auxiliaries which facilitate processing of the therapeutic agents into preparations which can be used pharmaceutically. Preferably, such pharmaceutical compositions contain from about 0.01 to 99 percent, e.g., from about 0.25 to 75 percent of active compound(s), together with the excipient(s), particularly those compositions which can be administered orally or topically and which can be used for the preferred type of administration, such as tablets, dragees, slow release lozenges and capsules, gels, liquid suspensions, as well as suitable solutions for administration by parenteral administration, e.g., via intrathecal, intraspinal, intraventricular, intravenous, intramuscular, intracranial or subcutaneous infusion or injection.

The pharmaceutical compositions of the invention may be administered to any patient who may experience the beneficial effects of the LRP-1 inhibitors. Foremost among such patients are humans, although the invention is not intended to be so limited. Other patients include veterinary animals (cows, sheep, pigs, horses, dogs, cats and the like). In various embodiments, the inhibitor of LRP-1 is administered to a subject as part of an acute treatment regime to facilitate recovery of central nerve damage. For an acute treatment regime, administration of the inhibitor of LRP-1 is begun as soon as possible after damage or injury to a central nerve (e.g., within 1, 2, 3, 4, 6, 10, 12, 18, 24 hours of injury) and continued until a desired therapeutic endpoint is reached, e.g., detectable axonal sprouting, neuron regeneration and/or neurite growth, restoration of sensation and/or movement in the patient. For example, in various embodiments, administration of the inhibitor of LRP-1 is continued over a time period of 1, 2, 3, 4, 5, 6 days, 1, 2, 3 weeks, or 1, 2, 3, 4, 5, 6 months, or longer or shorter time periods, as appropriate to the patient. In various embodiments, the inhibitor of LRP-1 can be administered twice daily, once daily, once every two days, one every three days, twice weekly, weekly, every other week, monthly as appropriate. In various embodiments, the inhibitor of LRP-1 may be administered more often at the beginning of a treatment regime, and then tapered off over the course of treatment, as appropriate to the subject.

The pharmaceutical compositions of the invention may be administered by any means that achieve their intended purpose. For example, administration may be by parenteral, subcutaneous, intravenous, intramuscular, intradermal, intraperitoneal, transdermal, buccal, sublingual, intrathecal, intracerebroventricularly, intracranial, intraspinal, intranasal, ocular, pulmonary (e.g., via inhalation), topical routes or direct infusion. Alternatively, or concurrently, administration may be by the oral route. The dosage administered will be dependent upon the age, health, and weight of the recipient, kind of concurrent treatment, if any, frequency of treatment, and the nature of the effect desired.

In the methods of the invention the inhibitors of LRP-1 can be administered directly to the nervous system (particularly to the site of injury), intraspinally, intracerebroventricularly, or intrathecally, e.g. into a chronic lesion of a neurodegenerative disease or at the site(s) of traumatic injury. For treatment with an inhibitor of LRP-1, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly.

In some methods, two or more therapeutic agents are administered simultaneously, in which case the dosage of each agent administered falls within the ranges indicated. Supplementary active compounds also can be incorporated into the compositions used in the methods of the invention. For example, a compound described herein may be co-formulated with and/or co-administered with one or more additional therapeutic agents.

The invention encompasses any suitable delivery method for a LRP-1 inhibitor or antagonist to a selected target tissue, including bolus injection of an aqueous solution or implantation of a controlled-release system. Use of a controlled-release implant reduces the need for repeat injections.

The LRP-1 inhibitor or antagonist may be directly infused into the brain or into the CNS space. Various implants for direct brain infusion of compounds are known and are effective in the delivery of therapeutic compounds to human patients suffering from neurological disorders and/or CNS injury. These include chronic infusion into the brain or spine using a pump, stereotactically implanted, temporary interstitial catheters, permanent intracranial catheter implants, and surgically implanted biodegradable implants. See, e.g., Gill et al., supra; Scharfen et al., "High Activity Iodine-125 Interstitial Implant For Gliomas," Int. J. Radiation Oncology Biol. Phys. 24(4):583-91 (1992); Gaspar et al., "Permanent 1251 Implants for Recurrent Malignant Gliomas," Int. J. Radiation Oncology Biol. Phys. 43(5):977-82 (1999); chapter 66, pages 577-580, Bellezza et al., "Stereotactic Interstitial Brachytherapy," in Gildenberg et al., Textbook of Stereotactic and Functional Neurosurgery, McGraw-Hill (1998); and Brem et al., "The Safety of Interstitial Chemotherapy with BCNU-Loaded Polymer Followed by Radiation Therapy in the Treatment of Newly Diagnosed Malignant Gliomas: Phase I Trial," J. Neuro-Oncology 26: 111-23 (1995).

In some embodiments, the LRP-1 inhibitor or antagonist is administered to a patient by direct infusion into an appropriate region of the brain or spine. See, e.g., Gill et al., "Direct brain infusion of glial cell line-derived neurotrophic factor in Parkinson disease," Nature Med. 9: 589-95 (2003). Alternative techniques are available and may be applied to administer a LRP-1 inhibitor to the site of injury. For example, stereotactic placement of a catheter or implant can be accomplished using the Riechert-Mundinger unit and the ZD (Zamorano-Dujovny) multipurpose localizing unit. A contrast-enhanced computerized tomography (CT) scan, injecting 120 ml of omnipaque, 350 mg iodine/ml, with 2 mm slice thickness can allow three-dimensional multiplanar treatment planning (STP, Fischer, Freiburg, Germany). This equipment permits planning on the basis of magnetic resonance imaging studies, merging the CT and MRI target information for clear target confirmation.

The Leksell stereotactic system (Downs Surgical, Inc., Decatur, Ga.) modified for use with a GE CT scanner (General Electric Company, Milwaukee, Wis.) as well as the Brown-Roberts-Wells (BRW) stereotactic system (Radionics, Burlington, Mass.) can be used for this purpose. Thus, on the morning of the implant, the annular base ring of the BRW stereotactic frame can be attached to the patient's skull. Serial CT sections can be obtained at 3 mm intervals though the (target tissue) region with a graphite rod localizer frame clamped to the base plate. A computerized treatment planning program can be run on a VAX 11/780 computer (Digital Equipment Corporation, Maynard, Mass.) using CT coordinates of the graphite rod images to map between CT space and BRW space.

The compositions may also comprise a LRP-1 inhibitor or antagonist dispersed in a biocompatible carrier material that functions as a suitable delivery or support system for the compounds. Suitable examples of sustained release carriers include semipermeable polymer matrices in the form of shaped articles such as suppositories or capsules. Implantable or microcapsular sustained release matrices include polylactides (U.S. Pat. No. 3,773,319; EP 58,481), copolymers of L-glutamic acid and gamma-ethyl-L-glutamate (Sidman et al., Biopolymers 22:547-56 (1985)); poly(2-hydroxyethyl-methacrylate), ethylene vinyl acetate (Langer et al., J. Biomed. Mater. Res. 15:167-277 (1981); Langer, Chem. Tech. 12: 98-105 (1982)) or poly-D-(−)-3hydroxybutyric acid (EP 133,988).

In certain embodiments, the compositions for use in the methods of the present invention further comprise a targeting moiety. Targeting moieties include a protein or a peptide which directs localization to a certain part of the body, for example, to the brain or spine, or compartments therein. In certain embodiments, compositions for use in the methods of the present invention are attached or fused to a brain targeting moiety. The brain targeting moieties are attached covalently (e.g., direct, translational fusion, or by chemical linkage either directly or through a spacer molecule, which can be optionally cleavable) or non-covalently attached (e.g., through reversible interactions such as avidin:biotin, protein A:IgG, etc.). In other embodiments, the compounds for use in the methods of the present invention thereof are attached to one more brain targeting moieties. In additional embodiments, the brain targeting moiety is attached to a plurality of compounds for use in the methods of the present invention.

A CNS targeting moiety associated with a compound enhances CNS delivery of such compositions. A number of polypeptides have been described which, when fused to a therapeutic agent, delivers the therapeutic agent through the blood brain barrier (BBB). Non-limiting examples include the single domain antibody FC5 (Abulrob et al. (2005) J. Neurochem. 95, 1201-1214); mAB 83-14, a monoclonal antibody to the human insulin receptor (Pardridge et al. (1995) Pharmacol. Res. 12, 807-816); the B2, B6 and B8 peptides binding to the human transferrin receptor (hTfR) (Xia et al. (2000) J. Virol. 74, 11359-11366); the OX26 monoclonal antibody to the transferrin receptor (Pardridge et al. (1991) J. Pharmacol. Exp. Ther. 259, 66-70); diptheria toxin conjugates. (see, for e.g., Gaillard et al., International Congress Series 1277:185-198 (2005); and SEQ ID NOs: 1-18 of U.S. Pat. No. 6,306,365. The contents of the above references are incorporated herein by reference in their entirety.

Enhanced brain or spinal delivery of a composition is determined by a number of means well established in the art.

For example, administering to an animal a radioactively labelled compound linked to a CNS targeting moiety; determining CNS localization; and comparing localization with an equivalent radioactively labelled compound that is not associated with a brain targeting moiety. Other means of determining enhanced targeting are described in the above references.

Suitable oral pharmaceutical compositions of the present invention are manufactured in a manner which is itself well-known in the art, for example, by means of conventional mixing, granulating, dragee-making, dissolving, or lyophilizing processes. Thus, solid pharmaceutical preparations for oral use can be obtained by combining one or more of the compounds of the invention and optionally one or more additional active pharmaceutical ingredients with one or more solid excipients, optionally grinding the resulting mixture and processing the mixture of granules, after adding suitable auxiliaries, if desired or necessary, to obtain tablets or dragee cores.

Typically, the compounds may be administered to mammals, e.g., humans, at a dose of about 0.0025 mg/kg to about 50 mg/kg, for example, about 0.01 to about 25 mg/kg, for example, about 0.01 to about 5 mg/kg or an equivalent amount of the pharmaceutically acceptable salt, solvates or ester thereof.

Suitable excipients are, in particular, fillers such as saccharides, for example lactose, sucrose, fructose and the like; sugar alcohols such as mannitol, sorbitol, or xylitol and the like; cellulose preparations and/or calcium phosphates, for example tricalcium phosphate or calcium hydrogen phosphate; as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or poly (ethylene glycol). Dragee cores are provided with suitable coatings which, if desired, are resistant to gastric juices. For this purpose, concentrated saccharide solutions may be used, which may optionally contain gum arabic, talc, polyvinyl pyrrolidone, poly(ethylene glycol) and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, can be used. Dye stuffs or pigments may be added to the tablets or dragee coatings, for example, for identification or in order to characterize combinations of active ingredients or doses thereof.

Suitable formulations for oral and/or parenteral administration include aqueous solutions of one or more of the compounds of the invention, and optionally one or more additional active pharmaceutical ingredients, in water-soluble form, for example, water-soluble salts and alkaline solutions. In addition, suspensions of the active ingredient(s) as appropriate oily injection suspensions may be administered. Suitable lipophilic solvents or vehicles include fatty oils, for example, sesame oil, or synthetic fatty acid esters, for example, ethyl oleate or triglycerides or poly(ethylene glycol)-400. Aqueous injection suspensions may optionally also comprise substances which increase the viscosity of the suspension including, for example, sodium carboxymethyl cellulose, sorbitol, and/or dextran. Optionally, the suspension may also contain one or more stabilizers, one or more preservatives (e.g., sodium edetate, benzalkonium chloride, and the like), and/or other components commonly used in formulating pharmaceutical compositions.

Inhibitors of LRP-1 can be optionally combined with or administered in concert with each other or other agents known to be useful in the treatment of the relevant disease or condition. In various embodiments, the inhibitor of LRP-1 is co-administered with an anti-inflammatory agent. Exemplary anti-inflammatory agents for co-administration include without limitation non-steroidal anti-inflammatory drugs (NSAID), e.g., aspirin, acetaminophen, diclofenac potassium, diclofenac sodium, diclofenac sodium with misoprostol, diflunisal, etodolac, fenoprofen calcium, flurbiprofen, ibuprofen, indomethacin, ketoprofen, meclofenamate sodium, mefenamic acid, meloxicam, nabumetone, naproxen sodium, piroxicam, tolmetin sodium, magnesium salicylate, choline salicylate, salsalate, sodium salicylate, alkyl salicylate and disalicylate. In some embodiments, the co-administered NSAID is a selective inhibitor of COX-2. In some embodiments, the selective inhibitor of COX-2 is selected from the group consisting of celecoxib, valdecoxib, lumiracoxib, etoricoxib, and rofecoxib.

In some embodiments, an inhibitory nucleic acid that specifically inhibits the expression of LRP-1 is administered. Inhibitory nucleic acids, such as siRNA, shRNA, ribozymes, or antisense molecules, can be synthesized and introduced into cells using methods known in the art. Molecules can be synthesized chemically or enzymatically in vitro (Micura, Agnes Chem. Int. Ed. Emgl. 41: 2265-9 (2002); Paddison et al., Proc. Natl. Acad. Sci. USA, 99: 1443-8 2002) or endogenously expressed inside the cells in the form of shRNAs (Yu et al., Proc. Natl. Acad. Sci. USA, 99: 6047-52 (2002); McManus et al., RNA 8, 842-50 (2002)). Plasmid-based expression systems using RNA polymerase III U6 or H1, or RNA polymerase II U1, small nuclear RNA promoters, have been used for endogenous expression of shRNAs (Brummelkamp et al., Science, 296: 550-3 (2002); Sui et al., Proc. Natl. Acad. Sci. USA, 99: 5515-20 (2002); Novarino et al., J. Neurosci., 24: 5322-30 (2004)). Synthetic siRNAs can be delivered by electroporation or by using lipophilic agents (McManus et al., RNA 8, 842-50 (2002); Kishida et al., J. Gene Med., 6: 105-10 (2004)). Alternatively, plasmid systems can be used to stably express small hairpin RNAs (shRNA) for the suppression of target genes (Dykxhoorn et al., Nat. Rev. Mol. Biol., 4: 457-67 (2003)). Various viral delivery systems have been developed to deliver shRNA-expressing cassettes into cells that are difficult to transfect (Brummelkamp et al., Cancer Cell, 2: 243-7 (2002); Rubinson et al., Nat. Genet., 33: 401-6 2003). Furthermore, siRNAs can also be delivered into live animals. (Hasuwa et al., FEBS Lett., 532, 227-30 (2002); Carmell et al., Nat. Struct. Biol., 10: 91-2 (2003); Kobayashi et al., J. Pharmacol. Exp. Ther., 308: 688-93 (2004)).

Inhibitory oligonucleotides can be delivered to a cell by direct transfection or transfection and expression via an expression vector. Appropriate expression vectors include mammalian expression vectors and viral vectors, into which has been cloned an inhibitory oligonucleotide with the appropriate regulatory sequences including a promoter to result in expression of the antisense RNA in a host cell. Suitable promoters can be constitutive or development-specific promoters. Transfection delivery can be achieved by liposomal transfection reagents, known in the art (e.g., Xtreme transfection reagent, Roche, Alameda, Calif.; Lipofectamine formulations, Invitrogen, Carlsbad, Calif.). Delivery mediated by cationic liposomes, by retroviral vectors and direct delivery are efficient. Another possible delivery mode is targeting using antibody to cell surface markers for the target cells.

For transfection, a composition comprising one or more nucleic acid molecules (within or without vectors) can comprise a delivery vehicle, including liposomes, for administration to a subject, carriers and diluents and their salts, and/or can be present in pharmaceutically acceptable formulations. Methods for the delivery of nucleic acid molecules are described, for example, in Gilmore, et al., Curr Drug Delivery (2006) 3:147-5 and Patil, et al., AAPS Journal (2005) 7: E61-E77, each of which are incorporated herein by reference. Delivery of siRNA molecules is also described in several U.S. Patent Publications, including for example, 2006/0019912; 2006/0014289; 2005/0239687; 2005/0222064; and 2004/0204377, the disclosures of each of which are hereby incorporated herein by reference. Nucleic acid molecules can be administered to cells by a variety of methods known to those of skill in the art, including, but not restricted to, encapsulation in liposomes, by iontophoresis, by electroporation, or by incorporation into other vehicles, including biodegradable polymers, hydrogels, cyclodextrins (see, for example Gonzalez et al., 1999, Bioconjugate Chem., 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and U.S. Patent Publication No. 2002/130430), biodegradable nanocapsules, and bioadhesive microspheres, or by proteinaceous vectors (O'Hare and Normand, International PCT Publication No. WO 00/53722). In another embodiments, the nucleic acid molecules can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

Examples of liposomal transfection reagents of use with this invention include, for example: CellFectin, 1:1.5 (M/M) liposome formulation of the cationic lipid N,NI,NII,NIII-tetramethyl-N,NI,NII,NIII-tetrapalmit-y-spermine and dioleoyl phosphatidylethanolamine (DOPE) (GIBCO BRL); Cytofectin GSV, 2:1 (M/M) liposome formulation of a cationic lipid and DOPE (Glen Research); DOTAP (N-[1-(2,3-dioleoyloxy)-N,N,N-tri-methyl-ammoniummethylsulfate) (Boehringer Manheim); Lipofectamine, 3:1 (M/M) liposome formulation of the polycationic lipid DOSPA and the neutral lipid DOPE (GIBCO BRL); and (5) siPORT (Ambion); HiPerfect (Qiagen); X-treme GENE (Roche); RNAicarrier (Epoch Biolabs) and TransPass (New England Biolabs).

In some embodiments, antisense, siRNA, or ribozyme sequences are delivered into the cell via a mammalian expression vector. For example, mammalian expression vectors suitable for siRNA expression are commercially available, for example, from Ambion (e.g., pSilencer vectors), Austin, Tex.; Promega (e.g., GeneClip, siSTRIKE, SiLentGene), Madison, Wis.; Invitrogen, Carlsbad, Calif.; InvivoGen, San Diego, Calif.; and Imgenex, San Diego, Calif. Typically, expression vectors for transcribing siRNA molecules will have a U6 promoter.

In some embodiments, antisense, siRNA, shRNA or ribozyme sequences are delivered into cells via a viral expression vector. Viral vectors suitable for delivering such molecules to cells include adenoviral vectors, adeno-associated vectors, and retroviral vectors (including lentiviral vectors). Neurotropic viral vectors find use. For example, viral vectors developed for delivering and expressing siRNA oligonucleotides are commercially available from, for example, GeneDetect, Bradenton, Fla.; Ambion, Austin, Tex.; Invitrogen, Carlsbad, Calif.; Open BioSystems, Huntsville, Ala.; and Imgenex, San Diego, Calif.

4. Screening for Agents

In a further aspect, the invention provides methods of identifying an agent for use in for increasing, promoting or enhancing neurite outgrowth and/or axonal regeneration and/or inhibiting degeneration of a neuron, the method comprising: (a) contacting a neuronal cell with a candidate agent; (b) determining a level of LRP-1 function; and (c) measuring the level of neurite outgrowth. Candidate agents of interest reduce or inhibit LRP-1 function and increase the level of neurite growth of the neuronal cell.

In some embodiments, the candidate agent is a small organic compound, a polypeptide, an antibody or fragment thereof, an amino acid or analog thereof, a carbohydrate, a saccharide or disaccharide, or a polynucleotide.

The screening methods of the invention can be conveniently carried out using high-throughput methods. In some embodiments, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int J Pept Prot Res 37: 487-493 (1991) and Houghton, et al., Nature 354:84-88 (1991)). Other chemistries for generating chemical diversity libraries can also be used. Such chemistries include, but are not limited to peptoids (e.g., PCT Publication No. WO 91/19735), encoded peptides (e.g., PCT Publication WO 93/20242), random bio-oligomers (e.g., PCT Publication No WO 92/00091), benzodiazepines (e.g., U.S. Pat. No. 5,288,514), diversomers such as hydantoins, benzodiazepines and dipeptides (Hobbs, et al, Proc Nat Acad Sci USA 90:6909-6913 (1993)), vinylogous polypeptides (Hagihara, et al., J Amer Chem Soc 114:6568 (1992)), nonpeptidal peptidomimetics with glucose scaffolding (Hirschmann, et al., J Amer Chem Soc 114:9217-9218 (1992)), analogous organic syntheses of small compound libraries (Chen, et al., J Amer Chem Soc 116:2661 (1994)), oligocarbamates (Cho, et al., Science 261:1303 (1993)) and/or peptidyl phosphonates (Campbell, et al., J Org Chem 59:658 (1994)), nucleic acid libraries, peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang, et al., Science 274:1520-1522 (1996) and U.S. Pat. No. 5,593,853), small organic molecule libraries (see, e.g., benzodiazepines, Baum, C&EN, January 18, page 33 (1993), isoprenoids, U.S. Pat. No. 5,569,588), thiazolidinones and metathiazanones, U.S. Pat. No. 5,549,974 pyrrolidines, U.S. Pat. Nos. 5,525,735 and 5,519,134, morpholino compounds, U.S. Pat. No. 5,506,337 benzodiazepines, U.S. Pat. No. 5,288,514, and the like).

Devices for the preparation of combinatorial libraries are commercially available (see, e.g., 357 MPS, 390 MPS, Advanced Chem Tech. Louisville Ky.; Symphony, Rainin, Woburn, Mass.; 433A Applied Biosystems, Foster City, Calif.; 9050 Plus, Millepore, Bedford. Mass.). In addition, numerous combinatorial libraries are themselves commercially available (see, e.g., ComGenex, Princeton, N.J.; Tripos, Inc, St Louis, Mo.; 3D Pharmaceuticals, Eaton, Pa.; Martek Biosciences, Columbia, Md.). Libraries of FDA approved compounds are commercially available and find use (e.g., from Enzo Life Sciences (enzolifesciences.com); and Microsource Discovery Systems (msdiscovery.com)). Chemical libraries with candidate agents selected for bioavailability and blood-brain barrier penetration also find use, and are commercially available, e.g., from ChemBridge (chembridge.com) and Prestwick Chemical (prestwick-chemical.fr). Further libraries of chemical agents that find use are available, e.g., from Evotec (evotec.com); Magellan Bio-Science Group (magellanbioscience.com); and Cellumen (cellumen.com).

In high throughput assays of the invention, it is possible to screen up to several thousand different candidate agents in a single day. In particular, each well of a microtiter plate can be used to run a separate assay against a selected potential candidate agent, or, if concentration or incubation time effects are to be observed, every 5-10 wells can test a single modulator. Thus, a single standard microtiter plate can assay about 100 (e.g., 96) candidate agents. Multiwell plates with greater numbers of wells find use, e.g., 192, 384, 768 or 1536 wells. If 1536-well plates are used, then a single plate can easily assay from about 100 to about 1500 different compounds. It is possible to assay several different plates per day. Assay screens for up to about 6,000-20,000 different compounds are possible using the integrated systems of the invention.

EXAMPLES

The following examples are offered to illustrate, but not to limit the claimed invention.

Example 1

LRP1 is a Neuronal MAG Receptor that is Required for RhoA Activation and Inhibition of Neurite Outgrowth Experimental Procedures Recombinant and Purified Proteins. CII, which includes amino acids 804-1185 in the structure of mature human LRP1, CIV, which includes amino acids 3331-3778, and full length rat MAG, were cloned into pFuse-rFC2 (Invivogen, San Diego, Calif.) and expressed as Fc fusion proteins in CHO-K1 cells. Fc fusion proteins were purified from conditioned culture medium by affinity chromatography on Protein A-Sepharose (GE Healthcare). GST-RAP and GST were expressed in bacteria and purified as previously described (Gaultier et al (2009). *J Cell Sci* 122, 1155-1162). Shed LRP1 was purified from human plasma by RAP-affinity chromatography and molecular exclusion chromatography, as previously described (Gorovoy et al., (2010). *J Leukoc Biol* 88:769-778). Full-length LRP1 was purified from rat liver, as described by Gorovoy et al. (Gorovoy et al., 2010, supra). Homogeneity and integrity of LRP1 preparations were determined by SDS-PAGE.

Cell Culture. CHO cells were cultured in high glucose Dulbecco's Modified Eagle's Medium (DMEM) with 10% fetal bovine serum (FBS, Hyclone), 10 mg/L L-glutamine, and 10 mg/L non-essential amino acid solution (Gibco). For expression of recombinant proteins, transfected CHO cells were cultured in Power-CHO CD media (Lonza). MAG-expressing and R2 CHO cells were a generous gift from Dr. Mark Tuszynski (University of California San Diego). These cells were maintained in DMEM with 10% FBS, 2 mM glutamine, 40 mg/L proline, 0.73 mg/L thymidine, 1 μM methotrexate, 7.5 mg/L glycine and 50 μg/ml G418 (Gibco). Rat PC12 pheochromocytoma cells were obtained from the ATCC and cultured in DMEM with 10% FBS, 5% heat-inactivated horse serum (Hyclone), and penicillin/streptomycin (P/S, Hyclone). In neurite outgrowth experiments, PC12 cells were plated in serum-free medium (SFM) and then treated with 50 μg/ml NGF-β (R&D Systems). Mouse N2a neuroblastoma cells were a generous gift from Dr. Katerina Akassoglou (Gladstone Institute of Neurological Disease, University of California San Francisco). N2a cells were cultured in DMEM with 10% FBS and P/S. For neurite outgrowth experiments, cells were plated in SFM. Primary cultures of CGNs were isolated as previously described (Oberdoerster, (2001). Isolation of Cerebellar Granule Cells from Neonatal Rats (John Wiley & Sons)) and cultured in DMEM with 50 mM glucose, 10% FBS, 25 mM KCl, and P/S. N20.1 cells were a generous gift from Dr. Anthony Campagnoni (University of California, Los Angeles) and were cultured as previously described (Wight and Dobretsova (1997). *Gene* 201:111-117).

LRP1 gene-silencing. PC12 cells and CGNs were transfected with the previously described rat LRP1-specific siRNA (CGAGCGACCUCCUAUCUUUUU (SEQ ID NO: 9)) from Dharmacon or with NTC siRNA using the Amaxa rat neuron nucleofector kit, according to the manufacturer's instructions. LRP1 was silenced in N2a cells using ON-TARGET plus, smart-pool LRP1-specific siRNA (Thermo Scientific) and Lipofectamine 2000 (Invitrogen). Stable LRP1 gene-silencing was achieved in N2a cells using our previously described LRP1-specific shRNA, cloned into pSUPER (Oligoengine) (Gaultier et al., (2010). J Proteome Res 9:6689-6695). This construct or empty vector was transfected into N2a cells using Lipofectamine 2000. Transfected cells were selected with puromycin (1 μg/mL) and then for 48 h with Pseudomonas Exotoxin A (200 ng/ml, List Biological Laboratories), which is selectively lethal towards LRP1-expressing cells (FitzGerald et al., (1995). *J Cell Biol* 129:1533-1541). LRP1 gene-silencing was confirmed by RT-PCR and by immunoblot analysis.

CNS Myelin Purification. Myelin vesicles were purified from mouse and rat brain, as described by Norton and Poduslo (Norton and Poduslo, (1973). *J Neurochem* 21:749-757; Gaultier et al., 2009, supra). In brief, adult rodent brains were homogenized in 0.32 M sucrose, layered over 0.085 M sucrose and subjected to sucrose density gradient ultracentrifugation. The myelin was subject to osmotic shock, recovered, and re-suspended in 20 mM sodium phosphate, 150 mM NaCl, pH 7.4 (PBS). The purity of the preparation was determined by Coomassie Blue-staining and by immunoblot analysis for myelin basic protein, as previously described (Gaultier et al., 2009).

Mass Spectrometry. Myelin-associated proteins were solubilized from purified myelin vesicles with RIPA buffer (100 mM Tris-HCl, 150 mM NaCl, 1% Triton X100, 0.5% deoxycholate, 0.1% SDS supplemented with 1 mM $CaCl_2$ and proteases inhibitors). Protein extracts (2 mg) were incubated with 1 μM CII-Fc, CIV-Fc, or Fc overnight at 4° C. The fusion proteins and associated proteins were recovered by incubation with Protein A-Sepharose for 1 h at 20° C. After extensive washing with RIPA buffer, proteins were digested with trypsin in the presence of ProteaseMAX surfactant as described by the manufacturer (Promega). Proteins that were associated with CII-Fc or CIV-Fc, and not with Fc were identified as "specific interacters" by LC-$MS^2$ as previously described (Gaultier et al., (2010). *J Proteome Res* 9, 6689-6695)

Protein-Binding Experiments. Unless otherwise specified, cell extracts were prepared in 50 mM HEPES pH 7.4, 1% Triton X-100, 150 mM NaCl, 10% glycerol, protease inhibitor cocktail, 2 mM EDTA, 1 mM sodium orthovanadate. In affinity precipitation studies, CII-Fc, CIV-Fc or MAG-Fc was immobilized on Protein A-Sepharose prior to adding potential ligands. MAG was identified in affinity precipitates by immunoblot analysis using MAG-specific antibody from R&D systems. LRP1 was detected using antibody from Sigma.

LRP1 was affinity precipitated using LRP1-specific antibody coupled to Protein A-Sepharose, following by a preclear step with non-immune IgG. p75NTR was detected using an antibody that detects the intracellular domain (Millipore).

In dot blotting studies, 1.0 μg of CII-Fc, CIV-Fc or Fc was immobilized on nitrocellulose that was secured in Bio-Rad bio-dot apparatus. The membrane was blocked with 5% bovine serum albumin (BSA) in PBS. Incubations with MAG-Fc (5 μg/ml) were conducted for 1 h at 22° C. The membranes were then washed and immunoblotted for MAG.

RhoA Activation. N2a cells were cultured for 1 day and then serum-starved for 1 h. MAG-Fc or Fc were pre-incubated with Fc-specific antibody (Jackson Immunoresearch Laboratories) at a 2:1 molar ratio and added to N2a cells (20 nM) for 10 min. Fc-specific antibody blocks availability of the Fc domain to cells but also presents two MAG units in close proximity to the cell. Cell extracts were prepared and GTP-loaded RhoA was affinity-precipitated using the Rho binding domain of Rhotekin, which was expressed as a GST fusion protein, according to the manufacturer's instructions (Millipore). Affinity-precipitated active RhoA and total RhoA were determined by immunoblot analysis using RhoA antibody from Cell Signaling. In experiments using TAT-pep5 (EMD Bioscience), cells were incubated with 500 nM TAT-pep5 or vehicle for 30 min prior to adding MAG-Fc.

Neurite Outgrowth Experiments. MAG-expressing and R2 CHO cells were cultured on glass slides as previously described (Domeniconi et al., 2002). When the CHO cell cultures were confluent, CGNs, PC 12 cells, or N2a cells were added and allowed to differentiate for 48 h, unless otherwise specified. As an alternative to the CHO cell model system, glass slides were coated with type I collagen (25 μg/ml) or PDL (50 μg/ml) and then, in some cases, over-coated with 8 μg/ml purified myelin in 30 μM HEPES, pH 7.4 and allowed to dry overnight. When GST-RAP or GST was added, these proteins were pre-incubated with the neurite-generating cells in suspension for 15 min prior to plating. Shed LRP1 was pre-incubated with the myelin substratum. Neurite outgrowth was determined by im-munofluorescence microscopy to detect βIII-tubulin and quantitated using ImageJ or Metamorph software.

MAG Internalization. MAG-Fc was radioiodinated by incubation using 1 mCi of $Na^{125}I$ using Iodobeads (Pierce) and separated from free $Na^{125}I$ by molecular exclusion chromatography. $1\times10^5$ cells were plated in 12-well plates. Cells were washed twice and then equilibrated in DMEM with 25 mM Hepes, pH 7.4, 0.1% BSA and Fc-Blocker (BD Biosciences). $^{125}I$-MAG-Fc (25 nM) was incubated with cells for 2 h at 37° C. Unlabeled MAG (1.25 μM) was added to some wells. At the end of the incubation, cells were washed and treated with 0.25% Pronase (Roche) for 15 min to eliminate surface-associated $^{125}I$-MAG-Fc. Cell extracts were prepared in 0.1 M NaOH and 1% SDS. Cell-associated radioactivity was determined using a Wallac 1470 Wizard Gamma Counter (Perkin Elmer). Cellular protein was determined by bicinchoninic acid assay (Pierce). Specific MAG-Fc uptake was calculated as the fraction of total uptake that was inhibited by excess unlabeled MAG.

Data Analysis. Data processing and statistical analysis were performed using GraphPad Prism (Graph-Pad Software Inc.). Data sets were analyzed by one-way ANOVA with Tukey's post-hoc test or by Student's t-test. P-values <0.05 were considered statistically significant.

Results

LRP1 is an Independent, Endocytic Receptor for MAG

To screen for myelin-associated proteins that bind to LRP1, we expressed the second and fourth clusters of complement-like repeats (CII and CIV), which are responsible for most ligand-binding events in intact LRP1 (Willnow et al., (1994). *J Biol Chem* 269:15827-15832; Strickland et al., (2002). *Trends Endocrinol Metab* 13:66-74), as separate Fc-fusion proteins (FIG. 1A). Myelin vesicles were purified from mouse brain as previously described (Gaultier et al., 2009, supra), solubilized in Triton X-100, and incubated with CII-Fc and CIV-Fc. Binding partners for the Fc-fusion proteins were identified by LC-MS/MS, as previously described (Gaultier et al., 2010, supra). In experiments with CII-Fc and CIV-Fc but not Fc (the negative control), MAG was identified as an abundant binding partner (FIG. 2). To validate our LC-MS/MS result, pull-down experiments were performed with CII-Fc and CIV-Fc, which were immobilized on Protein A-Sepharose. FIG. 1B shows that MAG in purified rat myelin bound to CII-Fc and CIV-Fc, but not Fc (the negative control). Purified MAG also bound to CII-Fc and CIV-Fc, immobilized on nitrocellulose (FIG. 1C). Binding of purified MAG to CII-Fc and CIV-Fc confirms that the interaction is direct and not mediated through an intermediate protein present in rat myelin.

Figure 1D:
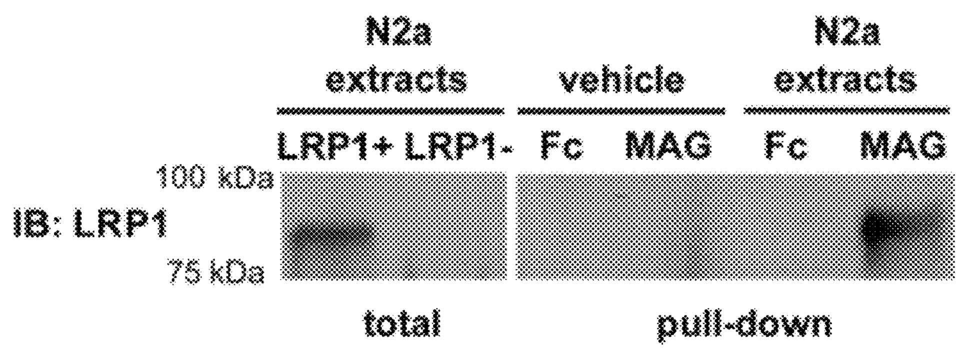
Figure 1E:
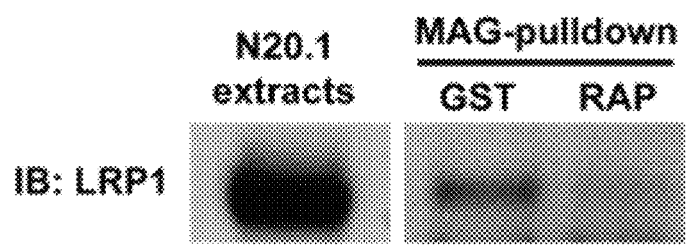
Figure 1F:
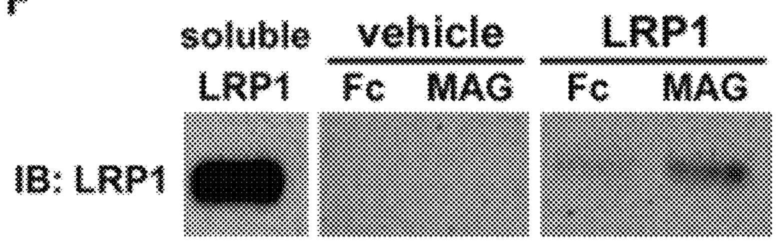

To confirm that MAG binds to full-length LRP1, we prepared extracts from N2a neuroblastoma cells. FIG. 1D shows that N2a cells express LRP1 and that expression is silenced by stable transfection with LRP1-specific shRNA. LRP1 in N2a cell extracts bound to MAG-Fc, which was immobilized on Protein A-Sepharose. Binding was specific because LRP1 failed to associate with immobilized Fc. We confirmed that MAG binds to full-length LRP1 using extracts of a second cell line, N20.1 oligodendroglial cells. Binding of MAG to LRP1 in extracts of N20.1 cells was blocked by receptor-associated protein (RAP) (FIG. 1E), an LRP1 chaperone which binds directly to LRP1 and inhibits binding of other known LRP1 ligands (Williams et al., (1992). *J Biol Chem* 267:9035-9040; Strickland et al., 2002, supra). Next, we purified full-length LRP1 from rat liver, as previously described (Gorovoy et al., 2010, supra). Purified rat LRP1 bound to MAG-Fc (FIG. 1F), indicating that the interaction is direct and not mediated by other proteins in cell extracts. Finally, because LRP1 is an endocytic receptor, we tested the role of LRP1 in MAG endocytosis. LRP1-expressing N2a cells demonstrated specific internalization of $^{125}I$-labeled MAG-Fc (defined as the fraction of internalization inhibited by a 50-fold molar excess of unlabeled MAG-Fc). In three separate experiments, cells that were incubated with 25 nM $^{125}I$-

Figure 1G:
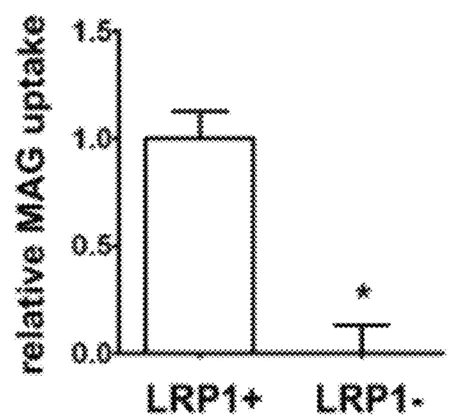

MAG-Fc internalized 44 fmol MAG-Fc/mg cell protein per hour. LRP1 gene-silencing inhibited specific internalization of $^{125}$I-MAG-Fc by 102±8% (FIG. 1G). Thus, in N2a cells, LRP1 is the principal receptor responsible for MAG endocytosis.

LRP1 is Required for Inhibition of Neurite Outgrowth by MAG and Purified Myelin

Figure 3:
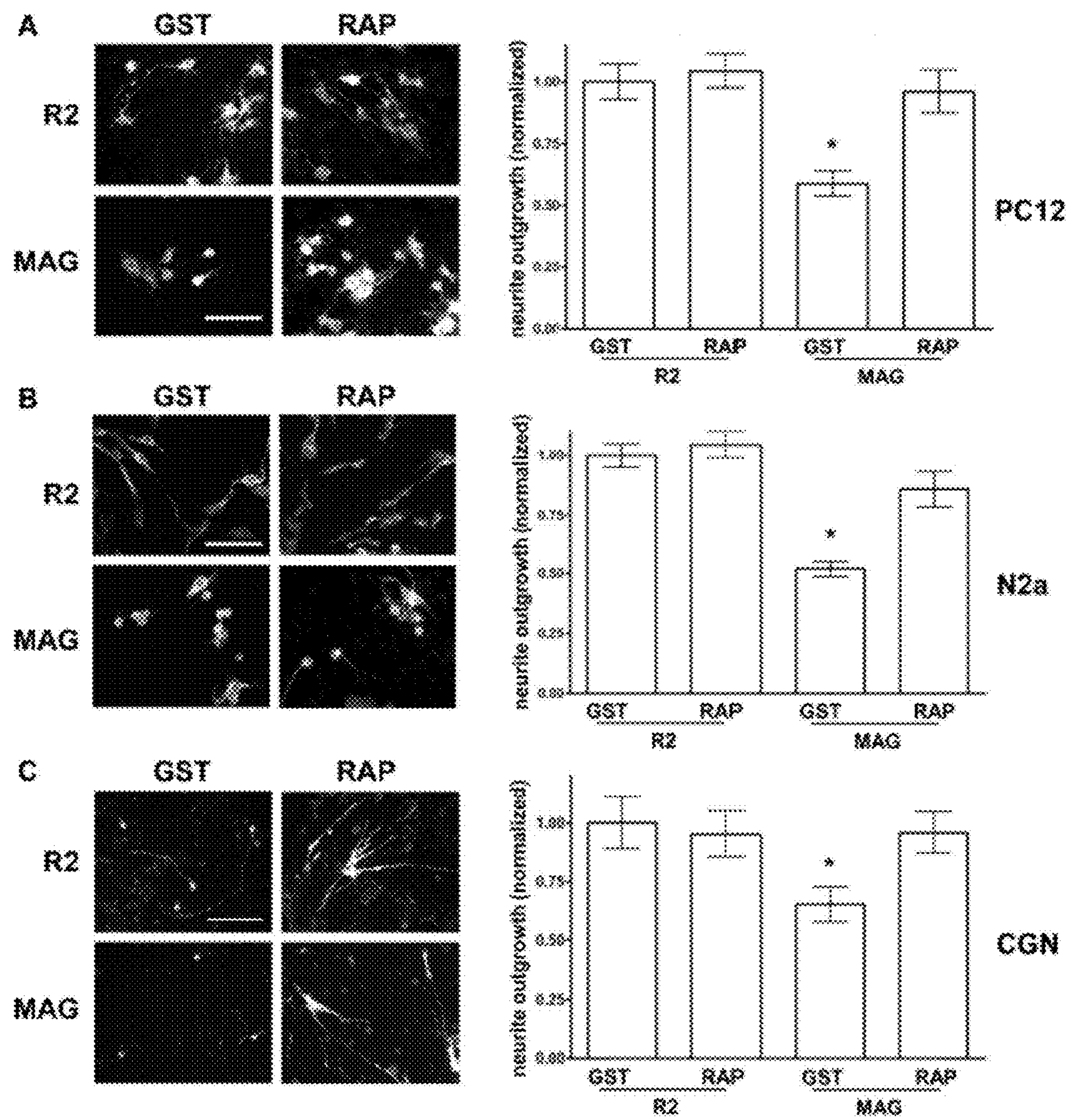
FIGS. 3A-3C illustrate that LRP1 antagonism with RAP restores neurite outgrowth on MAG-expressing CHO cells (A) PC12 cells, (B) N2a cells, and (C) CGNs were plated on R2 control, or MAG-expressing CHO cells and allowed to differentiate for 48 h in the presence of GST-RAP or GST (200 nM). Neurite outgrowth was detected by immunofluorescent imaging of βIII-tubulin. Results were normalized against those obtained when cells were plated on R2 cells in the presence of GST. In control experiments, we confirmed that GST does not affect neurite outgrowth (*, $p<0.05$).

PC12 cells, N2a cells, and primary cultures of rat cerebellar granule neurons (CGNs) were cultured on a monolayer of CHO cells that express membrane-bound MAG or on control R2 cells, which do not express MAG (Collins et al., *J Biol Chem* (1997) 272:1248-1255; Domeniconi et al., (2002). *Neuron* 35:283-290.). In experiments with all three cell types, neurite outgrowth was significantly inhibited by the MAG-expressing cells (FIG. 3). When RAP (200 nM) was added to the cultures, to block ligand-binding to LRP1, inhibition of neurite outgrowth by the MAG-expressing cells was reversed. Because RAP is expressed as a GST-fusion protein, as a control, we added 200 nM GST, which did not affect neurite outgrowth.

Figure 4:
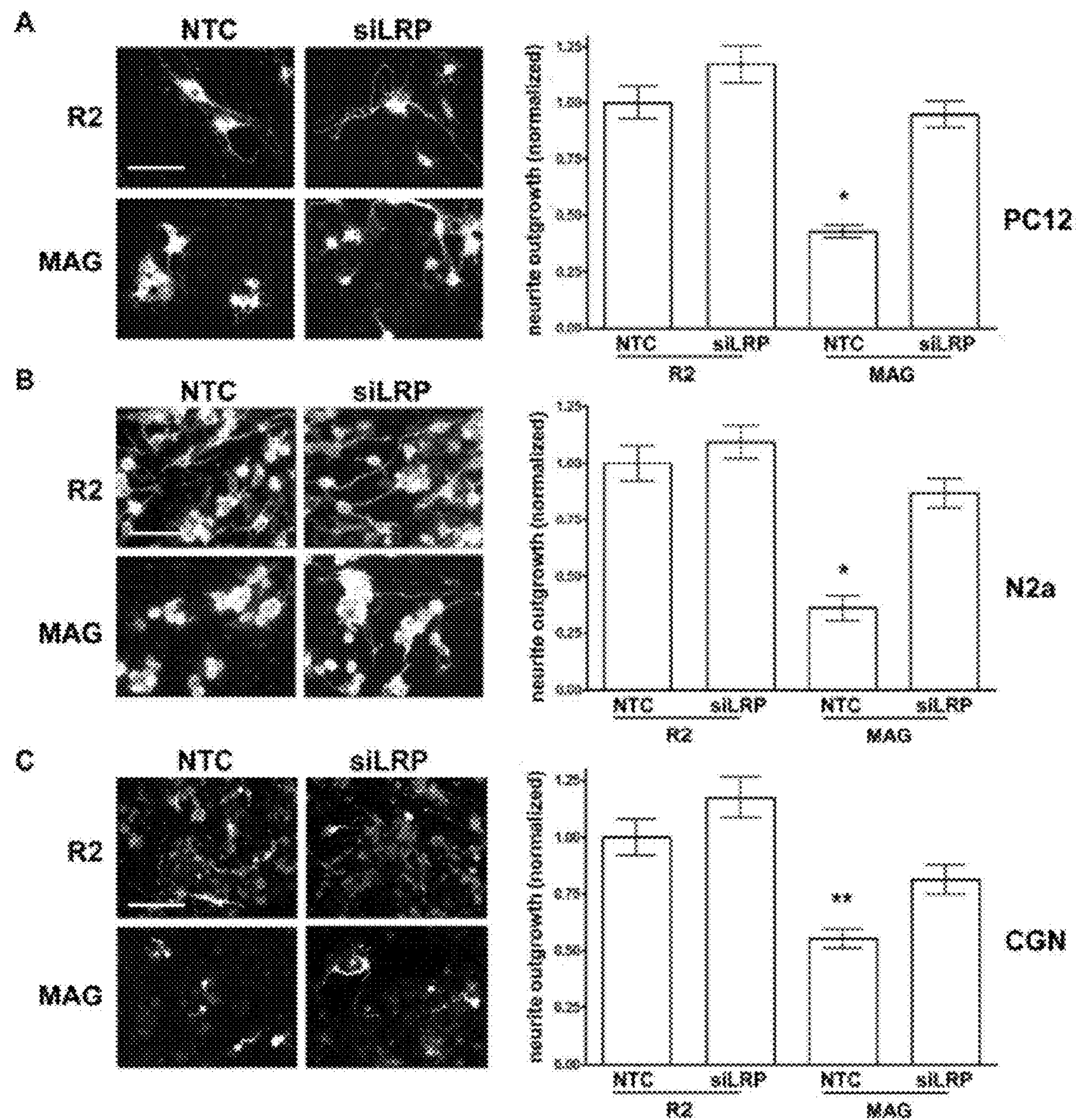
FIG. 4A-4C illustrate that LRP1 gene-silencing restores neurite outgrowth on MAG-expressing CHO cells (A) PC12 cells, (B) N2a cells, and (C) CGNs were transfected with LRP1-specific siRNA (siLRP) or with NTC siRNA. Cells were plated on R2 control or MAG-expressing CHO cells and allowed to differentiate for 48 h. Neurite outgrowth was detected by immune-fluorescent imaging of βIII-tubulin. Results were normalized against those obtained when cells were transfected with NTC siRNA and plated on R2 cells (*, $p<0.05$; **, $p<0.01$).
Figure 5:
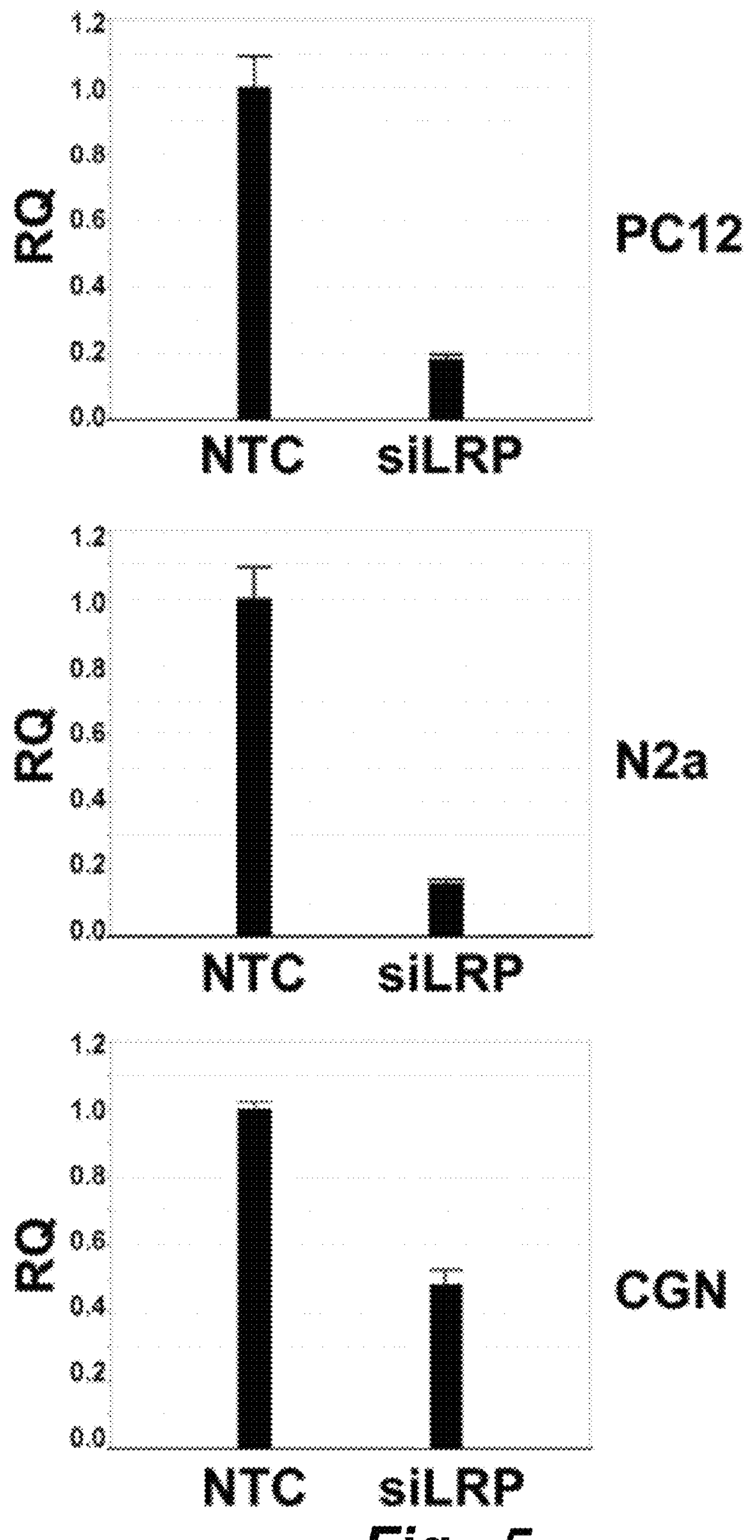
FIG. 5 illustrates the extent of LRP1 expression in our silencing experiments.

To confirm that the effects of RAP on neurite outgrowth were due to LRP1 neutralization, we silenced LRP1 gene expression in PC12 cells, N2a cells, and CGNs. LRP1 gene silencing was confirmed by RT-PCR (FIG. 5). Control cells were transfected with non-targeting control (NTC) siRNA. FIG. 4 shows that LRP1 gene-silencing significantly reversed the effects of MAG-expressing CHO cells on neurite outgrowth in all three cell types, proportional to the degree of LRP1 gene-silencing. These results suggest that LRP1 is essential for inhibition of neurite outgrowth by MAG.

Figure 6:
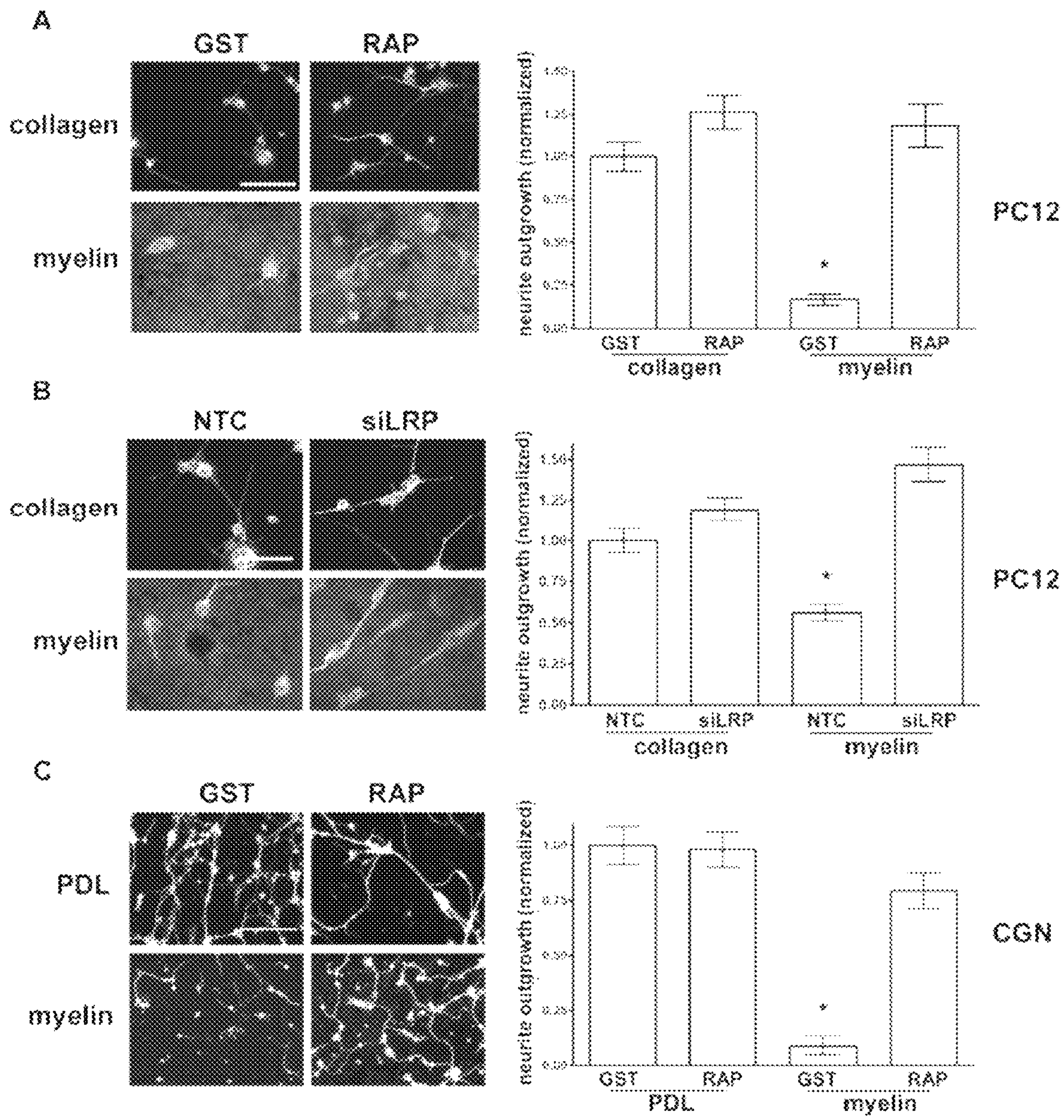
FIGS. 6A-6C illustrate that LRP1 inactivation restores neurite outgrowth on purified myelin (A) PC12 cells were pre-treated with 200 nM GST-RAP or GST and plated on type I collagen or purified myelin. Differentiation was allowed to occur for 48 h. (B) PC12 cells were transfected with LRP1-specific or NTC siRNA and plated on type I collagen or purified myelin. Differentiation was allowed to occur for 48 h. (C) CGNs pre-treated with GST-RAP or GST, plated on purified myelin or PDL, and allowed to differentiate for 48 h. CGNs were imaged by immunofluorescent detection of βIII-tubulin. Neurite out-growth was quantitated by Metamorph software and normalized against that observed when CGNs were plated on PDL and treated with GST (*, $p<0.01$).
Figure 7:
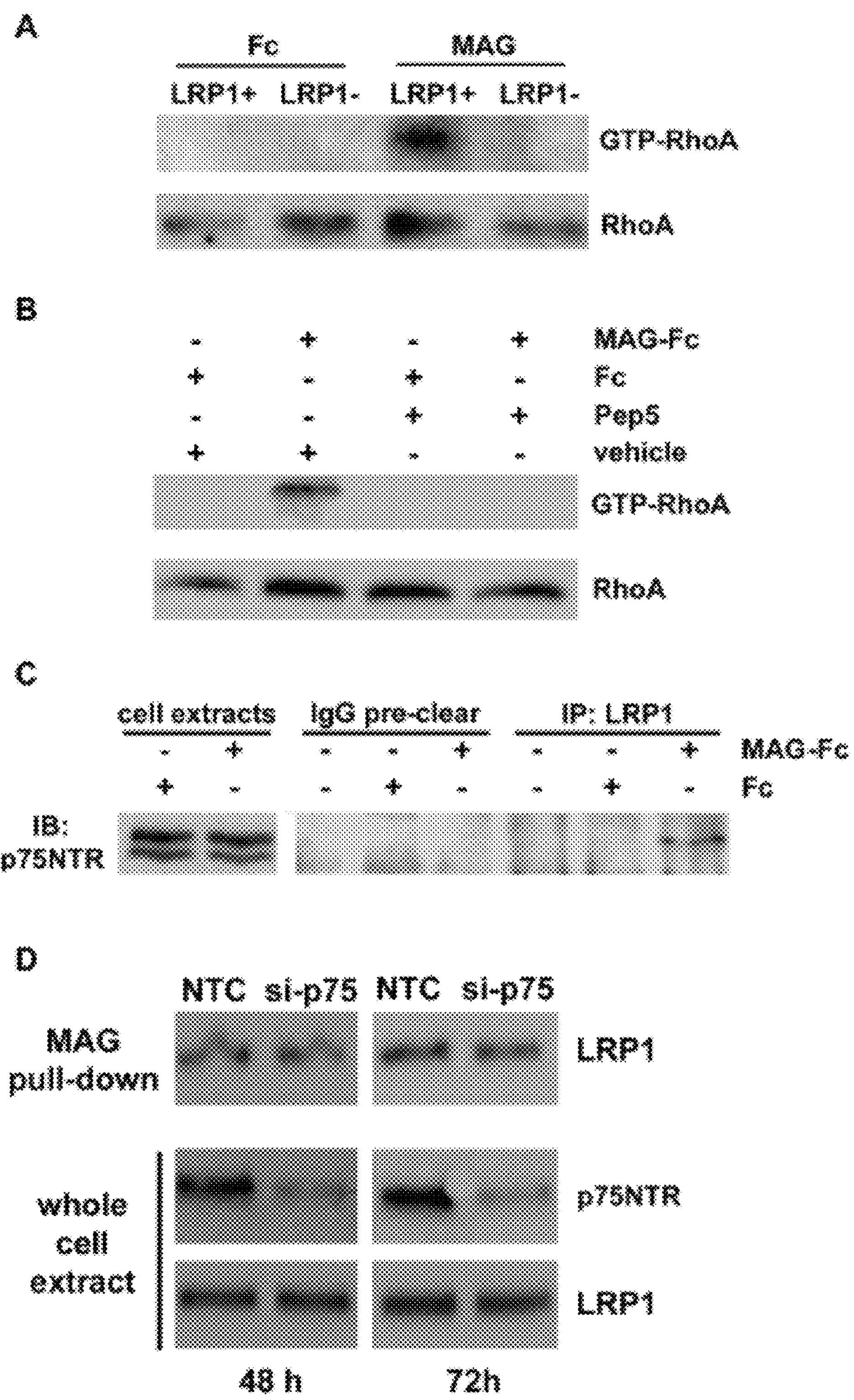
FIGS. 7A-7D illustrate that LRP1 and p75NTR are required for MAG-mediated RhoA activation (A) N2a cells in which LRP1 was silenced with shRNA and LRP1-expressing N2a cells were treated with MAG-Fc or Fc (20 nM). GTP-RhoA was determined by GST-RBD pull-down. Total RhoA was determined by analysis of whole cell extracts without affinity precipitation. (B) N2a cells were pre-treated with TAT-pep5, which blocks the activity of p75NTR, or vehicle. The cells were then treated with MAG-Fc or Fc (20 nM). GTP-loaded and total RhoA were determined. (C) N2a cells were treated with 20 nM MAG-Fc or Fc, extracted, and subject to sequential immunoprecipitation with control IgG and then LRP1-specific antibody. Precipitated proteins were subjected to SDS-PAGE and immunoblot analysis for p75NTR. Whole cell extracts from N2a cells are shown in the left-hand lanes. (D) N20.1 cells were transfected with p75NTR-specific or NTC siRNA and analyzed 48 or 72 h after introducing the siRNA. Affinity co-precipitation of LRP1 with MAG-Fc from cell extracts was unchanged by p75NTR gene-silencing. Whole cell extracts were subjected to immunoblot analysis to detect p75NTR and LRP1.

Because myelin contains proteins that inhibit neurite outgrowth and axonal regeneration in addition to MAG, we examined neurite outgrowth in cells plated on immobilized myelin, which was purified from rat brain. Control cells were plated on glass slides that were pre-coated with either type 1 collagen or poly-D-lysine (PDL). FIG. 6 shows that myelin significantly decreased neurite outgrowth in PC12 cells and this effect was substantially reversed by RAP (panel A) or by LRP1 gene-silencing (panel B). Purified myelin also robustly inhibited axonal outgrowth in CGNs (FIG. 7C). RAP effectively antagonized the inhibitory activity of myelin, restoring axonal outgrowth in CGNs to nearly the level observed when the cells were plated on PDL.

MAG-Binding to LRP1 Recruits p75NTR and Activates RhoA

RhoA activation is critical in the pathway by which myelin-associated proteins inhibit neuronal regeneration (Yamashita et al., (2002). *J Cell Biol* 157:565-570; Kozma et al., (1997). *Mol Cell Biol* 17:1201-1211; Kuhn et al., (1999). *J Neurosci* 19: 1965-1975; Madura et al., (2004). *EMBO reports* 5:412-417). Blocking RhoA activation promotes neurite outgrowth (Jalink et al., (1994). *J Cell Biol* 126:801-810; Jeon et al., *J Neurochem* (2012) 120(5):684-98) even when cells are plated on inhibitory substrata (Niederost et al., (2002). *J Neurosci* 22:10368-10376.; Fu et al., (2007). *J Neurosci* 27:4154-4164; Tan et al., (2007) Pharmaceutical Research 24: 2297-2308). We examined the activity of LRP1 in MAG-induced RhoA activation. N2a cells in which LRP1 was silenced with shRNA were compared with control cells that were transfected with empty vector. As shown in FIG. 7A, MAG-Fc substantially increased GTP-loaded RhoA in LRP1-expressing N2a cells, whereas Fc did not. When LRP1 was silenced, MAG-Fc failed to increase GTP-loaded RhoA. Thus, LRP1 was essential for RhoA activation by MAG-Fc. In control experiments, we demonstrated that N2a cell survival and differentiation in response to serum starvation were unchanged by LRP1 gene-silencing with shRNA.

p75NTR has been implicated in RhoA activation in response to myelin-associated proteins (Wong et al., (2002) *Nat Neurosci* 5:1302-1308; Yamashita et al., (2002) *J Cell Biol* 157:565-570; Yamashita and Tohyama, (2003) *Nat Neurosci* 6, 461-467). To confirm the role of p75NTR in N2a cells, we treated cells with TAT-pep5, a TAT-fusion peptide that binds to p75NTR and blocks p75NTR-dependent RhoA activation (Yamashita and Tohyama, 2003, supra). FIG. 7B shows that TAT-pep5 blocked RhoA activation in response to MAG-Fc. Thus, in N2a cells, both p75NTR and LRP1 are required for RhoA activation.

p75NTR does not bind independently to myelin-associated proteins. Instead, p75NTR is recruited into complex with NgR1 and PirB when these receptors bind myelin-associated proteins (Wong et al., 2002, supra; Shao et al., (2005) Neuron 45: 353-359; Fujita et al., (2011) *Cell death & disease* 2, e198). To test whether p75NTR associates with LRP1, we performed co-immunoprecipitation experiments. In the absence of MAG-Fc or when N2a cells were treated with Fc, little or no p75NTR co-immunoprecipitated with LRP1 (FIG. 7D). However, when N2a cells were treated with MAG-Fc, co-immunoprecipitation of p75NTR with LRP1 was robust. These results indicate that MAG-binding to LRP1 recruits p75NTR into complex with LRP1, reminiscent of the mechanism by which p75NTR associates with NgR1 and PirB.

The results presented in FIG. 1 are consistent with the conclusion that MAG-binding to LRP1 occurs without required co-receptors. To test whether p75NTR regulates MAG-binding to LRP1, we achieved partial p75NTR gene-silencing with siRNA in N20.1 cells (FIG. 7D). The total level of cellular LRP1 was not affected by p75NTR gene-silencing. MAG-Fc binding to LRP1 was examined by co-immunoprecipitation, 48 and 72 h after introducing the siRNA. Association of MAG-Fc with LRP1 was not significantly affected by p75NTR gene-silencing.

Shed LRP1 Inhibits the Effects of Myelin on Neurite Outgrowth in CGNs

Figure 8:
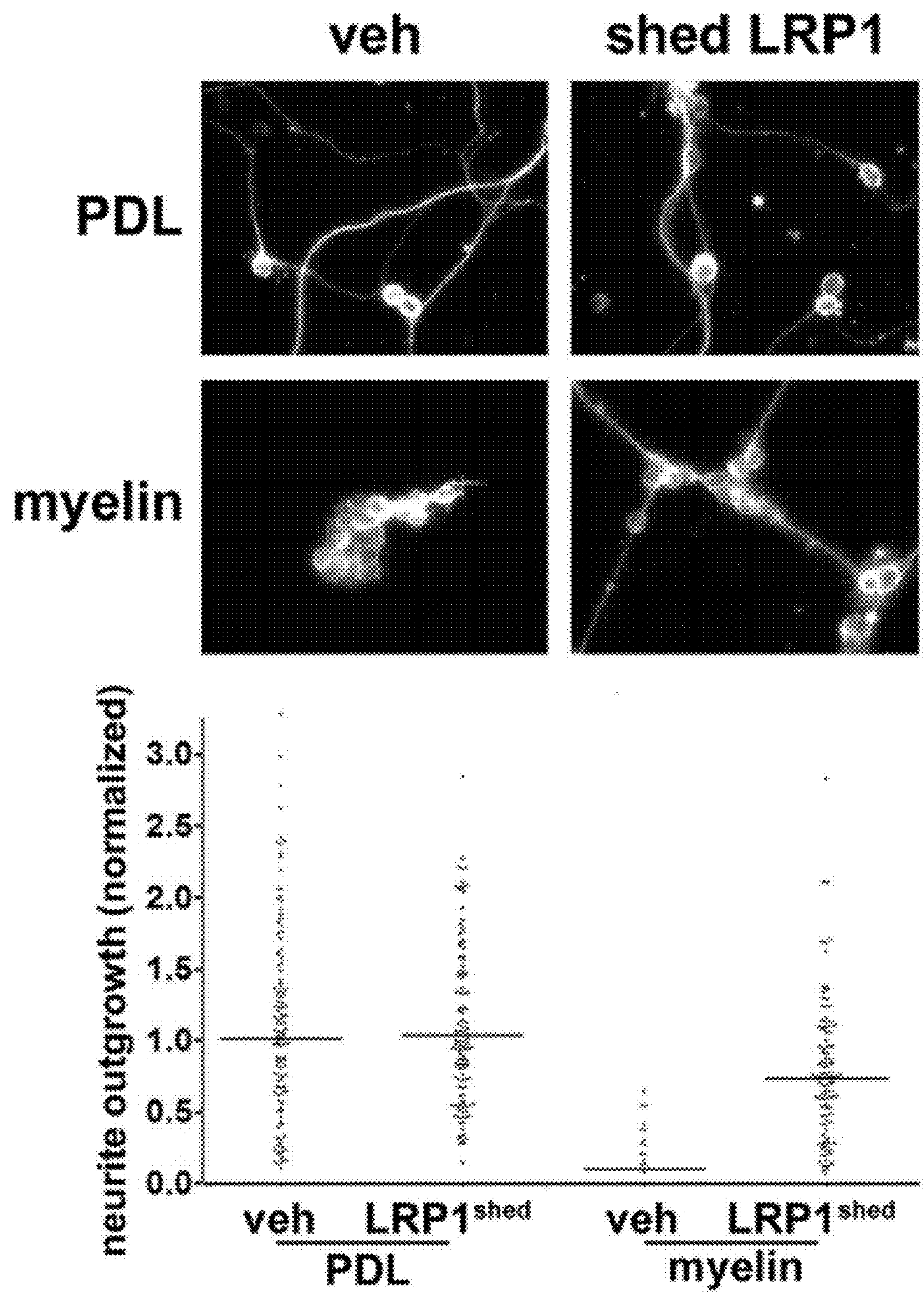
FIG. 8 illustrates that shed LRP1 blocks the effects of myelin on neurite outgrowth in CGNs Immobilized myelin and PDL were pre-treated with shed LRP1, which was purified from plasma, or with vehicle (veh). CGNs were then plated and allowed to differentiate for 72 h. CGNs were imaged by immunofluorescence microscopy after staining to detect βIII-tubulin. Neurite outgrowth was standardized against that observed when CGNs were plated on PDL, which was pre-treated with vehicle.
Figure 9:
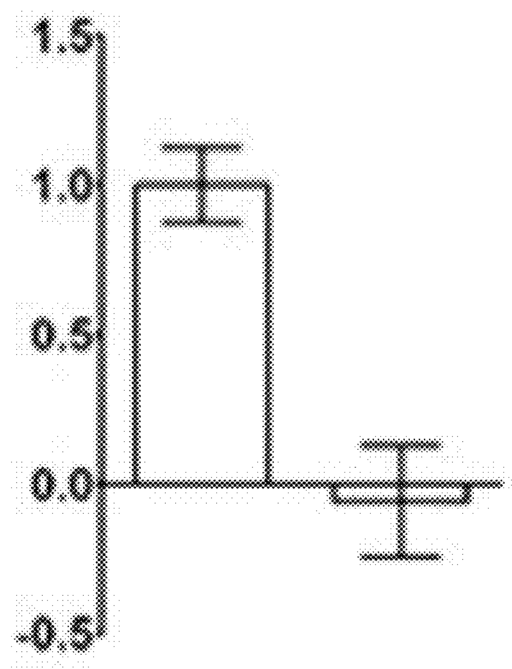
FIG. 9 illustrates endocytosis of MAG in neuronal N2a cells is LRP1 dependent. LRP1 expressing and -deficient N2a cells were incubated with 25 nM $^{125}$I-MAG-Fc, in the presence or absence of a 50-fold molar excess of unlabeled MAG-Fc. Specific MAG-Fc internalization was determined (*, $p<0.01$).
Figure 10:
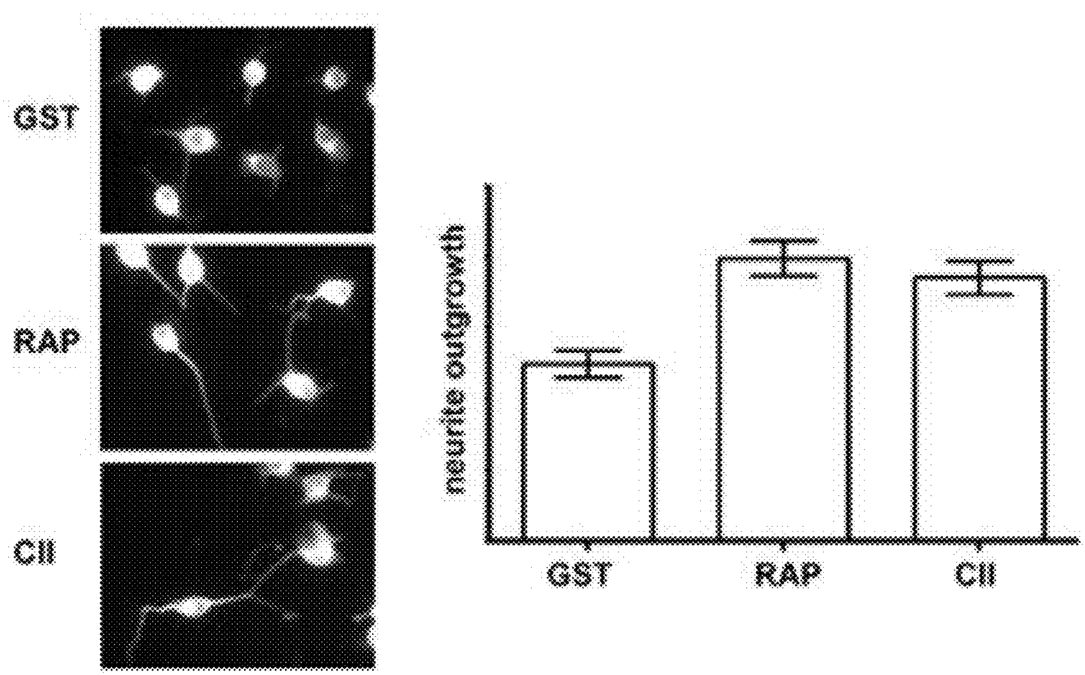
FIG. 10 illustrates pre-treatment of inhibitory MAG substrate with recombinant CII binding domain of LRP1 blocks inhibition of neurite outgrowth on N2a cells. A monolayer of membrane-bound MAG-expressing CHO cells was used as a model of inhibitory substrate. Substrate was then pre-treated with either CII-Fc or Fc control for 15 minutes prior to the addition of N2a cells, which were differentiated for 48 hours. N2a cells were then imaged by immunofluorescence microscopy after staining to detect βIII-tubulin. The pre-treatment of MAG cells with CII had a similar regenerative effect on N2a neurite outgrowth as RAP treatment.

LRP1 is released from cells as a "shed" product by α-secretase and accumulates in the blood and cerebrospinal fluid (Quinn et al., (1999) *Exp Cell Res* 251:433-441; Liu et al., (2009) *Molecular neurodegeneration* 4:17; Gorovoy et al., (2010) *J Leukoc Biol* 88:769-778). Shed LRP1 retains the entire LRP1 alpha-chain and thus, intact ligand-binding activity (Quinn et al., 1999, supra). We determined that shed LRP1 would compete with membrane-anchored LRP1 for inhibitory myelin proteins and thereby block the activity of myelin. Shed LRP1 was purified from human plasma, as previously described (Gorovoy et al., 2010, supra). When CGNs were plated on PDL, purified, shed LRP1 did not affect neurite outgrowth (FIG. 8). However, when CGNs were plated on purified rat myelin, shed LRP1 reversed the effects of myelin, restoring axonal outgrowth to nearly the level observed on PDL.

Discussion

Previously identified receptors for inhibitory myelin proteins include NgR1 and PirB (Fournier et al., (2001) *Nature* 409:341-346; Atwal et al., (2008) *Science* 322:967-970). Although p75NTR does not directly bind myelin-associated proteins, its recruitment may be essential for RhoA activation (Wong et al., 2002, supra; Yamashita et al., 2002, supra; Yamashita and Tohyama, 2003, supra). Other receptors implicated in myelin inhibitory signaling include LINGO-1 (Mi et al., (2004) *Nat Neurosci* 7:221-228; Ji et al., (2006) *Mol Cell Neurosci* 33: 311-320), β1 integrin (Hu and Strittmatter, (2008) *J Neurosci* 28:1262-1269), and TROY/TAJ (Shao et al., 2005, supra; Mi, et al., (2008) *Cytokine & growth factor reviews* 19:245-251). In this study, we describe LRP1 as the third major neuronal receptor for MAG and the principal MAG endocytic receptor. Consistent with the known ability of LRP1 to couple endocytosis with cell-signaling, we demonstrated that LRP1 is essential in the pathway by which MAG activates RhoA. We also demonstrated an essential role for LRP1 in the pathway by which MAG inhibits neurite outgrowth. Although we have not yet evaluated the activity of LRP1 in experiments with purified Nogo or OMgp, inactivating LRP1 effectively reversed the effects of purified rat myelin on neurite outgrowth, suggesting that LRP1 is required for inhibition of neurite outgrowth by myelin-associated proteins in addition to MAG.

MAG binds to LRP1 in purified protein systems, suggesting that co-receptors are not required for this interaction in intact cells. MAG-binding recruits p75NTR into complex with LRP1, forming a functional unit capable of activating RhoA. Thus, our results may be interpreted to indicate that LRP1 and p75NTR form an independent receptor complex for myelin-associated proteins, capable of activating inhibitory signaling. An alternative model is that LRP1 functions as a newly identified member of a multiprotein receptor complex that includes not only p75NTR, but also possibly NgR1 or PirB. There are advantages to be gained if LRP1 functions in concert with NgR1 or PirB. First, be-cause myelin-associated proteins in the injured CNS may be presented to neurons as multimers, the combined activity of LRP1 with NgR1 or PirB may increase affinity. In addition, LRP1 is known to traffic multiprotein complexes into clathrin-coated pits and endosomes (Strickland et al., (2002) *Trends Endocrinol Metab* 13:66-74; Wu and Gonias, (2005) *J Cell Biochem* 96, 1021-1033), which could be important for cell-signaling.

Joset et al. (*J Cell Biol* (2010) 188:271-285) demonstrated that a biologically active fragment of Nogo activates RhoA by a mechanism that requires Pincher-dependent macroendocytosis of the Nogo fragment. Although this pathway occurs independently of clathrin-coated pits, formation of the signalosome and vesicular transport of the Nogo fragment within the cell was pivotal for growth cone collapse. Endocytosis of MAG by LRP1, possibly in combination with p75NTR and other members of the MAG receptor complex, could provide a related pathway for intracellular trafficking of myelin products and RhoA activation. Interestingly, Steuble et al. (Steuble et al., (2010) *Proteomics* 10:3775-3788 co-localized Nogo with LRP1 in early endosomes when they analyzed growth cone vesicles isolated from P7 mouse brain.

When CGNs or PC12 cells are plated on non-inhibitory substrata, the LRP1 ligands, tissue-type plasminogen activator (tPA) and α2-macroglobulin (α2M), activate LRP1-dependent cell-signaling pathways that promote neurite outgrowth and neuronal survival (Qiu et al., (2004) *J Biol Chem* 279:34948-34956; Hayashi et al., (2007) *J Neurosci* 27:1933-1941; Hu et al., (2007) *J Clin Invest* 117:3821-3832; Mantuano et al., (2008) *J Neurosci* 28:11571-11582). These ligands activate Src family kinases (SFKs), downstream of LRP1, causing trans-activation of Trk receptors and Trk-dependent activation of ERK and Akt (Shi et al., (2009) *Sci Signal* 2:ra18). However, not all proteins that bind to LRP1 activate cell-signaling and promote neurite outgrowth, including, for example, RAP. In a number of model systems, RAP has no independent cell-signaling activity and, in addition, blocks cell-signaling and neurite outgrowth initiated by LRP1 ligands such as tPA (Qiu et al., 2004, supra; Hu et al. 2007, supra; Hayashi et al., 2007, supra; Mantuano et al., (2008a) supra). The mechanism by which specific LRP1 ligands activate SFKs remains unclear. Co-receptors, such as the NMDA receptor, may be involved (May et al., (2004) *Mol Cell Biol* 24:8872-8883; Rebeck, (2009) *Sci Signal* 2:pe28). However, when neurons are plated on MAG or myelin, the cell-signaling activity of LRP1 is changed. The results are consistent with a model in which recruitment of p75NTR into complex with LRP1 is pivotal for the shift in LRP1 signaling activity, favoring RhoA activation as opposed to Trk receptors. The results are further consistent with the conclusion that p75NTR recruitment is restricted to ligand-binding events involving MAG or other myelin-derived proteins. Once p75NTR is recruited into complex with LRP1, by MAG or other myelin-derived proteins, cell-signaling downstream of LRP1 is shifted from "pro-neuritogenic" to "anti-neuritogenic". Precedent for our model is derived from other examples in which LRP1 co-receptors substantially modify the signaling activity of LRP1. In Schwann cells, direct binding of matrix metalloprotease-9 or tPA to LRP1 activates Rac1 (Mantuano et al., (2010) *J Biol Chem* 285: 14259-14266). By contrast, in embryonic fibroblasts, LRP1 decreases the level of activated Rac1 by associating with uPAR, which inhibits uPAR-dependent Rac1 activation (Ma et al., (2002) *J Cell Biol* 159, 1061-1070).

In neurite outgrowth experiments, we assume that RAP was active by binding to LRP1 and competitively inhibiting binding of MAG or purified myelin. Similarly, because shed LRP1 retains unaltered ligand-binding activity (Quinn et al., (1999) *Exp Cell Res* 251, 433-441; Gorovoy et al., (2010) *J Leukoc Biol* 88:769-778), the results are consistent with the conclusion that shed LRP1 reversed the effects of myelin on axonal outgrowth in CGNs by competitive displacement of myelin-derived proteins from membrane-anchored LRP1. Shed LRP1 also competitively blocks binding of inhibitory myelin proteins to other receptors, such as NgR1. In either case, these results support a model in which the activity of MAG and other inhibitory myelin proteins are counteracted by targeting the myelin-associated protein or by targeting the CII/CIV domains of LRP1. Because proteins that bind to LRP1 and trigger pro-neuritogenic signaling on non-inhibitory substrata, such as tPA and α2M, bind to CII/CIV, these proteins also inhibit binding of MAG to LRP1. Recombinant derivatives of LRP1 ligands, which were designed specifically to activate LRP1-dependent cell-signaling (Mantuano et al., (2008) *J Neurosci* 28:11571-11582; Mantuano et al., (2008) *J Biol Chem* 283:19904-19911, may be effective at displacing MAG and other inhibitory myelin proteins from LRP1. The activity of any candidate for competitive displacement of MAG from LRP1 will depend on the concentration of that ligand relative to the affinity for LRP1.

Shed LRP1 is generated by the α-secretase, ADAM17 (Gorovoy et al., 2010). Inflammation increases LRP1 shedding and promotes the accumulation of shed LRP1 in the plasma (Gorovoy et al., 2010, supra). In CNS ischemia, shedding of LRP1 from perivascular astrocytes is significantly increased (Polavarapu et al., (2007) *Blood* 109(8):3270-8). It is not clear whether LRP1 shedding from neurons is regulated; however, our results suggest that shed LRP1, which is generated in the brain, may serve as an endogenous antagonist of the anti-regenerative activity of MAG and possibly other myelin inhibitory proteins. The biological activity of shed LRP1 in processes such as neuronal survival merits further consideration.

In the normal human brain, expression of LRP1 is limited mainly to neuronal populations (Wolf et al., (1992) *Am J Pathol* 141:37-42; Lopes et al., (1994) *FEBS Lett* 338:301-305). However, in CNS injury, LRP1 expression significantly increases in reactive astrocytes (Lopes et al., 1994, supra). Our previous studies suggest that LRP1-dependent phagocytosis of myelin debris occurs across diverse cell types (Gaultier et al., (2009) *J Cell Sci* 122:1155-1162). The increase in LRP1 expression by reactive astrocytes in the injured CNS may limit the burden of myelin-derived proteins presented to neurons and thus, play a protective role. Taken together, these past studies and the work presented here suggest that a balance between neuronal LRP1, astrocytic LRP1, and shed LRP1 may be critical in determining the effects of inhibitory myelin proteins on neuronal repair in the CNS, following injuries of diverse magnitudes.

REFERENCES

Atwal, J. K., Pinkston-Gosse, J., Syken, J., Stawicki, S., Wu, Y., Shatz, C., and Tessier-Lavigne, M. (2008). PirB is a functional receptor for myelin inhibitors of axonal regeneration. Science 322, 967-970.

Berry, M. (1982). Post-injury myelin-breakdown products inhibit axonal growth: an hypothesis to explain the failure of axonal regeneration in the mammalian central nervous system. Bibliotheca anatomica, 1-11.

Boucher, P., Gotthardt, M., Li, W. P., Anderson, R. G., and Herz, J. (2003). LRP: role in vascular wall integrity and protection from atherosclerosis. Science 300, 329-332.

Brown, M. D., Banker, G. A., Hussaini, I. M., Gonias, S. L., and VandenBerg, S. R. (1997). Low density lipoprotein receptor-related protein is expressed early and becomes restricted to a somatodendritic domain during neuronal differentiation in culture. Brain Res 747, 313-317.

Bu, G., Maksymovitch, E. A., Nerbonne, J. M., and Schwartz, A. L. (1994). Expression and function of the low density lipoprotein receptor-related protein (LRP) in mammalian central neurons. J Biol Chem 269, 18521-18528.

Campana, W. M., Li, X., Dragojlovic, N., Janes, J., Gaultier, A., and Gonias, S. L. (2006). The low-density lipoprotein receptor-related protein is a pro-survival receptor in Schwann cells: possible implications in peripheral nerve injury. J Neurosci 26, 11197-11207.

Collins, B. E., Yang, L. J., Mukhopadhyay, G., Filbin, M. T., Kiso, M., Hasegawa, A., and Schnaar, R. L. (1997). Sialic acid specificity of myelin-associated glycoprotein binding. J Biol Chem 272, 1248-1255.

Domeniconi, M., Cao, Z., Spencer, T., Sivasankaran, R., Wang, K., Nikulina, E., Kimura, N., Cai, H., Deng, K., Gao, Y., et al. (2002). Myelin-associated glycoprotein interacts with the Nogo66 receptor to inhibit neurite outgrowth. Neuron 35, 283-290.

Filbin, M. T. (2003). Myelin-associated inhibitors of axonal regeneration in the adult mammalian CNS. Nat Rev Neurosci 4, 703-713.

FitzGerald, D. J., Fryling, C. M., Zdanovsky, A., Saelinger, C. B., Kounnas, M., Winkles, J. A., Strickland, D., and Leppla, S. (1995). *Pseudomonas* exotoxin-mediated selection yields cells with altered expression of low-density lipoprotein receptor-related protein. J Cell Biol 129, 1533-1541.

Fournier, A. E., GrandPre, T., and Strittmatter, S. M. (2001). Identification of a receptor mediating Nogo-66 inhibition of axonal regeneration. Nature 409, 341-346.

Fu, Q., Hue, J., and Li, S. (2007). Nonsteroidal anti-inflammatory drugs promote axon regeneration via RhoA inhibition. J Neurosci 27, 4154-4164.

Fuentealba, R. A., Liu, Q., Kanekiyo, T., Zhang, J., and Bu, G. (2009). Low density lipoprotein receptor-related protein 1 promotes anti-apoptotic signaling in neurons by activating Akt survival pathway. J Biol Chem 284, 34045-34053.

Fujita, Y., Takashima, R., Endo, S., Takai, T., and Yamashita, T. (2011). The p75 receptor mediates axon growth inhibition through an association with PIR-B. Cell death & disease 2, e198.

Gaultier, A., Arandjelovic, S., Niessen, S., Overton, C. D., Linton, M. F., Fazio, S., Campana, W. M., Cravatt, B. F., 3rd, and Gonias, S. L. (2008). Regulation of tumor necrosis factor receptor-1 and the IKK-NF-kappaB pathway by LDL receptor-related protein explains the antiinflammatory activity of this receptor. Blood 111, 5316-5325.

Gaultier, A., Simon, G., Niessen, S., Dix, M., Takimoto, S., Cravatt 3rd, B., and Gonias, S. (2010). LDL receptor-related protein 1 regulates the abundance of diverse cell-signaling proteins in the plasma membrane proteome. J Proteome Res 9, 6689-6695.

Gaultier, A., Wu, X., Le Moan, N., Takimoto, S., Mukandala, G., Akassoglou, K., Campana, W. M., and Gonias, S. L. (2009). Low-density lipoprotein receptor-related protein 1 is an essential receptor for myelin phagocytosis. J Cell Sci 122, 1155-1162.

Gorovoy, M., Gaultier, A., Campana, W., Firestein, G., and Gonias, S. (2010). Inflammatory mediators promote production of shed LRP1/CD91, which regulates cell signaling and cytokine expression by macrophages. J Leukoc Biol 88, 769-778.

Hayashi, H., Campenot, R., Vance, D., and Vance, J. (2007). Apolipoprotein E-containing lipoproteins protect neurons from apoptosis via a signaling pathway involving low-density lipoprotein receptor-related protein-1. J Neurosci 27, 1933-1941.

Hu, F., and Strittmatter, S. M. (2008). The N-terminal domain of Nogo-A inhibits cell adhesion and axonal outgrowth by an integrin-specific mechanism. J Neurosci 28, 1262-1269.

Hu, K., Wu, C., Mars, W. M., and Liu, Y. (2007). Tissue-type plasminogen activator promotes murine myofibroblast activation through LDL receptor-related protein 1-mediated integrin signaling. J Clin Invest 117, 3821-3832.

Hynds, D. L., and Snow, D. M. (1999). Neurite outgrowth inhibition by chondroitin sulfate proteoglycan: stalling/stopping exceeds turning in human neuroblastoma growth cones. Experimental neurology 160, 244-255.

Jalink, K., van Corven, E. J., Hengeveld, T., Morii, N., Narumiya, S., and Moolenaar, W. H. (1994). Inhibition of lysophosphatidate and thrombin-induced neurite retraction and neuronal cell rounding by ADP ribosylation of the small GTP-binding protein Rho. J Cell Biol 126, 801-810.

Jeon, C. Y., Moon, M. Y., Kim, J. H., Kim, H. J., Kim, J. G., Li, Y., Jin, J. K., Kim, P. H., Kim, H. C., Meier, K. E., et al. (2012). Control of neurite outgrowth by RhoA inactivation. J Neurochem. 120(5):684-698.

Ji, B., Li, M., Wu, W. T., Yick, L. W., Lee, X., Shao, Z., Wang, J., So, K. F., McCoy, J. M., Pepinsky, R. B., et al. (2006). LINGO-1 antagonist promotes functional recovery and axonal sprouting after spinal cord injury. Mol Cell Neurosci 33, 311-320.

Joset, A., Dodd, D. A., Halegoua, S., and Schwab, M. E. (2010). Pincher-generated Nogo-A endosomes mediate growth cone collapse and retrograde signaling. J Cell Biol 188, 271-285.

Kozma, R., Sarner, S., Ahmed, S., and Lim, L. (1997). Rho family GTPases and neuronal growth cone remodelling: relationship between increased complexity induced by Cdc42Hs, Rac1, and acetylcholine and collapse induced by RhoA and lysophosphatidic acid. Mol Cell Biol 17, 1201-1211.

Kuhn, T. B., Brown, M. D., Wilcox, C. L., Raper, J. A., and Bamburg, J. R. (1999). Myelin and collapsin-1 induce motor neuron growth cone collapse through different pathways: inhibition of collapse by opposing mutants of rac1. J Neurosci 19, 1965-1975.

Lillis, A. P., Greenlee, M. C., Mikhailenko, I., Pizzo, S. V., Tenner, A. J., Strickland, D. K., and Bohlson, S. S. (2008). Murine low-density lipoprotein receptor-related protein 1 (LRP) is required for phagocytosis of targets bearing LRP ligands but is not required for Clq-triggered enhancement of phagocytosis. J Immunol 181, 364-373.

Liu, Q., Zhang, J., Tran, H., Verbeek, M. M., Reiss, K., Estus, S., and Bu, G. (2009). LRP1 shedding in human brain: roles of ADAM10 and ADAM17. Molecular neurodegeneration 4, 17.

Lopes, M. B., Bogaev, C. A., Gonias, S. L., and VandenBerg, S. R. (1994). Expression of alpha 2-macroglobulin receptor/low density lipoprotein receptor-related protein is increased in reactive and neoplastic glial cells. FEBS Lett 338, 301-305.

Ma, Z., Thomas, K. S., Webb, D. J., Moravec, R., Salicioni, A. M., Mars, W. M., and Gonias, S. L. (2002). Regulation of Rac1 activation by the low density lipoprotein receptor-related protein. J Cell Biol 159, 1061-1070.

Madura, T., Yamashita, T., Kubo, T., Fujitani, M., Hosokawa, K., and Tohyama, M. (2004). Activation of Rho in the injured axons following spinal cord injury. EMBO reports 5, 412-417.

Mantuano, E., Inoue, G., Li, X., Takahashi, K., Gaultier, A., Gonias, S. L., and Campana, W. M. (2008a). The hemopexin domain of matrix metalloproteinase-9 activates cell signaling and promotes migration of schwann cells by binding to low-density lipoprotein receptor-related protein. J Neurosci 28, 11571-11582.

Mantuano, E., Jo, M., Gonias, S., and Campana, W. (2010). Low density lipoprotein receptor-related protein (LRP1) regulates Rac1 and RhoA reciprocally to control Schwann cell adhesion and migration. J Biol Chem 285, 14259-14266.

Mantuano, E., Mukandala, G., Li, X., Campana, W. M., and Gonias, S. L. (2008b). Molecular dissection of the human alpha2-macroglobulin subunit reveals domains with antagonistic activities in cell signaling. J Biol Chem 283, 19904-19911.

May, P., Rohlmann, A., Bock, H., Zurhove, K., Marth, J. S., ED, Noebels, J., Beffert, U., Sweatt, J. W., E J, and Herz, J. (2004). Neuronal LRP1 functionally associates with postsynaptic proteins and is required for normal motor function in mice. Mol Cell Biol 24, 8872-8883.

Mi, S. (2008). Troy/Taj and its role in CNS axon regeneration. Cytokine & growth factor reviews 19, 245-251.

Mi, S., Lee, X., Shao, Z., Thill, G., Ji, B., Relton, J., Levesque, M., Allaire, N., Perrin, S., Sands, B., et al. (2004). LINGO-1 is a component of the Nogo-66 receptor/p75 signaling complex. Nat Neurosci 7, 221-228.

Ng, W. P., Cartel, N., Roder, J., Roach, A., and Lozano, A. (1996). Human central nervous system myelin inhibits neurite outgrowth. Brain Res 720, 17-24.

Niederost, B., Oertle, T., Fritsche, J., McKinney, R. A., and Bandtlow, C. E. (2002). Nogo-A and myelin-associated glycoprotein mediate neurite growth inhibition by antagonistic regulation of RhoA and Rac1. J Neurosci 22, 10368-10376.

Norton, W. T., and Poduslo, S. E. (1973). Myelination in rat brain: method of myelin isolation. J Neurochem 21, 749-757.

Oberdoerster, J. (2001). Isolation of Cerebellar Granule Cells from Neonatal Rats (John Wiley & Sons).

Oohira, A., Matsui, F., and Katoh-Semba, R. (1991). Inhibitory effects of brain chondroitin sulfate proteoglycans on neurite outgrowth from PC12D cells. J Neurosci 11, 822-827.

Polavarapu, R., Gongora, M. C., Yi, H., Ranganthan, S., Lawrence, D. A., Strickland, D., and Yepes, M. (2007). Tissue-type plasminogen activator-mediated shedding of astrocytic low density lipoprotein receptor-related protein increases the permeability of the neurovascular unit. Blood 109(8):3270-8.

Qiu, Z., Hyman, B., and Rebeck, G. (2004). Apolipoprotein E receptors mediate neurite outgrowth through activation of p44/42 mitogen-activated protein kinase in primary neurons. J Biol Chem 279, 34948-34956.

Quinn, K. A., Pye, V. J., Dai, Y. P., Chesterman, C. N., and Owensby, D. A. (1999). Characterization of the soluble form of the low density lipoprotein receptor-related protein (LRP). Exp Cell Res 251, 433-441.

Rebeck, G. (2009). Nontraditional signaling mechanisms of lipoprotein receptors. Sci Signal 2, pe28.

Shao, Z., Browning, J. L., Lee, X., Scott, M. L., Shulga-Morskaya, S., Allaire, N., Thill, G., Levesque, M., Sah, D., McCoy, J. M., et al. (2005). TAJ/TROY, an orphan TNF receptor family member, binds Nogo-66 receptor 1 and regulates axonal regeneration. Neuron 45, 353-359.

Shi, Y., Mantuano, E., Inoue, G., Campana, W., and Gonias, S. (2009). Ligand binding to LRP1 transactivates Trk receptors by a Src family kinase-dependent pathway. Sci Signal 2, ra18.

Steuble, M., Gerrits, B., Ludwig, A., Mateos, J. M., Diep, T. M., Tagaya, M., Stephan, A., Schatzle, P., Kunz, B., Streit, P., et al. (2010). Molecular characterization of a trafficking organelle: dissecting the axonal paths of calsyntenin-1 transport vesicles. Proteomics 10, 3775-3788.

Strickland, D. K., Gonias, S. L., and Argraves, W. S. (2002). Diverse roles for the LDL receptor family. Trends Endocrinol Metab 13, 66-74.

Tan, E. Y., Law, J. W., Wang, C. H., and Lee, A. Y. (2007). Development of a cell transducible RhoA inhibitor TAT-C3 transferase and its encapsulation in biocompatible microspheres to promote survival and enhance regeneration of severed neurons. Pharmaceutical research 24, 2297-2308.

Tang, S., Woodhall, R. W., Shen, Y. J., deBellard, M. E., Saffell, J. L., Doherty, P., Walsh, F. S., and Filbin, M. T. (1997). Soluble myelin-associated glycoprotein (MAG) found in vivo inhibits axonal regeneration. Mol Cell Neurosci 9, 333-346.

Wang, K. C., Koprivica, V., Kim, J. A., Sivasankaran, R., Guo, Y., Neve, R. L., and He, Z. (2002). Oligodendrocyte-myelin glycoprotein is a Nogo receptor ligand that inhibits neurite outgrowth. Nature 417, 941-944.

Webb, D., Thomas, K., and Gonias, S. (2001). Plasminogen activator inhibitor 1 functions as a urokinase response modifier at the level of cell signaling and thereby promotes MCF-7 cell growth. J Cell Biol 152, 741-752.

Wight, P. A., and Dobretsova, A. (1997). The first intron of the myelin proteolipid protein gene confers cell type-specific expression by a transcriptional repression mechanism in non-expressing cell types. Gene 201, 111-117.

Williams, S. E., Ashcom, J. D., Argraves, W. S., and Strickland, D. K. (1992). A novel mechanism for controlling the activity of alpha 2-macroglobulin receptor/low density lipoprotein receptor-related protein. Multiple regulatory sites for 39-kDa receptor-associated protein. J Biol Chem 267, 9035-9040.

Willnow, T. E., Orth, K., and Herz, J. (1994). Molecular dissection of ligand binding sites on the low density lipoprotein receptor-related protein. J Biol Chem 269, 15827-15832.

Wolf, B. B., Lopes, M. B., VandenBerg, S. R., and Gonias, S. L. (1992). Characterization and immunohistochemical localization of alpha 2-macroglobulin receptor (low-density lipoprotein receptor-related protein) in human brain. Am J Pathol 141, 37-42.

Wong, S. T., Henley, J. R., Kanning, K. C., Huang, K. H., Bothwell, M., and Poo, M. M. (2002). A p75 (NTR) and Nogo receptor complex mediates repulsive signaling by myelin-associated glycoprotein. Nat Neurosci 5, 1302-1308.

Wu, L., and Gonias, S. L. (2005). The low-density lipoprotein receptor-related protein-1 associates transiently with lipid rafts. J Cell Biochem 96, 1021-1033.

Yamashita, T., Higuchi, H., and Tohyama, M. (2002). The p75 receptor transduces the signal from myelin-associated glycoprotein to Rho. J Cell Biol 157, 565-570.

Yamashita, T., and Tohyama, M. (2003). The p75 receptor acts as a displacement factor that releases Rho from Rho-GDI. Nat Neurosci 6, 461-467.

Yiu, G., and He, Z. (2006). Glial inhibition of CNS axon regeneration. Nat Rev Neurosci 7, 617-627.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes. /////

SEQUENCE LISTING

Sequence ID No: 1-mRNA sequence of *Homo sapiens* low density lipoprotein receptor-related protein 1 (LRP1)-NCBI Reference Sequence: M1_002332.2

```
   1 cagcggtgcg agctccaggc ccatgcactg aggaggcgga aacaagggga gcccccagag
  61 ctccatcaag ccccctccaa aggctcccct acccggtcca cgccccccac cccccctccc
 121 cgcctcctcc caattgtgca tttttgcagc cggaggcggc tccgagatgg ggctgtgagc
 181 ttcgcccggg gaggggaaa gagcagcgag gagtgaagcg gggggtggg gtgaagggtt
 241 tggatttcgg ggcagggggc gcacccccgt cagcaggccc tccccaaggg gctcggaact
 301 ctacctcttc acccacgccc ctggtgcgct ttgccgaagg aaagaataag aacagagaag
 361 gaggaggggg aaaggaggaa aagggggacc ccccaactgg gggggtgaa ggagagaagt
 421 agcaggacca gaggggaagg ggctgctgct tgcatcagcc cacaccatgc tgaccccgcc
 481 gttgctcctg ctgctgcccc tgctctcagc tctggtcgcg gcggctatcg acgcccctaa
 541 gacttgcagc cccaagcagt ttgcctgcag agatcaaata acctgtatct caaagggctg
 601 gcggtgcgac ggtgagaggg actgcccaga cggatctgac gaggcccctg agatttgtcc
 661 acagagtaag gcccagcgat gccagccaaa cgagcataac tgcctgggta ctgagctgtg
 721 tgttcccatg tcccgcctct gcaatggggt ccaggactgc atggacggct cagatgaggg
 781 gccccactgc cgagagctcc aaggcaactg ctctcgcctg ggctgccagc accattgtgt
 841 ccccacactc gatgggccca cctgctactg caacagcagc tttcagcttc aggcagatgg
 901 caagacctgc aaagattttg atgagtgctc agtgtacggc acctgcagcc agctatgcac
 961 caacacagac ggctccttca tatgtggctg tgttgaagga tacctcctgc agccggataa
1021 ccgctcctgc aaggccaaga acgagccagt agaccggccc cctgtgctgt tgatagccaa
1081 ctcccagaac atcttggcca cgtacctgag tggggcccag gtgtctacca tcacacctac
1141 gagcacgcgg cagaccacag ccatggactt cagctatgcc aacgagaccg tatgctgggt
1201 gcatgttggg gacagtgctg ctcagacgca gctcaagtgt gcccgcatgc ctggcctaaa
1261 gggcttcgtg gatgagcaca ccatcaacat ctccctcagt ctgcaccacg tggaacagat
1321 ggccatcgac tggctgacag gcaacttcta ctttgtggat gacatcgatg ataggatctt
1381 tgtctgcaac agaaatgggg acacatgtgt cacattgcta gacctggaac tctacaaccc
1441 caagggcatt gccctggacc ctgccatggg gaaggtgttt ttcactgact atgggcagat
1501 cccaaaggtg gaacgctgtg acatggatgg gcagaaccgc accaagctcg tcgacagcaa
1561 gattgtgttt cctcatggca tcacgctgga cctggtcagc cgccttgtct actgggcaga
1621 tgcctatctg gactatattg aagtggtgga ctatgagggc aagggccgcc agaccatcat
1681 ccagggcatc ctgattgagc acctgtacgg cctgactgtg tttgagaatt atctctatgc
1741 caccaactcg gacaatgcca atgcccagca gaagacgagt gtgatccgtg tgaaccgctt
1801 taacagcacc gagtaccagg ttgtcacccg ggtggacaag ggtggtgccc tccacatcta
1861 ccaccagagg cgtcagcccc gagtgaggag ccatgcctgt gaaaacgacc agtatgggaa
1921 gccgggtggc tgctctgaca tctgcctgct ggccaacagc cacaaggcgc ggacctgccg
1981 ctgccgttcc ggcttcagcc tgggcagtga cgggaagtca tgcaagaagc cggagcatga
2041 gctgttcctc gtgtatggca agggccggcc aggcatcatc cggggcatgg atatgggggc
2101 caaggtcccg gatgagcaca tgatccccat tgaaaacctc atgaaccccc gagccctgga
2161 cttccacgct gagaccggct tcatctactt tgccgacacc accagctacc tcattggccg
2221 ccagaagatt gatggcactg agcgggagac catcctgaag gacggcatcc acaatgtgga
2281 gggtgtggcc gtggactgga tgggagacaa tctgtactgg acggacgatg ggcccaaaaa
2341 gacaatcagc gtggccaggc tggagaaagc tgctcagacc cgcaagactt taatcgaggg
2401 caaaatgaca caccccaggg ctattgtggt ggatccactc aatgggtgga tgtactggac
2461 agactgggag gaggacccca aggacagtcg gcgtgggcgg ctggagaggg cgtggatgga
2521 tggctcacac cgagacatct ttgtcacctc caagacagtg ctttggccca atgggctaag
2581 cctggacatc ccggctgggc gcctctactg ggtggatgcc ttctacgacc gcatcgagac
2641 gatactgctc aatggcacag accggaagat tgtgtatgaa ggtcctgagc tgaaccacgc
2701 ctttggcctg tgtcaccatg gcaactacct cttctggact gagtatcgga gtggcagtgt
2761 ctaccgcttg gaacggggtg taggaggcgc accccccact gtgacccttc tgcgcagtga
2821 gcggcccccc atctttgaga tccgaatgta tgatgcccag cagcagcaag ttggcaccaa
2881 caaatgccgg gtgaacaatg gcggctgcag cagcctgtgc ttggccaccc ctgggagccg
2941 ccagtgcgcc tgtgctgagg accaggtgtt ggacgcagac ggcgtcactt gcttggcgaa
3001 cccatcctac gtgcctccac cccagtgcca gccaggcgag tttgcctgtg ccaacagccg
3061 ctgcatccag gagcgctgga agtgtgacgg agacaacgat tgcctggaca acagtgatga
3121 ggccccagcc ctctgccatc agcacacctg cccctcggac cgattcaagt gcgagaacaa
3181 ccggtgcatc cccaaccgct ggctctgcga cggggacaat gactgtggga acagtgaaga
3241 tgagtccaat gccacttgtt cagcccgcac ctgccccccc aaccagttct cctgtgccag
3301 tggccgctgc atccccatct cctggacgtg tgatctggat gacgactgtg gggaccgctc
3361 tgatgagtct gcttcgtgtg cctatcccac ctgcttcccc ctgactcagt ttacctgcaa
3421 caatggcaga tgtatcaaca tcaactggag atgcgacaat gacaatgact gtggggacaa
```

-continued

SEQUENCE LISTING

```
3481 cagtgacgaa gccggctgca gccactcctg ttctagcacc cagttcaagt gcaacagcgg
3541 gcgttgcatc cccgagcact ggacctgcga tggggacaat gactgcggag actacagtga
3601 tgagacacac gccaactgca ccaaccaggc cacgaggccc cctggtggct gccacactga
3661 tgagttccag tgccggctgg atggactatg catcccccctg cggtggcgct gcgatgggga
3721 cactgactgc atggactcca gcgatgagaa gagctgtgag ggagtgaccc acgtctgcga
3781 tcccagtgtc aagtttggct gcaaggactc agctcggtgc atcagcaaag cgtgggtgtg
3841 tgatggcgac aatgactgtg aggataactc ggacgaggag aactgcgagt ccctggcctg
3901 caggccaccc tcgcaccctt gtgccaacaa cacctcagtc tgcctgcccc ctgacaagct
3961 gtgtgatggc aacgacgact gtggcgacgg ctcagatgag ggcgagctct gcgaccagtg
4021 ctctctgaat aacggtggct gcagccacaa ctgctcagtg gcacctggcg aaggcattgt
4081 gtgttcctgc cctctgggca tggagctggg gcccgacaac cacacctgcc agatccagag
4141 ctactgtgcc aagcatctca aatgcagcca aaagtgcgac cagaacaagt tcagcgtgaa
4201 gtgctcctgc tacgagggct gggtcctgga acctgacggc gagagctgcc gcagcctgga
4261 ccccttcaag ccgttcatca ttttctccaa ccgccatgaa atccggcgca tcgatcttca
4321 caaaggagac tacagcgtcc tggtgcccgg cctgcgcaac accatcgccc tggacttcca
4381 cctcagccag agcgccctct actggaccga cgtggtggag gacaagatct accgcgggaa
4441 gctgctggac aacggagccc tgactagttt cgaggtggtg attcagtatg gcctggccac
4501 acccgagggc ctggctgtag actggattgc aggcaacatc tactgggtgg agagtaacct
4561 ggatcagatc gaggtggcca agctggatgg gaccctccgg accaccctgc tggccggtga
4621 cattgagcac ccaagggcaa tcgcactgga tccccgggat gggatcctgt tttggacaga
4681 ctgggatgcc agcctgcccc gcattgaggc agcctccatg agtggggctg ggcgccgcac
4741 cgtgcaccgg gagaccggct ctggggggctg gcccaacggg ctcaccgtgg actacctgga
4801 gaagcgcatc ctttggattg acgccaggtc agatgccatt tactcagccc gttacgacgg
4861 ctctggccac atggaggtgc ttcggggaca cgagttcctg tcgcacccgt ttgcagtgac
4921 gctgtacggg ggggaggtct actggactga ctggcgaaca aacacactgg ctaaggccaa
4981 caagtggacc ggccacaatg tcaccgtggt acagaggacc aacacccagc cctttgacct
5041 gcaggtgtac cacccctccc gccagcccat ggctcccaat ccctgtgagg ccaatggggg
5101 ccagggcccc tgctcccacc tgtgtctcat caactacaac cggaccgtgt cctgcgcctg
5161 cccccacctc atgaagctcc acaaggacaa caccacctgc tatgagttta agaagttcct
5221 gctgtacgca cgtcagatgg agatccgagg tgtggacctg gatgctccct actacaacta
5281 catcatctcc ttcacggtgc ccgacatcga caacgtcaca gtgctagact acgatgcccg
5341 cgagcagcgt gtgtactggt ctgacgtgcg gacacaggcc atcaagcggg ccttcatcaa
5401 cggcacaggc gtggagacag tcgtctctgc agacttgcca aatgcccacg ggctggctgt
5461 ggactgggtc tcccgaaacc tgttctggac aagctatgac accaataaga agcagatcaa
5521 tgtggcccgg ctggatggct ccttcaagaa cgcagtggtg cagggcctgg agcagcccca
5581 tggccttgtc gtccaccctc tgcgtgggaa gctctactgg accgatggtg acaacatcag
5641 catggccaac atggatggca gcaatcgcac cctgctcttc agtggccaga agggccccgt
5701 gggcctggct attgacttcc ctgaaagcaa actctactgg atcagctccg ggaaccatac
5761 catcaaccgc tgcaacctgg atgggagtgg gctggaggtc atcgatgcca tgcggagcca
5821 gctgggcaag gccaccgccc tggccatcat gggggacaag ctgtggtggg ctgatcaggt
5881 gtcggaaaag atgggcacat gcagcaaggc tgacggctcg ggctccgtgg tccttcggaa
5941 cagcaccacc ctggtgatgc acatgaaggt ctatgacgag agcatccagc tggaccataa
6001 gggcaccaac ccctgcagtg tcaacaacgg tgactgctcc cagctctgcc tgcccacgtc
6061 agagacgacc cgctcctgca tgtgcacagc cggctatagc ctccggagtg gccagcaggc
6121 ctgcgagggc gtaggttcct ttctcctgta ctctgtgcat gagggaatca ggggaattcc
6181 cctggatccc aatgacaagt cagatgccct ggtcccagtg tccgggacct cgctggctgt
6241 cggcatcgac ttccacgctg aaaatgacac catctactgg gtggacatgg gcctgagcac
6301 gatcagccgg gccaagcggg accagacgtg gcgtgaagac gtggtgacca atggcattgg
6361 ccgtgtggag ggcattgcag tggactggat cgcaggcaac atctactgga cagaccaggg
6421 ctttgatgtc atcgaggtcg cccggctcaa tggctccttc cgctacgtgg tgatctccca
6481 gggtctagac aagccccggg ccatcaccgt ccacccggag aaagggtact tgttctggac
6541 tgagtggggt cagtatccgc gtattgagcg gtctcggcta gatggcacgg agcgtgtggt
6601 gctggtcaac gtcagcatca gctggcccaa cggcatctca gtggactacc aggatgggaa
6661 gctgtactgg tgcgatgcac ggacagacaa gattgaacgg atcgacctgg agacaggtga
6721 gaaccgcgag gtggttctgt ccagcaacaa catggacatg ttttcagtgt ctgtgtttga
6781 ggatttcatc tactggagtg acaggactca tgccaacggc tctatcaagc gcgggagcaa
6841 agacaatgcc acagactccg tgcccctgcg aaccggcatc ggcgtccagc ttaaagacat
6901 caaagtcttc aaccgggacc ggcagaaagg caccaacgtg tgcgcggtgg ccaatggcgg
6961 gtgccagcag ctgtgcctgt accggggccg tgggcagcgg gcctgcgcct gtgcccacgg
7021 gatgctggct gaagacggag catcgtgccg cgagtatgcc ggctacctgc tctactcaga
7081 gcgcaccatt ctcaagagta tccacctgtc ggatgagcgc aacctcaatg cgcccgtgca
7141 gcccttcgag gaccctgagc acatgaagaa cgtcatcgcc ctggcctttg actaccgggc
7201 aggcacctct ccgggcaccc ccaatcgcat cttcttcagc gacatccact ttgggaacat
7261 ccaacagatc aacgacgatg gctccaggag gatcaccatt gtggaaaacg tgggctccgt
7321 ggaaggcctg gcctatcacc gtggctggga cactctctat tggacaagct acacgacatc
7381 caccatcacg cgccacacag tggaccagac ccgcccaggg gccttcgagc gtgagaccgt
7441 catcactatg tctggagatg accacccacg ggccttcgtt ttggacgagt gccagaacct
7501 catgttctgg accaactgga atgagcagca tcccagcatc atgcgggcgg cgctctcggg
7561 agccaatgtc ctgaccctta tcgagaagga catccgtacc cccaatggcc tggccatcga
7621 ccaccgtgcc gagaagctct acttctctga cgccaccctg gacaagatcg agcggtgcga
7681 gtatgacggc tcccaccgct atgtgatcct aaagtcagag cctgtccacc ccttcgggct
7741 ggccgtgtat ggggagcaca ttttctggac tgactgggtg cggcgggcag tgcagcgggc
7801 caacaagcac gtgggcagca acatgaagct gctgcgcgtg gacatccccc agcagcccat
7861 gggcatcatc gccgtggcca acgacaccaa cagctgtgaa ctctctccat gccgaatcaa
7921 caacggtggc tgccaggacc tgtgtctgct cactcaccag ggccatgtca actgctcatg
7981 ccgagggggc cgaatcctcc aggatgacct cacctgccga gcggtgaatt cctcttgccg
8041 agcacaagat gagtttgagt gtgccaatgg cgagtgcatc aacttcagcc tgacctgcga
```

-continued

SEQUENCE LISTING

```
 8101 cggcgtcccc cactgcaagg acaagtccga tgagaagcca tcctactgca actcccgccg
 8161 ctgcaagaag actttccggc agtgcagcaa tgggcgctgt gtgtccaaca tgctgtggtg
 8221 caacggggcc gacgactgtg gggatggctc tgacgagatc ccttgcaaca agacagcctg
 8281 tggtgtgggc gagttccgct gccgggacgg gacctgcatc gggaactcca gccgctgcaa
 8341 ccagtttgtg gattgtgagg acgcctcaga tgagatgaac tgcagtgcca ccgactgcag
 8401 cagctacttc cgcctgggcg tgaagggcgt gctcttccag ccctgcgagc ggacctcact
 8461 ctgctacgca cccagctggg tgtgtgatgg cgccaatgac tgtggggact acagtgatga
 8521 gcgcgactgc ccaggtgtga aacgccccag atgccctctg aattacttcg cctgccctag
 8581 tgggcgctgc atccccatga gctggacgtg tgacaaagag gatgactgtg aacatggcga
 8641 ggacgagacc cactgcaaca agttctgctc agaggcccag tttgagtgcc agaaccatcg
 8701 ctgcatctcc aagcagtggc tgtgtgacgg cagcgatgac tgtggggatg gctcagacga
 8761 ggctgctcac tgtgaaggca agacgtgcgg cccctcctcc ttctcctgcc ctggcaccca
 8821 cgtgtgcgtc cccgagcgct ggctctgtga cggtgacaaa gactgtgctg atggtgcaga
 8881 cgagagcatc gcagctggtt gcttgtacaa cagcacttgt gacgaccgtg agttcatgtg
 8941 ccagaaccgc cagtgcatcc ccaagcactt cgtgtgtgac cacgaccgtg actgtgcaga
 9001 tggctctgat gagtccccccg agtgtgagta cccgacctgc ggccccagtg agttccgctg
 9061 tgccaatggg cgctgtctga gctcccgcca gtgggagtgt gatggcgaga atgactgcca
 9121 cgaccagagt gacgaggctc ccaagaaccc acactgcacc agccaagagc acaagtgcaa
 9181 tgcctcgtca cagttcctgt gcagcagtgg gcgctgtgtg gctgaggcac tgctctgcaa
 9241 cggccaggat gactgtggcg acagctcgga cgagcgtggc tgccacatca atgagtgtct
 9301 cagccgcaag ctcagtggct gcagccagga ctgtgaggac ctcaagatcg gcttcaagtg
 9361 ccgctgtcgc cctggcttcc ggctgaagga cgacggccgg acgtgtgctg atgtggacga
 9421 gtgcagcacc accttcccct gcagccagcg ctgcatcaac actcatggca gctataagtg
 9481 tctgtgtgtg gagggctatg caccccgcgg cggcgacccc cacagctgca aggctgtgac
 9541 tgacgaggaa ccgtttctga tcttcgccaa ccggtactac ctgcgcaagc tcaacctgga
 9601 cgggtccaac tacacgttac ttaagcaggg cctgaacaac gccgttgcct tggattttga
 9661 ctaccgagag cagatgatct actggacaga tgtgaccacc cagggcagca tgatccgaag
 9721 gatgcacctt aacgggagca atgtgcaggt cctacaccgt acaggcctca gcaaccccga
 9781 tgggctggct gtggactggg tgggtggcaa cctgtactgg tgcgacaaag gccgggacac
 9841 catcgaggtg tccaagctca atggggccta tcggacggtg ctggtcagct ctggcctccg
 9901 tgagcccagg gctctggtgg tggatgtgca gaatgggtac ctgtactgga cagactgggg
 9961 tgaccattca ctgatcggcc gcatcggcat ggatgggtcc agccgcagcg tcatcgtgga
10021 caccaagatc acatggccca atggcctgac gctggactat gtcactgagc gcatctactg
10081 ggccgacgcc cgcgaggact acattgaatt tgccagcctg gatggctcca atcgccacgt
10141 tgtgctgagc caggacatcc cgcacatctt tgcactgacc ctgtttgagg actacgtcta
10201 ctggaccgac tgggaaacaa agtccattaa ccgagcccac aagaccacgg gcaccaacaa
10261 aacgctcctc atcagcacgc tgcaccggcc catggacctg catgtcttcc atgccctgcg
10321 ccagccagac gtgcccaatc acccctgcaa ggtcaacaat ggtggctgca gcaacctgtg
10381 cctgctgtcc cccgggggag ggcacaaatg tgcctgcccc accaacttct acctgggcag
10441 cgatgggcgc acctgtgtgt ccaactgcac ggctagccag tttgtatgca agaacgacaa
10501 gtgcatcccc ttctggtgga agtgtgacac cgaggacgac tgcggggacc actcagacga
10561 gcccccggac tgccctgagt tcaagtgccg gcccggacag ttccagtgct ccacaggtat
10621 ctgcacaaac cctgccttca tctgcgatgg cgacaatgac tgccaggaca acagtgacga
10681 ggccaactgt gacatccacg tctgcttgcc cagtcagttc aaatgcacca acaccaaccg
10741 ctgtattccc ggcatcttcc gctgcaatgg gcaggacaac tgcggagatg gggaggatga
10801 gagggactgc cccgaggtga cctgcgcccc caaccagttc cagtgctcca ttaccaaacg
10861 gtgcatcccc cgggtctggg tctgcgaccg ggacaatgac tgtgtggatg gcagtgatga
10921 gcccgccaac tgcacccaga tgacctgtgg tgtggacgag ttccgctgca aggattcggg
10981 ccgctgcatc ccagcgcgtt ggaagtgtga cggagaggat gactgtgggg atggctcgga
11041 tgagcccaag gaagagtgtg atgaacgcac ctgtgagcca taccagttcc gctgcaagaa
11101 caaccgctgc gtgcccggcc gctggcagtg cgactacgac aacgattgcg gtgacaactc
11161 cgatgaagag agctgcaccc ctcggccctg ctccgagagt gagttctcct gtgccaacgg
11221 ccgctgcatc gcggggcgct ggaaatgcga tggagaccac gactgcgcgg acggctcgga
11281 cgagaaagac tgcacccccc gctgtgacat ggaccagttc cagtgcaaga gcggccactg
11341 catcccccctg cgctggcgct gtgacgcaga cgccgactgc atggacggca gcgacgagga
11401 ggcctgcggc actggcgtgc ggacctgccc cctggacgag ttccagtgca acaacacctt
11461 gtgcaagccg ctggcctgga agtgcgatgg cgaggatgac tgtggggaca actcagatga
11521 gaaccccgag gagtgtgccc ggttcgtgtg ccctcccaac cggcccttcc gttgcaagaa
11581 tgaccgcgtc tgtctgtgga tcgggcgcca atgcgatggc acggacaact gtggggatgg
11641 gactgatgaa gaggactgtg agcccccac agcccacacc acccactgca aagacaagaa
11701 ggagtttctg tgccggaacc agcgctgcct ctcctcctcc ctgcgctgca acatgttcga
11761 tgactgcggg gacggctctg acgaggagga ctgcagcatc gaccccaagc tgaccagctg
11821 cgccaccaat gccagcatct gtggggacga ggcacgctgc gtgcgcaccg agaaagcggc
11881 ctactgtgcc tgccgctcgg gcttccacac cgtgcccggc cagcccggat gccaagacat
11941 caacgagtgc ctgcgcttcg gcacctgctc ccagctctgc aacaacacca agggcggcca
12001 cctctgcagc tgcgctcgga acttcatgaa gacgcacaac acctgcaagg ccgaaggctc
12061 tgagtaccag gtcctgtaca tcgctgatga caatgagatc cgcagcctgt tccccggcca
12121 cccccattcg gcttacgagc aggcattcca gggtgacgag agtgtccgca ttgatgctat
12181 ggatgtccat gtcaaggctg gccgtgtcta ttggaccaac tggcacacgg gcaccatctc
12241 ctaccgcagc ctgccacctg ctgcgcctcc taccacttcc aaccgccacc ggcgacagat
12301 tgaccggggt gtcacccacc tcaacatttc agggctgaag atgcccagag gcatcgccat
12361 cgactgggtg gccggaaacg tgtactggac cgactcgggc cgagatgtga ttgaggtggc
12421 gcagatgaag ggcgagaacc gcaagacgct catctcgggc atgattgacg agccccacgc
12481 cattgtggtg gacccactga gggggaccat gtactggtca gactggggca accaccccaa
12541 gattgagacg gcagcgatgg atgggacgct tcgggagaca ctggtgcagg acaacattca
12601 gtggcccaca ggcctggccg tggattatca caatgagcgg ctgtactggg cagacgccaa
12661 gctttcagtc atcggcagca tccggctcaa tggcacggac cccattgtgg ctgctgacag
```

-continued

SEQUENCE LISTING

```
12721 caaacgaggc ctaagtcacc ccttcagcat cgacgtcttt gaggattaca tctatggtgt
12781 cacctacatc aataatcgtg tcttcaagat ccataagttt ggccacagcc ccttggtcaa
12841 cctgacaggg ggcctgagcc acgcctctga cgtggtcctt taccatcagc acaagcagcc
12901 cgaagtgacc aacccatgtg accgcaagaa atgcgagtgg ctctgcctgc tgagccccag
12961 tgggcctgtc tgcacctgtc ccaatgggaa gcggctggac aacggcacat gcgtgcctgt
13021 gccctctcca acgccccccc cagatgctcc ccggcctgga acctgtaacc tgcagtgctt
13081 caacggtggc agctgtttcc tcaatgcacg gaggcagccc aagtgccgct gccaaccccg
13141 ctacacgggt gacaagtgtg aactggacca gtgctgggag cactgtcgca atgggggcac
13201 ctgtgctgcc tccccctctg gcatgcccac gtgccggtgc cccacgggct tcacgggccc
13261 caaatgcacc cagcaggtgt gtgcgggcta ctgtgccaac aacagcacct gcactgtcaa
13321 ccagggcaac cagccccagt gccgatgcct acccggcttc ctgggcgacc gctgccagta
13381 ccggcagtgc tctggctact gtgagaactt tggcacatgc cagatggctg ctgatggctc
13441 ccgacaatgc cgctgcactg cctactttga gggatcgagg tgtgaggtga acaagtgcag
13501 ccgctgtctc gaagggggcct gtgtggtcaa caagcagagt ggggatgtca cctgcaactg
13561 cacggatggc cgggtggccc ccagctgtct gacctgcgtc ggccactgca gcaatggcgg
13621 ctcctgtacc atgaacagca aaatgatgcc tgagtgccag tgcccacccc acatgacagg
13681 gccccggtgt gaggagcacg tcttcagcca gcagcagcca ggacatatag cctccatcct
13741 aatccctctg ctgttgctgc tgctgctggt tctggtggcc ggagtggtat tctggtataa
13801 gcggcgagtc caaggggcta agggcttcca gcaccaacgg atgaccaacg gggccatgaa
13861 cgtggagatt ggaaaccccca cctacaagat gtacgaaggc ggagagcctg atgatgtggg
13921 aggcctactg gacgctgact ttgccctgga ccctgacaag cccaccaact tcaccaaccc
13981 cgtgtatgcc acactctaca tgggggggcca tggcagtcgc cactccctgg ccagcacgga
14041 cgagaagcga gaactcctgg gccggggccc tgaggacgag ataggggacc ccttggcata
14101 gggccctgcc ccgtcggact gcccccagaa agcctcctgc cccctgccgg tgaagtcctt
14161 cagtgagccc ctccccagcc agcccttccc tggccccgcc ggatgtataa atgtaaaaat
14221 gaaggaatta cattttatat gtgagcgagc aagccggcaa gcgagcacag tattatttct
14281 ccatcccctc cctgcctgct ccttggcacc cccatgctgc cttcagggag acaggcaggg
14341 agggcttggg gctgcacctc ctaccctccc accagaacgc accccactgg gagagctggt
14401 ggtgcagcct tcccctccct gtataagaca ctttgccaag gctctcccct ctcgccccat
14461 ccctgcttgc ccgctcccac agcttcctga gggctaattc tgggaaggga gagttctttg
14521 ctgcccctgt ctggaagacg tggctctggg tgaggtaggc gggaaaggat ggagtgtttt
14581 agttcttggg ggaggccacc ccaaacccca gccccaactc caggggcacc tatgagatgg
14641 ccatgctcaa cccccctccc agacaggccc tccctgtctc cagggccccc accgaggttc
14701 ccagggctgg agacttcctc tggtaaacat tcctccagcc tcccctcccc tggggacgcc
14761 aaggaggtgg gccacaccca ggaagggaaa gcgggcagcc ccgttttggg gacgtgaacg
14821 ttttaataat ttttgctgaa ttcctttaca actaaataac acagatattg ttataaataa
14881 aattgtaaaa aaaaaaaaaa aaaaa
```

Sequence ID No: 2-amino acid sequence of prolow-density-lipoprotein receptor-related protein 1 precursor [*Homo sapiens*]
NCBI Reference Sequence: NP_002323.2

```
   1 mltppllll pllsalvaaa idapktcspk qfacrdqitc iskgwrcdge rdcpdgsdea
  61 peicpqskaq rcqpnehncl gtelcvpmsr lcngvqdcmd gsdegphcre lqgncsrlgc
 121 qhhcvptldg ptcycnssfq lqadgktckd fdecsvygtc sqlctntdgs ficgcvegyl
 181 lqpdnrscka knepvdrppv lliansqnil atylsgaqvs titptstrqt tamdfsyane
 241 tvcwvhvgds aaqtqlkcar mpglkgfvde htinislslh hveqmaidwl tgnfyfvddi
 301 ddrifvcnrn gdtcvtlldl elynpkgial dpamgkvfft dygqipkver cdmdgqnrtk
 361 lvdskivfph gitldlvsrl vywadayldy ievvdyegkg rqtliggill ehlygltvfe
 421 nylyatnsdn anaqqktsvi rvnrfnstey qvvtrvdkgg alhiyhqrrq prvrshacen
 481 dqygkpggcs dicllanshk artcrcrsgf slgsdgksck kpehelflvy gkgrpgiirg
 541 mdmgakvpde hmipienlmn praldfhaet gfiyfadtts yligrqkidg teretilkdg
 601 ihnvegvavd wmgdnlywtd dgpktisva rlekaaqtrk tliegkmthp raivvdping
 661 wmywtdweed pkdsrrgrle rawmdgshrd ifvtsktvlw pnglsldipa grlywvdafy
 721 drietiling tdrkivyegp elnhafglch hgnylfwtey rsgsvyrler gvggapptvt
 781 llrserppif eirmydaqqq qvgtnkcrvn nggcsslcla tpgsrqcaca edqvldadgv
 841 tclanpsyvp ppqcqpgefa cansrciger wkcdgdndcl dnsdeapalc hqhtcpsdrf
 901 kcennrcipn rwlcdgdndc gnsedesnat csartcppnq fscasgrcip iswtcdlddd
 961 cgdrsdesas cayptcfplt qftcnngrci ninwrcdndn dcgdnsdeag cshscsstqf
1021 kcnsgrcipe hwtcdgdndc gdysdethan ctnqatrppg gchtdefqcr ldglciplrw
1081 rcdgdtdcmd ssdekscegv thvcdpsvkf gckdsarcis kawvcdgdnd cednsdeenc
1141 eslacrppsh pcanntsvcl ppdklcdgnd dcgdgsdege lcdqcslnng gcshncsvap
1201 gegivcscpl gmelgpdnht cqiqsycakh lkcsqkcdqn kfsvkcscye gwvlepdges
1261 crsldpfkpf iifsnrheir ridlhkgdys vlvpglrnti aldfhlsqsa lywtdvvedk
1321 iyrgklldng altsfevviq yglatpegla vdwiagniyw vesnldqiev akldgtlrtt
1381 llagdiehpr aialdprdgi lfwtdwdasl prieaasmsg agrrtvhret gsggwpnglt
1441 vdylekrilw idarsdaiys arydgsghme vlrgheflsh pfavtlygge vywtdwrtnt
1501 lakankwtgh nvtvvqrtnt qpfdlqvyhp srqpmapnpc eanggqgpcs hlclinynrt
1561 vscacphlmk lhkdnttcye fkkfllyarq meirgvdlda pyynyiisft vpdidnvtvl
1621 dydareqrvy wsdvrtqaik rafingtgve tvvsadlpna hglavdwvsr nlfwtsydtn
1681 kkqinvarld gsfknavvqg leqphglvvh plrgklywtd gdnismanmd gsnrtllfsg
1741 qkgpvglaid fpesklywis sgnhtinrcn ldgsglevid amrsqlgkat alaimgdklw
1801 wadqvsekmg tcskadgsgs vvlrnsttiv mhmkvydesi qldhkgtnpc svnngdcsql
1861 clptsettrs cmctagyslr sgqqacegvg sfllysvheg irgipldpnd ksdalvpvsg
1921 tslavgidfh aendtiywvd mglstisrak rdqtwredvv tngigrvegi avdwiagniy
1981 wtdqgfdvie varingsfry vvisqgldkp raitvhpekg ylfwtewgqy priersrldg
2041 tervvlvnvs iswpngisvd yqdgklywcd artdkierid letgenrevv lssnnmdmfs
2101 vsvfedfiyw sdrthangsi krgskdnatd svplrtgigv qlkdikvfnr drqkgtnvca
```

-continued

SEQUENCE LISTING

```
2161 vanggcqqlc lyrgrgqrac acahgmlaed gascreyagy llysertilk sihlsdernl
2221 napvqpfedp ehmknviala fdyragtspg tpnriffsdi hfgniqqind dgsrritive
2281 nvgsveglay hrgwdtlywt syttstitrh tvdqtrpgaf eretvitmsg ddhprafvld
2341 ecqnlmfwtn wneqhpsimr aalsganvlt liekdirtpn glaidhraek lyfsdatldk
2401 ierceydgsh ryvilksepv hpfglavyge hifwtdwvrr avqrankhvg snmkllrvdi
2461 pqqpmgiiav andtnscels perinnggcq dlcllthqgh vncscrggri lqddltcrav
2521 nsscraqdef ecangecinf sltcdgvphc kdksdekpsy cnsrrckktf rqcsngrcvs
2581 nmlwcngadd cgdgsdeipc nktacgvgef rcrdgtcign ssrcnqfvdc edasdemncs
2641 atdcssyfrl gvkgvlfqpc ertslcyaps wvcdgandcg dysderdcpg vkrprcplny
2701 facpsgrcip mswtcdkedd cehgedethc nkfcseaqfe cqnhrciskg wlcdgsddcg
2761 dgsdeaahce gktcgpssfs cpgthvcvpe rwlcdgdkdc adgadesiaa gclynstcdd
2821 refmcqnrqc ipkhfvcdhd rdcadgsdes peceyptcgp sefrcangrc lssrqwecdg
2881 endchdqsde apknphctsq ehkcnassqf lcssgrcvae allcngqddc gdssdergch
2941 ineclsrkls gcsqdcedlk igfkcrcrpg frlkddgrtc advdecsttf pcsqrcinth
3001 gsykcicveg yaprggdphs ckavtdeepf lifanryylr klnldgsnyt llkqglnnav
3061 aldfdyreqm iywtdvttqg smirrmhlng snvqvlhrtg lsnpdglavd wvggnlywcd
3121 kgrdtievsk lngayrtvlv ssglrepral vvdvqngyly wtdwgdhsli grigmdgssr
3181 svivdtkitw pngltldyvt eriywadare dyiefasldg snrhvvlsqd iphifaltlf
3241 edyvywtdwe tksinrahkt tgtnktllis tlhrpmdlhv fhalrqpdvp nhpckvnngg
3301 csnlcllspg gghkcacptn fylgsdgrtc vsnctasqfv ckndkcipfw wkcdteddcg
3361 dhsdeppdcp efkcrpgqfq cstgictnpa ficdgdndcq dnsdeancdi hvolpsqfkc
3421 tntnrcipgi frcngqdncg dgederdcpe vtcapnqfqc sitkrcipry wvcdrdndcv
3481 dgsdepanct qmtcgvdefr ckdsgrcipa rwkcdgeddc gdgsdepkee cdertcepyq
3541 frcknnrcvp grwqcdydnd cgdnsdeesc tprpcsesef scangrciag rwkcdgdhdc
3601 adgsdekdct prcdmdqfqc ksghciplrw rcdadadcmd gsdeeacgtg vrtcpldefq
3661 cnntickpla wkcdgeddcg dnsdenpeec arfvcppnrp frckndrvcl wigrqcdgtd
3721 ncgdgtdeed cepptahtth ckdkkeflcr nqrclssslr cnmfddcgdg sdeedcsidp
3781 kltscatnas icgdearcvr tekaaycacr sgfhtvpgqp gcqdineclr fgtcsqlcnn
3841 tkgghlcsca rnfmkthntc kaegseyqvl yiaddneirs lfpghphsay egafqgdesv
3901 ridamdvhvk agrvywtnwh tgtisyrslp paappttsnr hrrgidrgvt hlnisglkmp
3961 rgiaidwvag nvywtdsgrd vievaqmkge nrktlisgmi dephaivvdp lrgtmywsdw
4021 gnhpkietaa mdgtlretiv qdniqwptgl avdyhnerly wadaklsvig siringtdpi
4081 vaadskrgls hpfsidvfed yiygvtyinn rvfkihkfgh splvnitggl shasdvvlyh
4141 qhkqpevtnp cdrkkcewlc llspsgpvct cpngkrldng tcvpvpsptp ppdaprpgtc
4201 nlqcfnggsc flnarrqpkc rcqprytgdk celdqcwehc rnggtcaasp sgmptcrcpt
4261 gftgpkotqg vcagycanns tctvnconqp qcrclpgflg drcqyrqcsg ycenfgtcqm
4321 aadgsrqcrc tayfegsrce vnkcsrcleg acvvnkqsgd vtcnctdgry apscltcvgh
4381 csnggsctmn skmmpecqcp phmtgprcee hvfsqqqpgh iasiliplll llllvlvagv
4441 vfwykrrvqg akgfqhqrmt ngamnveign ptykmyegge pddvgglLda dfaldpdkpt
4501 nftnpvyatl ymgghgsrhs lastdekrel lgrgpedeig dpla
```

Sequence ID No: 3-LRP-1(6-94)
LLLLLPLLSALVAAAIDAPKTCSPKQFACRDQITCISKGWRCDGERDCPDGSDEAPEICPQSKA
QRCQPNEHNCLGTELCVPMSRLCNG Sequence ID No: 4-LRP-1(787-1164)
PPIFEIRMYDAQQQQVGTNKCRVNNGGCSSLCLATPGSRQCACAEDQVLDADGVTCLANPSYVP
PPQCQPGEFACANSRCIQERWKCDGDNDCLDNSDEAPALCHQHTCPSDRFKCENNRCIPNRWLC
DGDNDCGNSEDESNATCSARTCPPNQFSCASGRCIPISWTCDLDDDCGDRSDESASCAYPTCFP
LTQFTCNNGRCININWRCDNDNDCGDNSDEAGCSHSCSSTQFKCNSGRCIPEHWTCDGDNDCGD
YSDETHANCTNQATRPPGGCHTDEFQCRLDGLCIPLRWRCDGDTDCMDSSDEKSCEGVTHVCDP
SVKFGCKDSARCISKAWVCDGDNDCEDNSDEENCESLACRPPSHPCANNTSVCLPPDK Sequence ID No: 5-LRP-1(804-1185)
TNKCRVNNGGCSSLCLATPGSRQCACAEDQVLDADGVTCLANPSYVPPPQCQPGEFACANSRCI
QERWKCDGDNDCLDNSDEAPALCHQHTCPSDRFKCENNRCIPNRWLCDGDNDCGNSEDESNATC
SARTCPPNQFSCASGRCIPISWTCDLDDDCGDRSDESASCAYPTCFPLTQFTCNNGRCININWR
CDNDNDCGDNSDEAGCSHSCSSTQFKCNSGRCIPEHWTCDGDNDCGDYSDETHANCTNQATRPP
GGCHTDEFQCRLDGLCIPLRWRCDGDTDCMDSSDEKSCEGVTHVCDPSVKFGCKDSARCISKAW
VCDGDNDCEDNSDEENCESLACRPPSHPCANNTSVCLPPDKLCDGNDDCGDGSDEGELCDQC Sequence ID No: 6-LRP-1(2462-2923)
QQPMGIIAVANDTNSCELSPCRINNGGCQDLCLLTHQGHVNCSCRGGRILQDDLTCRAVNSSCR
AQDEFECANGECINFSLTCDGVPHCKDKSDEKPSYCNSRRCKKTFRQCSNGRCVSNMLWCNGAD
DCGDGSDEIPCNKTACGVGEFRCRDGTCIGNSSRCNQFVDCEDASDEMNCSATDCSSYFRLGVK
GVLFQPCERTSLCYAPSWVCDGANDCGDYSDERDCPGVKRPRCPLNYFACPSGRCIPMSWTCDK
EDDCEHGEDETHCNKFCSEAQFECQNHRCISKQWLCDGSDDCGDGSDEAAHCEGKTCGPSSFSC
PGTHVCVPERWLCDGDKDCADGADESIAAGCLYNSTCDDREFMCQNRQCIPKHFVCDHDRDCAD
GSDESPECEYPTCGPSEFRCANGRCLSSRQWECDGENDCHDQSDEAPKNPHCTSQEHKCNASSQ
FLCSSGRCVAEALL Sequence ID No: 7-LRP-1(3274-3764)
RPMDLHVFHALRQPDVPNHPCKVNNGGCSNLCLLSPGGGHKCACPTNFYLGSDGRTCVSNCTAS
QFVCKNDKCIPFWWKCDTEDDCGDHSDEPPDCPEFKCRPGQFQCSTGICTNPAFICDGDNDCQD
NSDEANCDIHVCLPSQFKCTNTNRCIPGIFRCNGQDNCGDGEDERDCPEVTCAPNQFQCSITKR
CIPRVWVCDRDNDCVDGSDEPANCTQMTCGVDEFRCKDSGRCIPARWKCDGEDDCGDGSDEPKE
ECDERTCEPYQFRCKNNRCVPGRWQCDYDNDCGDNSDEESCTPRPCSESEFSCANGRCIAGRWK -continued

SEQUENCE LISTING

CDGDHDCADGSDEKDCTPRCDMDQFQCKSGHCIPLRWRCDADADCMDGSDEEACGTGVRTCPLD
EFQCNNTLCKPLAWKCDGEDDCGDNSDENPEECARFVCPPNRPFRCKNDRVCLWIGRQCDGTDN
CGDGTDEEDCEPPTAHTTHCKDKKEFLCRNQRCLSSSLRCNMF

Sequence ID No: 8-LRP-1(3331-3778)
VSNCTASQFVCKNDKCIPFWWKCDTEDDCGDHSDEPPDCPEFKCRPGQFQCSTGICTNPAFICD
GDNDCQDNSDEANCDIHVCLPSQFKCTNTNRCIPGIFRCNGQDNCGDGEDERDCPEVTCAPNQF
QCSITKRCIPRVWVCDRDNDCVDGSDEPANCTQMTCGVDEFRCKDSGRCIPARWKCDGEDDCGD
GSDEPKEECDERTCEPYQFRCKNNRCVPGRWQCDYDNDCGDNSDEESCTPRPCSESEFSCANGR
CIAGRWKCDGDHDCADGSDEKDCTPRCDMDQFQCKSGHCIPLRWRCDADADCMDGSDEEACGTG
VRTCPLDEFQCNNTLCKPLAWKCDGEDDCGDNSDENPEECARFVCPPNRPFRCKNDRVCLWIGR
QCDGTDNCGDGTDEEDCEPPTAHTTHCKDKKEFLCRNQRCLSSSLRCNMFDDCGDGSDEEDCSI

What is claimed is:

1. A method of enhancing nerve growth or neuronal regeneration, comprising contacting a neuron with an inhibitor of low density lipoprotein receptor-related protein-1 (LRP-1) activity in the presence of a myelin-associated inhibitory protein, wherein the inhibitor of LRP-1 activity is receptor associated protein (RAP).

2. The method of claim 1, wherein the neuron is a central nervous system neuron.

3. The method of claim 1, wherein the neuron is in vitro.

4. The method of claim 1, wherein the neuron is in vivo.

5. The method of claim 1, wherein the myelin-associated inhibitory protein is selected from the group consisting of myelin associated glycoprotein (MAG), oligodendrocyte myelin glycoprotein (OMgp), Nogo-A, Nogo-B, Nogo-C, ephrin-B3, Sema4D/CD100, repulsive guidance molecule b, and fragments thereof.

6. The method of claim 1, wherein the inhibitor of LRP-1 activity inhibits binding or endocytosis of myelin.

7. The method of claim 1, wherein the inhibitor of LRP-1 activity inhibits myelin associated glycoprotein (MAG) activation of Rho or association with p75NTR.

8. The method of claim 1, wherein the inhibitor of LRP-1 activity inhibits LRP-1 association with p75NTR.

9. A method of enhancing nerve growth or neuronal regeneration in a subject in need thereof, comprising administering to the subject an effective amount of an inhibitor of low density lipoprotein receptor-related protein-1 (LRP-1) activity, wherein the inhibitor of LRP-1 activity is receptor associated protein (RAP), and further wherein the subject is a human.

10. The method of claim 9, wherein the subject has experienced an injury to the central nervous system.

11. The method of claim 10, wherein the subject has experienced a spinal cord injury.

12. The method of claim 10, wherein the subject has experienced a traumatic brain injury.

13. The method of claim 9, wherein the inhibitor of LRP-1 activity inhibits binding or endocytosis of myelin.

14. The method of claim 9, wherein the inhibitor of LRP-1 activity inhibits myelin associated glycoprotein (MAG) activation of Rho or association with p75NTR.

15. The method of claim 9, wherein the inhibitor of LRP-1 activity inhibits LRP-1 association with p75NTR.

16. The method of claim 10, wherein the inhibitor of LRP-1 activity is administered directly to the injury.

* * * * *

SEQUENCE LISTING

<160> NUMBER OF SEQ ID NOS: 10

<210> SEQ ID NO 1
<211> LENGTH: 14905
<212> TYPE: DNA
<213> ORGANISM: Homo sapiens

<400> SEQUENCE: 1
cagcggtgcg agctccaggc ccatgcactg aggaggcgga aacaagggga gcccccagag 60
ctccatcaag ccccctccaa aggctcccct acccggtcca cgccccccac cccccctccc 120
cgcctcctcc caattgtgca tttttgcagc cggaggcggc tccgagatgg ggctgtgagc 180
ttcgcccggg gaggggggaaa gagcagcgag gagtgaagcg ggggggtggg gtgaagggtt 240
tggatttcgg ggcagggggc gcaccccccgt cagcaggccc tccccaaggg gctcggaact 300
ctacctcttc acccacgccc ctggtgcgct ttgccgaagg aaagaataag aacagagaag 360
gaggaggggg aaaggaggaa aagggggacc ccccaactgg ggggggtgaa ggagagaagt 420
agcaggacca gaggggaagg ggctgctgct tgcatcagcc cacaccatgc tgaccccgcc 480
gttgctcctg ctgctgcccc tgctctcagc tctggtcgcg gcggctatcg acgcccctaa 540
gacttgcagc cccaagcagt ttgcctgcag agatcaaata acctgtatct caaagggctg 600
gcggtgcgac ggtgagaggg actgcccaga cggatctgac gaggcccctg agatttgtcc 660
acagagtaag gcccagcgat gccagccaaa cgagcataac tgcctgggta ctgagctgtg 720
tgttcccatg tcccgcctct gcaatggggt ccaggactgc atggacggct cagatgaggg 780
gccccactgc cgagagctcc aaggcaactg ctctcgcctg ggctgccagc accattgtgt 840
ccccacactc gatgggccca cctgctactg caacagcagc tttcagcttc aggcagatgg 900
caagacctgc aaagattttg atgagtgctc agtgtacggc acctgcagcc agctatgcac 960
caacacagac ggctccttca tatgtggctg tgttgaagga tacctcctgc agccggataa 1020
ccgctcctgc aaggccaaga acgagccagt agaccggccc cctgtgctgt tgatagccaa 1080
ctcccagaac atcttggcca cgtacctgag tggggcccag gtgtctacca tcacacctac 1140
gagcacgcgg cagaccacag ccatggactt cagctatgcc aacgagaccg tatgctgggt 1200
gcatgttggg gacagtgctg ctcagacgca gctcaagtgt gcccgcatgc ctggcctaaa 1260
gggcttcgtg gatgagcaca ccatcaacat ctccctcagt ctgcaccacg tggaacagat 1320
ggccatcgac tggctgacag gcaacttcta ctttgtggat gacatcgatg ataggatctt 1380
tgtctgcaac agaaatgggg acacatgtgt cacattgcta gacctggaac tctacaaccc 1440
caagggcatt gccctggacc ctgccatggg gaaggtgttt ttcactgact atgggcagat 1500

```
cccaaaggtg gaacgctgtg acatggatgg gcagaaccgc accaagctcg tcgacagcaa   1560
gattgtgttt cctcatggca tcacgctgga cctggtcagc cgccttgtct actgggcaga   1620
tgcctatctg gactatattg aagtggtgga ctatgagggc aagggccgcc agaccatcat   1680
ccagggcatc ctgattgagc acctgtacgg cctgactgtg tttgagaatt atctctatgc   1740
caccaactcg gacaatgcca atgcccagca gaagacgagt gtgatccgtg tgaaccgctt   1800
taacagcacc gagtaccagg ttgtcacccg ggtggacaag ggtggtgccc tccacatcta   1860
ccaccagagg cgtcagcccc gagtgaggag ccatgcctgt gaaaacgacc agtatgggaa   1920
gccgggtggc tgctctgaca tctgcctgct ggccaacagc cacaaggcgc ggacctgccg   1980
ctgccgttcc ggcttcagcc tgggcagtga cgggaagtca tgcaagaagc cggagcatga   2040
gctgttcctc gtgtatggca agggccggcc aggcatcatc cggggcatgg atatgggggc   2100
caaggtcccg gatgagcaca tgatccccat tgaaaacctc atgaaccccc gagccctgga   2160
cttccacgct gagaccggct tcatctactt tgccgacacc accagctacc tcattggccg   2220
ccagaagatt gatggcactg agcgggagac catcctgaag gacggcatcc acaatgtgga   2280
gggtgtggcc gtggactgga tgggagacaa tctgtactgg acggacgatg ggcccaaaaa   2340
gacaatcagc gtggccaggc tggagaaagc tgctcagacc cgcaagactt taatcgaggg   2400
caaaatgaca caccccaggg ctattgtggt ggatccactc aatgggtgga tgtactggac   2460
agactgggag gaggacccca aggacagtcg gcgtgggcgg ctggagaggg cgtggatgga   2520
tggctcacac cgagacatct ttgtcacctc caagacagtg ctttggccca atgggctaag   2580
cctggacatc ccggctgggc gcctctactg ggtggatgcc ttctacgacc gcatcgagac   2640
gatactgctc aatggcacag accggaagat tgtgtatgaa ggtcctgagc tgaaccacgc   2700
ctttggcctg tgtcaccatg gcaactacct cttctggact gagtatcgga gtggcagtgt   2760
ctaccgcttg gaacggggtg taggaggcgc accccccact gtgacccttc tgcgcagtga   2820
gcggcccccc atctttgaga tccgaatgta tgatgcccag cagcagcaag ttggcaccaa   2880
caaatgccgg gtgaacaatg gcggctgcag cagcctgtgc ttggccaccc ctgggagccg   2940
ccagtgcgcc tgtgctgagg accaggtgtt ggacgcagac ggcgtcactt gcttggcgaa   3000
cccatcctac gtgcctccac cccagtgcca gccaggcgag tttgcctgtg ccaacagccg   3060
ctgcatccag gagcgctgga agtgtgacgg agacaacgat tgcctggaca acagtgatga   3120
ggccccagcc ctctgccatc agcacacctg cccctcggac cgattcaagt gcgagaacaa   3180
ccggtgcatc cccaaccgct ggctctgcga cggggacaat gactgtggga acagtgaaga   3240
tgagtccaat gccacttgtt cagcccgcac ctgccccccc aaccagttct cctgtgccag   3300
tggccgctgc atccccatct cctggacgtg tgatctggat gacgactgtg gggaccgctc   3360
tgatgagtct gcttcgtgtg cctatcccac ctgcttcccc ctgactcagt ttacctgcaa   3420
caatggcaga tgtatcaaca tcaactggag atgcgacaat gacaatgact gtggggacaa   3480
cagtgacgaa gccggctgca gccactcctg ttctagcacc cagttcaagt gcaacagcgg   3540
gcgttgcatc cccgagcact ggacctgcga tggggacaat gactgcggag actacagtga   3600
tgagacacac gccaactgca ccaaccaggc cacgaggccc cctggtggct gccacactga   3660
tgagttccag tgccggctgg atggactatg catccccctg cggtggcgct gcgatgggga   3720
cactgactgc atggactcca gcgatgagaa gagctgtgag ggagtgaccc acgtctgcga   3780
tcccagtgtc aagtttggct gcaaggactc agctcggtgc atcagcaaag cgtgggtgtg   3840
```

```
tgatggcgac aatgactgtg aggataactc ggacgaggag aactgcgagt ccctggcctg   3900
caggccaccc tcgcaccctt gtgccaacaa cacctcagtc tgcctgcccc ctgacaagct   3960
gtgtgatggc aacgacgact gtggcgacgg ctcagatgag ggcgagctct gcgaccagtg   4020
ctctctgaat aacggtggct gcagccacaa ctgctcagtg gcacctggcg aaggcattgt   4080
gtgttcctgc cctctgggca tggagctggg gcccgacaac cacacctgcc agatccagag   4140
ctactgtgcc aagcatctca aatgcagcca aaagtgcgac cagaacaagt tcagcgtgaa   4200
gtgctcctgc tacgagggct gggtcctgga acctgacggc gagagctgcc gcagcctgga   4260
ccccttcaag ccgttcatca ttttctccaa ccgccatgaa atccggcgca tcgatcttca   4320
caaaggagac tacagcgtcc tggtgcccgg cctgcgcaac accatcgccc tggacttcca   4380
cctcagccag agcgccctct actggaccga cgtggtggag gacaagatct accgcgggaa   4440
gctgctggac aacggagccc tgactagttt cgaggtggtg attcagtatg gcctggccac   4500
acccgagggc ctggctgtag actggattgc aggcaacatc tactgggtgg agagtaacct   4560
ggatcagatc gaggtggcca agctggatgg gaccctccgg accaccctgc tggccggtga   4620
cattgagcac cccaagggca tcgcactgga tccccgggat gggatcctgt tttggacaga   4680
ctgggatgcc agcctgcccc gcattgaggc agcctccatg agtggggctg ggcgccgcac   4740
cgtgcaccgg gagaccggct ctgggggctg gcccaacggg ctcaccgtgg actacctgga   4800
gaagcgcatc ctttggattg acgccaggtc agatgccatt tactcagccc gttacgacgg   4860
ctctggccac atggaggtgc ttcggggaca cgagttcctg tcgcacccgt ttgcagtgac   4920
gctgtacggg ggggaggtct actggactga ctggcgaaca aacacactgg ctaaggccaa   4980
caagtggacc ggccacaatg tcaccgtggt acagaggacc aacacccagc cctttgacct   5040
gcaggtgtac cacccctccc gccagcccat ggctcccaat ccctgtgagg ccaatggggg   5100
ccagggcccc tgctcccacc tgtgtctcat caactacaac cggaccgtgt cctgcgcctg   5160
cccccacctc atgaagctcc acaaggacaa caccacctgc tatgagttta agaagttcct   5220
gctgtacgca cgtcagatgg agatccgagg tgtggacctg gatgctccct actacaacta   5280
catcatctcc ttcacggtgc ccgacatcga caacgtcaca gtgctagact acgatgcccg   5340
cgagcagcgt gtgtactggt ctgacgtgcg gacacaggcc atcaagcggg ccttcatcaa   5400
cggcacaggc gtggagacag tcgtctctgc agacttgcca aatgcccacg ggctggctgt   5460
ggactgggtc tcccgaaacc tgttctggac aagctatgac accaataaga agcagatcaa   5520
tgtggcccgg ctggatggct ccttcaagaa cgcagtggtg cagggcctgg agcagcccca   5580
tggccttgtc gtccaccctc tgcgtgggaa gctctactgg accgatggtg acaacatcag   5640
catggccaac atggatggca gcaatcgcac cctgctcttc agtggccaga agggccccgt   5700
gggcctggct attgacttcc ctgaaagcaa actctactgg atcagctccg ggaaccatac   5760
catcaaccgc tgcaacctgg atgggagtgg gctggaggtc atcgatgcca tgcggagcca   5820
gctgggcaag gccaccgccc tggccatcat gggggacaag ctgtggtggg ctgatcaggt   5880
gtcggaaaag atgggcacat gcagcaaggc tgacggctcg ggctccgtgg tccttcggaa   5940
cagcaccacc ctggtgatgc acatgaaggt ctatgacgag agcatccagc tggaccataa   6000
gggcaccaac ccctgcagtg tcaacaacgg tgactgctcc cagctctgcc tgcccacgtc   6060
agagacgacc cgctcctgca tgtgcacagc cggctatagc ctccggagtg gccagcaggc   6120
ctgcgagggc gtaggttcct ttctcctgta ctctgtgcat gagggaatca ggggaattcc   6180
cctggatccc aatgacaagt cagatgccct ggtcccagtg tccgggacct cgctggctgt   6240
```

```
cggcatcgac ttccacgctg aaaatgacac catctactgg gtggacatgg gcctgagcac   6300
gatcagccgg gccaagcggg accagacgtg gcgtgaagac gtggtgacca atggcattgg   6360
ccgtgtggag ggcattgcag tggactggat cgcaggcaac atctactgga cagaccaggg   6420
ctttgatgtc atcgaggtcg cccggctcaa tggctccttc cgctacgtgg tgatctccca   6480
gggtctagac aagccccggg ccatcaccgt ccacccggag aaagggtact tgttctggac   6540
tgagtggggt cagtatccgc gtattgagcg gtctcggcta gatggcacgg agcgtgtggt   6600
gctggtcaac gtcagcatca gctggcccaa cggcatctca gtggactacc aggatgggaa   6660
gctgtactgg tgcgatgcac ggacagacaa gattgaacgg atcgacctgg agacaggtga   6720
gaaccgcgag gtggttctgt ccagcaacaa catggacatg ttttcagtgt ctgtgtttga   6780
ggatttcatc tactggagtg acaggactca tgccaacggc tctatcaagc gcgggagcaa   6840
agacaatgcc acagactccg tgcccctgcg aaccggcatc ggcgtccagc ttaaagacat   6900
caaagtcttc aaccgggacc ggcagaaagg caccaacgtg tgcgcggtgg ccaatggcgg   6960
gtgccagcag ctgtgcctgt accgggggccg tgggcagcgg gcctgcgcct gtgcccacgg   7020
gatgctggct gaagacggag catcgtgccg cgagtatgcc ggctacctgc tctactcaga   7080
gcgcaccatt ctcaagagta tccacctgtc ggatgagcgc aacctcaatg cgcccgtgca   7140
gcccttcgag gaccctgagc acatgaagaa cgtcatcgcc ctggcctttg actaccgggc   7200
aggcacctct ccgggcaccc ccaatcgcat cttcttcagc gacatccact ttgggaacat   7260
ccaacagatc aacgacgatg gctccaggag gatcaccatt gtggaaaacg tgggctccgt   7320
ggaaggcctg gcctatcacc gtggctggga cactctctat tggacaagct acacgacatc   7380
caccatcacg cgccacacag tggaccagac ccgcccaggg gccttcgagc gtgagaccgt   7440
catcactatg tctggagatg accacccacg ggccttcgtt ttggacgagt gccagaacct   7500
catgttctgg accaactgga atgagcagca tcccagcatc atgcgggcgg cgctctcggg   7560
agccaatgtc ctgaccctta tcgagaagga catccgtacc cccaatggcc tggccatcga   7620
ccaccgtgcc gagaagctct acttctctga cgccaccctg gacaagatcg agcggtgcga   7680
gtatgacggc tcccaccgct atgtgatcct aaagtcagag cctgtccacc ccttcgggct   7740
ggccgtgtat ggggagcaca ttttctggac tgactgggtg cggcgggcag tgcagcgggc   7800
caacaagcac gtgggcagca acatgaagct gctgcgcgtg gacatccccc agcagcccat   7860
gggcatcatc gccgtggcca acgacaccaa cagctgtgaa ctctctccat gccgaatcaa   7920
caacggtggc tgccaggacc tgtgtctgct cactcaccag ggccatgtca actgctcatg   7980
ccgagggggc cgaatcctcc aggatgacct cacctgccga gcggtgaatt cctcttgccg   8040
agcacaagat gagtttgagt gtgccaatgg cgagtgcatc aacttcagcc tgacctgcga   8100
cggcgtcccc cactgcaagg acaagtccga tgagaagcca tcctactgca actcccgccg   8160
ctgcaagaag actttccggc agtgcagcaa tgggcgctgt gtgtccaaca tgctgtggtg   8220
caacggggcc gacgactgtg gggatggctc tgacgagatc ccttgcaaca agacagcctg   8280
tggtgtgggc gagttccgct gccgggacgg gacctgcatc gggaactcca gccgctgcaa   8340
ccagtttgtg gattgtgagg acgcctcaga tgagatgaac tgcagtgcca ccgactgcag   8400
cagctacttc cgcctgggcg tgaagggcgt gctcttccag ccctgcgagc ggacctcact   8460
ctgctacgca cccagctggg tgtgtgatgg cgccaatgac tgtggggact acagtgatga   8520
gcgcgactgc ccaggtgtga aacgccccag atgccctctg aattacttcg cctgccctag   8580
```

```
tgggcgctgc atccccatga gctggacgtg tgacaaagag gatgactgtg aacatggcga   8640
ggacgagacc cactgcaaca agttctgctc agaggcccag tttgagtgcc agaaccatcg   8700
ctgcatctcc aagcagtggc tgtgtgacgg cagcgatgac tgtggggatg gctcagacga   8760
ggctgctcac tgtgaaggca agacgtgcgg cccctcctcc ttctcctgcc ctggcaccca   8820
cgtgtgcgtc cccgagcgct ggctctgtga cggtgacaaa gactgtgctg atggtgcaga   8880
cgagagcatc gcagctggtt gcttgtacaa cagcacttgt gacgaccgtg agttcatgtg   8940
ccagaaccgc cagtgcatcc ccaagcactt cgtgtgtgac cacgaccgtg actgtgcaga   9000
tggctctgat gagtcccccg agtgtgagta cccgacctgc ggccccagtg agttccgctg   9060
tgccaatggg cgctgtctga gctcccgcca gtgggagtgt gatggcgaga atgactgcca   9120
cgaccagagt gacgaggctc ccaagaaccc acactgcacc agccaagagc acaagtgcaa   9180
tgcctcgtca cagttcctgt gcagcagtgg gcgctgtgtg gctgaggcac tgctctgcaa   9240
cggccaggat gactgtggcg acagctcgga cgagcgtggc tgccacatca atgagtgtct   9300
cagccgcaag ctcagtggct gcagccagga ctgtgaggac ctcaagatcg gcttcaagtg   9360
ccgctgtcgc cctggcttcc ggctgaagga cgacggccgg acgtgtgctg atgtggacga   9420
gtgcagcacc accttcccct gcagccagcg ctgcatcaac actcatggca gctataagtg   9480
tctgtgtgtg gagggctatg caccccgcgg cggcgacccc cacagctgca aggctgtgac   9540
tgacgaggaa ccgtttctga tcttcgccaa ccggtactac ctgcgcaagc tcaacctgga   9600
cgggtccaac tacacgttac ttaagcaggg cctgaacaac gccgttgcct tggattttga   9660
ctaccgagag cagatgatct actggacaga tgtgaccacc cagggcagca tgatccgaag   9720
gatgcacctt aacgggagca atgtgcaggt cctacaccgt acaggcctca gcaaccccga   9780
tgggctggct gtggactggg tgggtggcaa cctgtactgg tgcgacaaag gccgggacac   9840
catcgaggtg tccaagctca atggggccta tcggacggtg ctggtcagct ctggcctccg   9900
tgagcccagg gctctggtgg tggatgtgca gaatgggtac ctgtactgga cagactgggg   9960
tgaccattca ctgatcggcc gcatcggcat ggatgggtcc agccgcagcg tcatcgtgga  10020
caccaagatc acatggccca atggcctgac gctggactat gtcactgagc gcatctactg  10080
ggccgacgcc cgcgaggact acattgaatt tgccagcctg gatggctcca atcgccacgt  10140
tgtgctgagc caggacatcc cgcacatctt tgcactgacc ctgtttgagg actacgtcta  10200
ctggaccgac tgggaaacaa agtccattaa ccgagcccac aagaccacgg gcaccaacaa  10260
aacgctcctc atcagcacgc tgcaccggcc catggacctg catgtcttcc atgccctgcg  10320
ccagccagac gtgcccaatc acccctgcaa ggtcaacaat ggtggctgca gcaacctgtg  10380
cctgctgtcc cccgggggag ggcacaaatg tgcctgcccc accaacttct acctgggcag  10440
cgatgggcgc acctgtgtgt ccaactgcac ggctagccag tttgtatgca agaacgacaa  10500
gtgcatcccc ttctggtgga agtgtgacac cgaggacgac tgcggggacc actcagacga  10560
gcccccggac tgccctgagt tcaagtgccg gcccggacag ttccagtgct ccacaggtat  10620
ctgcacaaac cctgccttca tctgcgatgg cgacaatgac tgccaggaca acagtgacga  10680
ggccaactgt gacatccacg tctgcttgcc cagtcagttc aaatgcacca acaccaaccg  10740
ctgtattccc ggcatcttcc gctgcaatgg gcaggacaac tgcggagatg gggaggatga  10800
gagggactgc cccgaggtga cctgcgcccc caaccagttc cagtgctcca ttaccaaacg  10860
gtgcatcccc cgggtctggg tctgcgaccg ggacaatgac tgtgtggatg gcagtgatga  10920
gcccgccaac tgcacccaga tgacctgtgg tgtggacgag ttccgctgca aggattcggg  10980
```

```
ccgctgcatc ccagcgcgtt ggaagtgtga cggagaggat gactgtgggg atggctcgga  11040
tgagcccaag gaagagtgtg atgaacgcac ctgtgagcca taccagttcc gctgcaagaa  11100
caaccgctgc gtgcccggcc gctggcagtg cgactacgac aacgattgcg gtgacaactc  11160
cgatgaagag agctgcaccc ctcggccctg ctccgagagt gagttctcct gtgccaacgg  11220
ccgctgcatc gcggggcgct ggaaatgcga tggagaccac gactgcgcgg acggctcgga  11280
cgagaaagac tgcaccccc gctgtgacat ggaccagttc cagtgcaaga gcggccactg  11340
catccccctg cgctggcgct gtgacgcaga cgccgactgc atggacggca gcgacgagga  11400
ggcctgcggc actggcgtgc ggacctgccc cctggacgag ttccagtgca acaacacctt  11460
gtgcaagccg ctggcctgga agtgcgatgg cgaggatgac tgtggggaca actcagatga  11520
gaaccccgag gagtgtgccc ggttcgtgtg ccctcccaac cggcccttcc gttgcaagaa  11580
tgaccgcgtc tgtctgtgga tcgggcgcca atgcgatggc acggacaact gtggggatgg  11640
gactgatgaa gaggactgtg agcccccac agcccacacc acccactgca aagacaagaa  11700
ggagtttctg tgccggaacc agcgctgcct ctcctcctcc ctgcgctgca acatgttcga  11760
tgactgcggg gacggctctg acgaggagga ctgcagcatc gaccccaagc tgaccagctg  11820
cgccaccaat gccagcatct gtggggacga ggcacgctgc gtgcgcaccg agaaagcggc  11880
ctactgtgcc tgccgctcgg gcttccacac cgtgcccggc cagcccggat gccaagacat  11940
caacgagtgc ctgcgcttcg gcacctgctc ccagctctgc aacaacacca agggcggcca  12000
cctctgcagc tgcgctcgga acttcatgaa gacgcacaac acctgcaagg ccgaaggctc  12060
tgagtaccag gtcctgtaca tcgctgatga caatgagatc cgcagcctgt tccccggcca  12120
cccccattcg gcttacgagc aggcattcca gggtgacgag agtgtccgca ttgatgctat  12180
ggatgtccat gtcaaggctg gccgtgtcta ttggaccaac tggcacacgg gcaccatctc  12240
ctaccgcagc ctgccacctg ctgcgcctcc taccacttcc aaccgccacc ggcgacagat  12300
tgaccggggt gtcacccacc tcaacatttc agggctgaag atgcccagag gcatcgccat  12360
cgactgggtg gccggaaacg tgtactggac cgactcgggc cgagatgtga ttgaggtggc  12420
gcagatgaag ggcgagaacc gcaagacgct catctcgggc atgattgacg agccccacgc  12480
cattgtggtg gacccactga gggggaccat gtactggtca gactggggca accaccccaa  12540
gattgagacg gcagcgatgg atgggacgct tcgggagaca ctggtgcagg acaacattca  12600
gtggcccaca ggcctggccg tggattatca caatgagcgg ctgtactggg cagacgccaa  12660
gctttcagtc atcggcagca tccggctcaa tggcacggac cccattgtgg ctgctgacag  12720
caaacgaggc ctaagtcacc ccttcagcat cgacgtcttt gaggattaca tctatggtgt  12780
cacctacatc aataatcgtg tcttcaagat ccataagttt ggccacagcc ccttggtcaa  12840
cctgacaggg ggcctgagcc acgcctctga cgtggtcctt taccatcagc acaagcagcc  12900
cgaagtgacc aacccatgtg accgcaagaa atgcgagtgg ctctgcctgc tgagccccag  12960
tgggcctgtc tgcacctgtc ccaatgggaa gcggctggac aacggcacat gcgtgcctgt  13020
gccctctcca acgccccccc cagatgctcc ccggcctgga acctgtaacc tgcagtgctt  13080
caacggtggc agctgtttcc tcaatgcacg gaggcagccc aagtgccgct gccaaccccg  13140
ctacacgggt gacaagtgtg aactggacca gtgctgggag cactgtcgca atgggggcac  13200
ctgtgctgcc tccccctctg gcatgcccac gtgccggtgc cccacgggct tcacgggccc  13260
caaatgcacc cagcaggtgt gtgcgggcta ctgtgccaac aacagcacct gcactgtcaa  13320
```

```
ccagggcaac cagccccagt gccgatgcct acccggcttc ctgggcgacc gctgccagta  13380

ccggcagtgc tctggctact gtgagaactt tggcacatgc cagatggctg ctgatggctc  13440

ccgacaatgc cgctgcactg cctactttga gggatcgagg tgtgaggtga acaagtgcag  13500

ccgctgtctc gaaggggcct gtgtggtcaa caagcagagt ggggatgtca cctgcaactg  13560

cacggatggc cgggtggccc ccagctgtct gacctgcgtc ggccactgca gcaatggcgg  13620

ctcctgtacc atgaacagca aaatgatgcc tgagtgccag tgcccacccc acatgacagg  13680

gccccggtgt gaggagcacg tcttcagcca gcagcagcca ggacatatag cctccatcct  13740

aatccctctg ctgttgctgc tgctgctggt tctggtggcc ggagtggtat tctggtataa  13800

gcggcgagtc caaggggcta agggcttcca gcaccaacgg atgaccaacg gggccatgaa  13860

cgtggagatt ggaaacccca cctacaagat gtacgaaggc ggagagcctg atgatgtggg  13920

aggcctactg gacgctgact ttgccctgga ccctgacaag cccaccaact tcaccaaccc  13980

cgtgtatgcc acactctaca tgggggggcca tggcagtcgc cactccctgg ccagcacgga  14040

cgagaagcga gaactcctgg gccggggccc tgaggacgag ataggggacc ccttggcata  14100

gggccctgcc ccgtcggact gcccccagaa agcctcctgc cccctgccgg tgaagtcctt  14160

cagtgagccc ctccccagcc agcccttccc tggccccgcc ggatgtataa atgtaaaaat  14220

gaaggaatta cattttatat gtgagcgagc aagccggcaa gcgagcacag tattatttct  14280

ccatcccctc cctgcctgct ccttggcacc cccatgctgc cttcagggag acaggcaggg  14340

agggcttggg gctgcacctc ctaccctccc accagaacgc accccactgg gagagctggt  14400

ggtgcagcct tcccctccct gtataagaca ctttgccaag gctctcccct ctcgccccat  14460

ccctgcttgc ccgctcccac agcttcctga gggctaattc tgggaaggga gagttctttg  14520

ctgcccctgt ctggaagacg tggctctggg tgaggtaggc gggaaaggat ggagtgtttt  14580

agttcttggg ggaggccacc ccaaacccca gccccaactc caggggcacc tatgagatgg  14640

ccatgctcaa cccccctccc agacaggccc tccctgtctc cagggccccc accgaggttc  14700

ccagggctgg agacttcctc tggtaaacat tcctccagcc tcccctcccc tggggacgcc  14760

aaggaggtgg gccacaccca ggaagggaaa gcgggcagcc ccgttttggg gacgtgaacg  14820

ttttaataat tttgctgaa ttcctttaca actaaataac acagatattg ttataaataa  14880

aattgtaaaa aaaaaaaaaa aaaaa                                         14905
```

```
<210> SEQ ID NO 2
<211> LENGTH: 4544
<212> TYPE: PRT
<213> ORGANISM: Homo sapiens

<400> SEQUENCE: 2

Met Leu Thr Pro Pro Leu Leu Leu Leu Leu Pro Leu Leu Ser Ala Leu
1               5                   10                  15

Val Ala Ala Ala Ile Asp Ala Pro Lys Thr Cys Ser Pro Lys Gln Phe
            20                  25                  30

Ala Cys Arg Asp Gln Ile Thr Cys Ile Ser Lys Gly Trp Arg Cys Asp
        35                  40                  45

Gly Glu Arg Asp Cys Pro Asp Gly Ser Asp Glu Ala Pro Glu Ile Cys
    50                  55                  60

Pro Gln Ser Lys Ala Gln Arg Cys Gln Pro Asn Glu His Asn Cys Leu
65                  70                  75                  80

Gly Thr Glu Leu Cys Val Pro Met Ser Arg Leu Cys Asn Gly Val Gln
                85                  90                  95
```

```
Asp Cys Met Asp Gly Ser Asp Glu Gly Pro His Cys Arg Glu Leu Gln
            100                 105                 110

Gly Asn Cys Ser Arg Leu Gly Cys Gln His His Cys Val Pro Thr Leu
        115                 120                 125

Asp Gly Pro Thr Cys Tyr Cys Asn Ser Ser Phe Gln Leu Gln Ala Asp
    130                 135                 140

Gly Lys Thr Cys Lys Asp Phe Asp Glu Cys Ser Val Tyr Gly Thr Cys
145                 150                 155                 160

Ser Gln Leu Cys Thr Asn Thr Asp Gly Ser Phe Ile Cys Gly Cys Val
                165                 170                 175

Glu Gly Tyr Leu Leu Gln Pro Asp Asn Arg Ser Cys Lys Ala Lys Asn
            180                 185                 190

Glu Pro Val Asp Arg Pro Pro Val Leu Leu Ile Ala Asn Ser Gln Asn
        195                 200                 205

Ile Leu Ala Thr Tyr Leu Ser Gly Ala Gln Val Ser Thr Ile Thr Pro
    210                 215                 220

Thr Ser Thr Arg Gln Thr Thr Ala Met Asp Phe Ser Tyr Ala Asn Glu
225                 230                 235                 240

Thr Val Cys Trp Val His Val Gly Asp Ser Ala Ala Gln Thr Gln Leu
                245                 250                 255

Lys Cys Ala Arg Met Pro Gly Leu Lys Gly Phe Val Asp Glu His Thr
            260                 265                 270

Ile Asn Ile Ser Leu Ser Leu His His Val Glu Gln Met Ala Ile Asp
        275                 280                 285

Trp Leu Thr Gly Asn Phe Tyr Phe Val Asp Asp Ile Asp Asp Arg Ile
    290                 295                 300

Phe Val Cys Asn Arg Asn Gly Asp Thr Cys Val Thr Leu Leu Asp Leu
305                 310                 315                 320

Glu Leu Tyr Asn Pro Lys Gly Ile Ala Leu Asp Pro Ala Met Gly Lys
                325                 330                 335

Val Phe Phe Thr Asp Tyr Gly Gln Ile Pro Lys Val Glu Arg Cys Asp
            340                 345                 350

Met Asp Gly Gln Asn Arg Thr Lys Leu Val Asp Ser Lys Ile Val Phe
        355                 360                 365

Pro His Gly Ile Thr Leu Asp Leu Val Ser Arg Leu Val Tyr Trp Ala
    370                 375                 380

Asp Ala Tyr Leu Asp Tyr Ile Glu Val Val Asp Tyr Glu Gly Lys Gly
385                 390                 395                 400

Arg Gln Thr Ile Ile Gln Gly Ile Leu Ile Glu His Leu Tyr Gly Leu
                405                 410                 415

Thr Val Phe Glu Asn Tyr Leu Tyr Ala Thr Asn Ser Asp Asn Ala Asn
            420                 425                 430

Ala Gln Gln Lys Thr Ser Val Ile Arg Val Asn Arg Phe Asn Ser Thr
        435                 440                 445

Glu Tyr Gln Val Val Thr Arg Val Asp Lys Gly Gly Ala Leu His Ile
    450                 455                 460

Tyr His Gln Arg Arg Gln Pro Arg Val Arg Ser His Ala Cys Glu Asn
465                 470                 475                 480

Asp Gln Tyr Gly Lys Pro Gly Gly Cys Ser Asp Ile Cys Leu Leu Ala
                485                 490                 495

Asn Ser His Lys Ala Arg Thr Cys Arg Cys Arg Ser Gly Phe Ser Leu
            500                 505                 510
```

```
Gly Ser Asp Gly Lys Ser Cys Lys Lys Pro Glu His Glu Leu Phe Leu
        515                 520                 525

Val Tyr Gly Lys Gly Arg Pro Gly Ile Ile Arg Gly Met Asp Met Gly
    530                 535                 540

Ala Lys Val Pro Asp Glu His Met Ile Pro Ile Glu Asn Leu Met Asn
545                 550                 555                 560

Pro Arg Ala Leu Asp Phe His Ala Glu Thr Gly Phe Ile Tyr Phe Ala
                565                 570                 575

Asp Thr Thr Ser Tyr Leu Ile Gly Arg Gln Lys Ile Asp Gly Thr Glu
            580                 585                 590

Arg Glu Thr Ile Leu Lys Asp Gly Ile His Asn Val Glu Gly Val Ala
        595                 600                 605

Val Asp Trp Met Gly Asp Asn Leu Tyr Trp Thr Asp Asp Gly Pro Lys
    610                 615                 620

Lys Thr Ile Ser Val Ala Arg Leu Glu Lys Ala Ala Gln Thr Arg Lys
625                 630                 635                 640

Thr Leu Ile Glu Gly Lys Met Thr His Pro Arg Ala Ile Val Val Asp
                645                 650                 655

Pro Leu Asn Gly Trp Met Tyr Trp Thr Asp Trp Glu Glu Asp Pro Lys
            660                 665                 670

Asp Ser Arg Arg Gly Arg Leu Glu Arg Ala Trp Met Asp Gly Ser His
        675                 680                 685

Arg Asp Ile Phe Val Thr Ser Lys Thr Val Leu Trp Pro Asn Gly Leu
    690                 695                 700

Ser Leu Asp Ile Pro Ala Gly Arg Leu Tyr Trp Val Asp Ala Phe Tyr
705                 710                 715                 720

Asp Arg Ile Glu Thr Ile Leu Leu Asn Gly Thr Asp Arg Lys Ile Val
                725                 730                 735

Tyr Glu Gly Pro Glu Leu Asn His Ala Phe Gly Leu Cys His His Gly
            740                 745                 750

Asn Tyr Leu Phe Trp Thr Glu Tyr Arg Ser Gly Ser Val Tyr Arg Leu
        755                 760                 765

Glu Arg Gly Val Gly Gly Ala Pro Pro Thr Val Thr Leu Leu Arg Ser
    770                 775                 780

Glu Arg Pro Pro Ile Phe Glu Ile Arg Met Tyr Asp Ala Gln Gln Gln
785                 790                 795                 800

Gln Val Gly Thr Asn Lys Cys Arg Val Asn Asn Gly Gly Cys Ser Ser
                805                 810                 815

Leu Cys Leu Ala Thr Pro Gly Ser Arg Gln Cys Ala Cys Ala Glu Asp
            820                 825                 830

Gln Val Leu Asp Ala Asp Gly Val Thr Cys Leu Ala Asn Pro Ser Tyr
        835                 840                 845

Val Pro Pro Pro Gln Cys Gln Pro Gly Glu Phe Ala Cys Ala Asn Ser
    850                 855                 860

Arg Cys Ile Gln Glu Arg Trp Lys Cys Asp Gly Asp Asn Asp Cys Leu
865                 870                 875                 880

Asp Asn Ser Asp Glu Ala Pro Ala Leu Cys His Gln His Thr Cys Pro
                885                 890                 895

Ser Asp Arg Phe Lys Cys Glu Asn Asn Arg Cys Ile Pro Asn Arg Trp
            900                 905                 910

Leu Cys Asp Gly Asp Asn Asp Cys Gly Asn Ser Glu Asp Glu Ser Asn
        915                 920                 925

Ala Thr Cys Ser Ala Arg Thr Cys Pro Pro Asn Gln Phe Ser Cys Ala
```

```
930                 935                 940

Ser Gly Arg Cys Ile Pro Ile Ser Trp Thr Cys Asp Leu Asp Asp Asp
945                 950                 955                 960

Cys Gly Asp Arg Ser Asp Glu Ser Ala Ser Cys Ala Tyr Pro Thr Cys
                965                 970                 975

Phe Pro Leu Thr Gln Phe Thr Cys Asn Asn Gly Arg Cys Ile Asn Ile
            980                 985                 990

Asn Trp Arg Cys Asp Asn Asp Asn  Asp Cys Gly Asp Asn  Ser Asp Glu
        995                 1000                1005

Ala Gly  Cys Ser His Ser Cys  Ser Ser Thr Gln Phe  Lys Cys Asn
    1010                1015                1020

Ser Gly  Arg Cys Ile Pro Glu  His Trp Thr Cys Asp  Gly Asp Asn
    1025                1030                1035

Asp Cys  Gly Asp Tyr Ser Asp  Glu Thr His Ala Asn  Cys Thr Asn
    1040                1045                1050

Gln Ala  Thr Arg Pro Pro Gly  Gly Cys His Thr Asp  Glu Phe Gln
    1055                1060                1065

Cys Arg  Leu Asp Gly Leu Cys  Ile Pro Leu Arg Trp  Arg Cys Asp
    1070                1075                1080

Gly Asp  Thr Asp Cys Met Asp  Ser Ser Asp Glu Lys  Ser Cys Glu
    1085                1090                1095

Gly Val  Thr His Val Cys Asp  Pro Ser Val Lys Phe  Gly Cys Lys
    1100                1105                1110

Asp Ser  Ala Arg Cys Ile Ser  Lys Ala Trp Val Cys  Asp Gly Asp
    1115                1120                1125

Asn Asp  Cys Glu Asp Asn Ser  Asp Glu Glu Asn Cys  Glu Ser Leu
    1130                1135                1140

Ala Cys  Arg Pro Pro Ser His  Pro Cys Ala Asn Asn  Thr Ser Val
    1145                1150                1155

Cys Leu  Pro Pro Asp Lys Leu  Cys Asp Gly Asn Asp  Asp Cys Gly
    1160                1165                1170

Asp Gly  Ser Asp Glu Gly Glu  Leu Cys Asp Gln Cys  Ser Leu Asn
    1175                1180                1185

Asn Gly  Gly Cys Ser His Asn  Cys Ser Val Ala Pro  Gly Glu Gly
    1190                1195                1200

Ile Val  Cys Ser Cys Pro Leu  Gly Met Glu Leu Gly  Pro Asp Asn
    1205                1210                1215

His Thr  Cys Gln Ile Gln Ser  Tyr Cys Ala Lys His  Leu Lys Cys
    1220                1225                1230

Ser Gln  Lys Cys Asp Gln Asn  Lys Phe Ser Val Lys  Cys Ser Cys
    1235                1240                1245

Tyr Glu  Gly Trp Val Leu Glu  Pro Asp Gly Glu Ser  Cys Arg Ser
    1250                1255                1260

Leu Asp  Pro Phe Lys Pro Phe  Ile Ile Phe Ser Asn  Arg His Glu
    1265                1270                1275

Ile Arg  Arg Ile Asp Leu His  Lys Gly Asp Tyr Ser  Val Leu Val
    1280                1285                1290

Pro Gly  Leu Arg Asn Thr Ile  Ala Leu Asp Phe His  Leu Ser Gln
    1295                1300                1305

Ser Ala  Leu Tyr Trp Thr Asp  Val Val Glu Asp Lys  Ile Tyr Arg
    1310                1315                1320

Gly Lys  Leu Leu Asp Asn Gly  Ala Leu Thr Ser Phe  Glu Val Val
    1325                1330                1335
```

```
Ile Gln  Tyr Gly Leu Ala Thr  Pro Glu Gly Leu Ala  Val Asp Trp
    1340                 1345                 1350

Ile Ala  Gly Asn Ile Tyr Trp  Val Glu Ser Asn Leu  Asp Gln Ile
    1355                 1360                 1365

Glu Val  Ala Lys Leu Asp Gly  Thr Leu Arg Thr Thr  Leu Leu Ala
    1370                 1375                 1380

Gly Asp  Ile Glu His Pro Arg  Ala Ile Ala Leu Asp  Pro Arg Asp
    1385                 1390                 1395

Gly Ile  Leu Phe Trp Thr Asp  Trp Asp Ala Ser Leu  Pro Arg Ile
    1400                 1405                 1410

Glu Ala  Ala Ser Met Ser Gly  Ala Gly Arg Arg Thr  Val His Arg
    1415                 1420                 1425

Glu Thr  Gly Ser Gly Gly Trp  Pro Asn Gly Leu Thr  Val Asp Tyr
    1430                 1435                 1440

Leu Glu  Lys Arg Ile Leu Trp  Ile Asp Ala Arg Ser  Asp Ala Ile
    1445                 1450                 1455

Tyr Ser  Ala Arg Tyr Asp Gly  Ser Gly His Met Glu  Val Leu Arg
    1460                 1465                 1470

Gly His  Glu Phe Leu Ser His  Pro Phe Ala Val Thr  Leu Tyr Gly
    1475                 1480                 1485

Gly Glu  Val Tyr Trp Thr Asp  Trp Arg Thr Asn Thr  Leu Ala Lys
    1490                 1495                 1500

Ala Asn  Lys Trp Thr Gly His  Asn Val Thr Val Val  Gln Arg Thr
    1505                 1510                 1515

Asn Thr  Gln Pro Phe Asp Leu  Gln Val Tyr His Pro  Ser Arg Gln
    1520                 1525                 1530

Pro Met  Ala Pro Asn Pro Cys  Glu Ala Asn Gly Gly  Gln Gly Pro
    1535                 1540                 1545

Cys Ser  His Leu Cys Leu Ile  Asn Tyr Asn Arg Thr  Val Ser Cys
    1550                 1555                 1560

Ala Cys  Pro His Leu Met Lys  Leu His Lys Asp Asn  Thr Thr Cys
    1565                 1570                 1575

Tyr Glu  Phe Lys Lys Phe Leu  Leu Tyr Ala Arg Gln  Met Glu Ile
    1580                 1585                 1590

Arg Gly  Val Asp Leu Asp Ala  Pro Tyr Tyr Asn Tyr  Ile Ile Ser
    1595                 1600                 1605

Phe Thr  Val Pro Asp Ile Asp  Asn Val Thr Val Leu  Asp Tyr Asp
    1610                 1615                 1620

Ala Arg  Glu Gln Arg Val Tyr  Trp Ser Asp Val Arg  Thr Gln Ala
    1625                 1630                 1635

Ile Lys  Arg Ala Phe Ile Asn  Gly Thr Gly Val Glu  Thr Val Val
    1640                 1645                 1650

Ser Ala  Asp Leu Pro Asn Ala  His Gly Leu Ala Val  Asp Trp Val
    1655                 1660                 1665

Ser Arg  Asn Leu Phe Trp Thr  Ser Tyr Asp Thr Asn  Lys Lys Gln
    1670                 1675                 1680

Ile Asn  Val Ala Arg Leu Asp  Gly Ser Phe Lys Asn  Ala Val Val
    1685                 1690                 1695

Gln Gly  Leu Glu Gln Pro His  Gly Leu Val Val His  Pro Leu Arg
    1700                 1705                 1710

Gly Lys  Leu Tyr Trp Thr Asp  Gly Asp Asn Ile Ser  Met Ala Asn
    1715                 1720                 1725
```

```
Met Asp  Gly Ser Asn Arg Thr  Leu Leu Phe Ser Gly  Gln Lys Gly
    1730                 1735                 1740

Pro Val  Gly Leu Ala Ile Asp  Phe Pro Glu Ser Lys  Leu Tyr Trp
    1745                 1750                 1755

Ile Ser  Ser Gly Asn His Thr  Ile Asn Arg Cys Asn  Leu Asp Gly
    1760                 1765                 1770

Ser Gly  Leu Glu Val Ile Asp  Ala Met Arg Ser Gln  Leu Gly Lys
    1775                 1780                 1785

Ala Thr  Ala Leu Ala Ile Met  Gly Asp Lys Leu Trp  Trp Ala Asp
    1790                 1795                 1800

Gln Val  Ser Glu Lys Met Gly  Thr Cys Ser Lys Ala  Asp Gly Ser
    1805                 1810                 1815

Gly Ser  Val Val Leu Arg Asn  Ser Thr Thr Leu Val  Met His Met
    1820                 1825                 1830

Lys Val  Tyr Asp Glu Ser Ile  Gln Leu Asp His Lys  Gly Thr Asn
    1835                 1840                 1845

Pro Cys  Ser Val Asn Asn Gly  Asp Cys Ser Gln Leu  Cys Leu Pro
    1850                 1855                 1860

Thr Ser  Glu Thr Thr Arg Ser  Cys Met Cys Thr Ala  Gly Tyr Ser
    1865                 1870                 1875

Leu Arg  Ser Gly Gln Gln Ala  Cys Glu Gly Val Gly  Ser Phe Leu
    1880                 1885                 1890

Leu Tyr  Ser Val His Glu Gly  Ile Arg Gly Ile Pro  Leu Asp Pro
    1895                 1900                 1905

Asn Asp  Lys Ser Asp Ala Leu  Val Pro Val Ser Gly  Thr Ser Leu
    1910                 1915                 1920

Ala Val  Gly Ile Asp Phe His  Ala Glu Asn Asp Thr  Ile Tyr Trp
    1925                 1930                 1935

Val Asp  Met Gly Leu Ser Thr  Ile Ser Arg Ala Lys  Arg Asp Gln
    1940                 1945                 1950

Thr Trp  Arg Glu Asp Val Val  Thr Asn Gly Ile Gly  Arg Val Glu
    1955                 1960                 1965

Gly Ile  Ala Val Asp Trp Ile  Ala Gly Asn Ile Tyr  Trp Thr Asp
    1970                 1975                 1980

Gln Gly  Phe Asp Val Ile Glu  Val Ala Arg Leu Asn  Gly Ser Phe
    1985                 1990                 1995

Arg Tyr  Val Val Ile Ser Gln  Gly Leu Asp Lys Pro  Arg Ala Ile
    2000                 2005                 2010

Thr Val  His Pro Glu Lys Gly  Tyr Leu Phe Trp Thr  Glu Trp Gly
    2015                 2020                 2025

Gln Tyr  Pro Arg Ile Glu Arg  Ser Arg Leu Asp Gly  Thr Glu Arg
    2030                 2035                 2040

Val Val  Leu Val Asn Val Ser  Ile Ser Trp Pro Asn  Gly Ile Ser
    2045                 2050                 2055

Val Asp  Tyr Gln Asp Gly Lys  Leu Tyr Trp Cys Asp  Ala Arg Thr
    2060                 2065                 2070

Asp Lys  Ile Glu Arg Ile Asp  Leu Glu Thr Gly Glu  Asn Arg Glu
    2075                 2080                 2085

Val Val  Leu Ser Ser Asn Asn  Met Asp Met Phe Ser  Val Ser Val
    2090                 2095                 2100

Phe Glu  Asp Phe Ile Tyr Trp  Ser Asp Arg Thr His  Ala Asn Gly
    2105                 2110                 2115

Ser Ile  Lys Arg Gly Ser Lys  Asp Asn Ala Thr Asp  Ser Val Pro
```

```
    2120                2125                2130

Leu Arg  Thr Gly Ile Gly Val  Gln Leu Lys Asp Ile  Lys Val Phe
    2135                2140                2145

Asn Arg  Asp Arg Gln Lys Gly  Thr Asn Val Cys Ala  Val Ala Asn
    2150                2155                2160

Gly Gly  Cys Gln Gln Leu Cys  Leu Tyr Arg Gly Arg  Gly Gln Arg
    2165                2170                2175

Ala Cys  Ala Cys Ala His Gly  Met Leu Ala Glu Asp  Gly Ala Ser
    2180                2185                2190

Cys Arg  Glu Tyr Ala Gly Tyr  Leu Leu Tyr Ser Glu  Arg Thr Ile
    2195                2200                2205

Leu Lys  Ser Ile His Leu Ser  Asp Glu Arg Asn Leu  Asn Ala Pro
    2210                2215                2220

Val Gln  Pro Phe Glu Asp Pro  Glu His Met Lys Asn  Val Ile Ala
    2225                2230                2235

Leu Ala  Phe Asp Tyr Arg Ala  Gly Thr Ser Pro Gly  Thr Pro Asn
    2240                2245                2250

Arg Ile  Phe Phe Ser Asp Ile  His Phe Gly Asn Ile  Gln Gln Ile
    2255                2260                2265

Asn Asp  Asp Gly Ser Arg Arg  Ile Thr Ile Val Glu  Asn Val Gly
    2270                2275                2280

Ser Val  Glu Gly Leu Ala Tyr  His Arg Gly Trp Asp  Thr Leu Tyr
    2285                2290                2295

Trp Thr  Ser Tyr Thr Thr Ser  Thr Ile Thr Arg His  Thr Val Asp
    2300                2305                2310

Gln Thr  Arg Pro Gly Ala Phe  Glu Arg Glu Thr Val  Ile Thr Met
    2315                2320                2325

Ser Gly  Asp Asp His Pro Arg  Ala Phe Val Leu Asp  Glu Cys Gln
    2330                2335                2340

Asn Leu  Met Phe Trp Thr Asn  Trp Asn Glu Gln His  Pro Ser Ile
    2345                2350                2355

Met Arg  Ala Ala Leu Ser Gly  Ala Asn Val Leu Thr  Leu Ile Glu
    2360                2365                2370

Lys Asp  Ile Arg Thr Pro Asn  Gly Leu Ala Ile Asp  His Arg Ala
    2375                2380                2385

Glu Lys  Leu Tyr Phe Ser Asp  Ala Thr Leu Asp Lys  Ile Glu Arg
    2390                2395                2400

Cys Glu  Tyr Asp Gly Ser His  Arg Tyr Val Ile Leu  Lys Ser Glu
    2405                2410                2415

Pro Val  His Pro Phe Gly Leu  Ala Val Tyr Gly Glu  His Ile Phe
    2420                2425                2430

Trp Thr  Asp Trp Val Arg Arg  Ala Val Gln Arg Ala  Asn Lys His
    2435                2440                2445

Val Gly  Ser Asn Met Lys Leu  Leu Arg Val Asp Ile  Pro Gln Gln
    2450                2455                2460

Pro Met  Gly Ile Ile Ala Val  Ala Asn Asp Thr Asn  Ser Cys Glu
    2465                2470                2475

Leu Ser  Pro Cys Arg Ile Asn  Asn Gly Gly Cys Gln  Asp Leu Cys
    2480                2485                2490

Leu Leu  Thr His Gln Gly His  Val Asn Cys Ser Cys  Arg Gly Gly
    2495                2500                2505

Arg Ile  Leu Gln Asp Asp Leu  Thr Cys Arg Ala Val  Asn Ser Ser
    2510                2515                2520
```

```
Cys Arg Ala Gln Asp Glu Phe Glu Cys Ala Asn Gly Glu Cys Ile
    2525                2530                2535

Asn Phe Ser Leu Thr Cys Asp Gly Val Pro His Cys Lys Asp Lys
    2540                2545                2550

Ser Asp Glu Lys Pro Ser Tyr Cys Asn Ser Arg Arg Cys Lys Lys
    2555                2560                2565

Thr Phe Arg Gln Cys Ser Asn Gly Arg Cys Val Ser Asn Met Leu
    2570                2575                2580

Trp Cys Asn Gly Ala Asp Asp Cys Gly Asp Gly Ser Asp Glu Ile
    2585                2590                2595

Pro Cys Asn Lys Thr Ala Cys Gly Val Gly Glu Phe Arg Cys Arg
    2600                2605                2610

Asp Gly Thr Cys Ile Gly Asn Ser Ser Arg Cys Asn Gln Phe Val
    2615                2620                2625

Asp Cys Glu Asp Ala Ser Asp Glu Met Asn Cys Ser Ala Thr Asp
    2630                2635                2640

Cys Ser Ser Tyr Phe Arg Leu Gly Val Lys Gly Val Leu Phe Gln
    2645                2650                2655

Pro Cys Glu Arg Thr Ser Leu Cys Tyr Ala Pro Ser Trp Val Cys
    2660                2665                2670

Asp Gly Ala Asn Asp Cys Gly Asp Tyr Ser Asp Glu Arg Asp Cys
    2675                2680                2685

Pro Gly Val Lys Arg Pro Arg Cys Pro Leu Asn Tyr Phe Ala Cys
    2690                2695                2700

Pro Ser Gly Arg Cys Ile Pro Met Ser Trp Thr Cys Asp Lys Glu
    2705                2710                2715

Asp Asp Cys Glu His Gly Glu Asp Glu Thr His Cys Asn Lys Phe
    2720                2725                2730

Cys Ser Glu Ala Gln Phe Glu Cys Gln Asn His Arg Cys Ile Ser
    2735                2740                2745

Lys Gln Trp Leu Cys Asp Gly Ser Asp Asp Cys Gly Asp Gly Ser
    2750                2755                2760

Asp Glu Ala Ala His Cys Glu Gly Lys Thr Cys Gly Pro Ser Ser
    2765                2770                2775

Phe Ser Cys Pro Gly Thr His Val Cys Val Pro Glu Arg Trp Leu
    2780                2785                2790

Cys Asp Gly Asp Lys Asp Cys Ala Asp Gly Ala Asp Glu Ser Ile
    2795                2800                2805

Ala Ala Gly Cys Leu Tyr Asn Ser Thr Cys Asp Asp Arg Glu Phe
    2810                2815                2820

Met Cys Gln Asn Arg Gln Cys Ile Pro Lys His Phe Val Cys Asp
    2825                2830                2835

His Asp Arg Asp Cys Ala Asp Gly Ser Asp Glu Ser Pro Glu Cys
    2840                2845                2850

Glu Tyr Pro Thr Cys Gly Pro Ser Glu Phe Arg Cys Ala Asn Gly
    2855                2860                2865

Arg Cys Leu Ser Ser Arg Gln Trp Glu Cys Asp Gly Glu Asn Asp
    2870                2875                2880

Cys His Asp Gln Ser Asp Glu Ala Pro Lys Asn Pro His Cys Thr
    2885                2890                2895

Ser Gln Glu His Lys Cys Asn Ala Ser Ser Gln Phe Leu Cys Ser
    2900                2905                2910
```

```
Ser Gly  Arg Cys Val Ala Glu  Ala Leu Leu Cys Asn  Gly Gln Asp
    2915                 2920                 2925

Asp Cys  Gly Asp Ser Ser Asp  Glu Arg Gly Cys His  Ile Asn Glu
    2930                 2935                 2940

Cys Leu  Ser Arg Lys Leu Ser  Gly Cys Ser Gln Asp  Cys Glu Asp
    2945                 2950                 2955

Leu Lys  Ile Gly Phe Lys Cys  Arg Cys Arg Pro Gly  Phe Arg Leu
    2960                 2965                 2970

Lys Asp  Asp Gly Arg Thr Cys  Ala Asp Val Asp Glu  Cys Ser Thr
    2975                 2980                 2985

Thr Phe  Pro Cys Ser Gln Arg  Cys Ile Asn Thr His  Gly Ser Tyr
    2990                 2995                 3000

Lys Cys  Leu Cys Val Glu Gly  Tyr Ala Pro Arg Gly  Gly Asp Pro
    3005                 3010                 3015

His Ser  Cys Lys Ala Val Thr  Asp Glu Glu Pro Phe  Leu Ile Phe
    3020                 3025                 3030

Ala Asn  Arg Tyr Tyr Leu Arg  Lys Leu Asn Leu Asp  Gly Ser Asn
    3035                 3040                 3045

Tyr Thr  Leu Leu Lys Gln Gly  Leu Asn Asn Ala Val  Ala Leu Asp
    3050                 3055                 3060

Phe Asp  Tyr Arg Glu Gln Met  Ile Tyr Trp Thr Asp  Val Thr Thr
    3065                 3070                 3075

Gln Gly  Ser Met Ile Arg Arg  Met His Leu Asn Gly  Ser Asn Val
    3080                 3085                 3090

Gln Val  Leu His Arg Thr Gly  Leu Ser Asn Pro Asp  Gly Leu Ala
    3095                 3100                 3105

Val Asp  Trp Val Gly Gly Asn  Leu Tyr Trp Cys Asp  Lys Gly Arg
    3110                 3115                 3120

Asp Thr  Ile Glu Val Ser Lys  Leu Asn Gly Ala Tyr  Arg Thr Val
    3125                 3130                 3135

Leu Val  Ser Ser Gly Leu Arg  Glu Pro Arg Ala Leu  Val Val Asp
    3140                 3145                 3150

Val Gln  Asn Gly Tyr Leu Tyr  Trp Thr Asp Trp Gly  Asp His Ser
    3155                 3160                 3165

Leu Ile  Gly Arg Ile Gly Met  Asp Gly Ser Ser Arg  Ser Val Ile
    3170                 3175                 3180

Val Asp  Thr Lys Ile Thr Trp  Pro Asn Gly Leu Thr  Leu Asp Tyr
    3185                 3190                 3195

Val Thr  Glu Arg Ile Tyr Trp  Ala Asp Ala Arg Glu  Asp Tyr Ile
    3200                 3205                 3210

Glu Phe  Ala Ser Leu Asp Gly  Ser Asn Arg His Val  Val Leu Ser
    3215                 3220                 3225

Gln Asp  Ile Pro His Ile Phe  Ala Leu Thr Leu Phe  Glu Asp Tyr
    3230                 3235                 3240

Val Tyr  Trp Thr Asp Trp Glu  Thr Lys Ser Ile Asn  Arg Ala His
    3245                 3250                 3255

Lys Thr  Thr Gly Thr Asn Lys  Thr Leu Leu Ile Ser  Thr Leu His
    3260                 3265                 3270

Arg Pro  Met Asp Leu His Val  Phe His Ala Leu Arg  Gln Pro Asp
    3275                 3280                 3285

Val Pro  Asn His Pro Cys Lys  Val Asn Asn Gly Gly  Cys Ser Asn
    3290                 3295                 3300

Leu Cys  Leu Leu Ser Pro Gly  Gly Gly His Lys Cys  Ala Cys Pro
```

```
    3305                3310                3315

Thr Asn Phe Tyr Leu Gly Ser Asp Gly Arg Thr Cys Val Ser Asn
    3320                3325                3330

Cys Thr Ala Ser Gln Phe Val Cys Lys Asn Asp Lys Cys Ile Pro
    3335                3340                3345

Phe Trp Trp Lys Cys Asp Thr Glu Asp Asp Cys Gly Asp His Ser
    3350                3355                3360

Asp Glu Pro Pro Asp Cys Pro Glu Phe Lys Cys Arg Pro Gly Gln
    3365                3370                3375

Phe Gln Cys Ser Thr Gly Ile Cys Thr Asn Pro Ala Phe Ile Cys
    3380                3385                3390

Asp Gly Asp Asn Asp Cys Gln Asp Asn Ser Asp Glu Ala Asn Cys
    3395                3400                3405

Asp Ile His Val Cys Leu Pro Ser Gln Phe Lys Cys Thr Asn Thr
    3410                3415                3420

Asn Arg Cys Ile Pro Gly Ile Phe Arg Cys Asn Gly Gln Asp Asn
    3425                3430                3435

Cys Gly Asp Gly Glu Asp Glu Arg Asp Cys Pro Glu Val Thr Cys
    3440                3445                3450

Ala Pro Asn Gln Phe Gln Cys Ser Ile Thr Lys Arg Cys Ile Pro
    3455                3460                3465

Arg Val Trp Val Cys Asp Arg Asp Asn Asp Cys Val Asp Gly Ser
    3470                3475                3480

Asp Glu Pro Ala Asn Cys Thr Gln Met Thr Cys Gly Val Asp Glu
    3485                3490                3495

Phe Arg Cys Lys Asp Ser Gly Arg Cys Ile Pro Ala Arg Trp Lys
    3500                3505                3510

Cys Asp Gly Glu Asp Asp Cys Gly Asp Gly Ser Asp Glu Pro Lys
    3515                3520                3525

Glu Glu Cys Asp Glu Arg Thr Cys Glu Pro Tyr Gln Phe Arg Cys
    3530                3535                3540

Lys Asn Asn Arg Cys Val Pro Gly Arg Trp Gln Cys Asp Tyr Asp
    3545                3550                3555

Asn Asp Cys Gly Asp Asn Ser Asp Glu Glu Ser Cys Thr Pro Arg
    3560                3565                3570

Pro Cys Ser Glu Ser Glu Phe Ser Cys Ala Asn Gly Arg Cys Ile
    3575                3580                3585

Ala Gly Arg Trp Lys Cys Asp Gly Asp His Asp Cys Ala Asp Gly
    3590                3595                3600

Ser Asp Glu Lys Asp Cys Thr Pro Arg Cys Asp Met Asp Gln Phe
    3605                3610                3615

Gln Cys Lys Ser Gly His Cys Ile Pro Leu Arg Trp Arg Cys Asp
    3620                3625                3630

Ala Asp Ala Asp Cys Met Asp Gly Ser Asp Glu Glu Ala Cys Gly
    3635                3640                3645

Thr Gly Val Arg Thr Cys Pro Leu Asp Glu Phe Gln Cys Asn Asn
    3650                3655                3660

Thr Leu Cys Lys Pro Leu Ala Trp Lys Cys Asp Gly Glu Asp Asp
    3665                3670                3675

Cys Gly Asp Asn Ser Asp Glu Asn Pro Glu Glu Cys Ala Arg Phe
    3680                3685                3690

Val Cys Pro Pro Asn Arg Pro Phe Arg Cys Lys Asn Asp Arg Val
    3695                3700                3705
```

```
Cys Leu Trp Ile Gly Arg Gln Cys Asp Gly Thr Asp Asn Cys Gly
    3710                3715                3720

Asp Gly Thr Asp Glu Glu Asp Cys Glu Pro Pro Thr Ala His Thr
    3725                3730                3735

Thr His Cys Lys Asp Lys Lys Glu Phe Leu Cys Arg Asn Gln Arg
    3740                3745                3750

Cys Leu Ser Ser Ser Leu Arg Cys Asn Met Phe Asp Asp Cys Gly
    3755                3760                3765

Asp Gly Ser Asp Glu Glu Asp Cys Ser Ile Asp Pro Lys Leu Thr
    3770                3775                3780

Ser Cys Ala Thr Asn Ala Ser Ile Cys Gly Asp Glu Ala Arg Cys
    3785                3790                3795

Val Arg Thr Glu Lys Ala Ala Tyr Cys Ala Cys Arg Ser Gly Phe
    3800                3805                3810

His Thr Val Pro Gly Gln Pro Gly Cys Gln Asp Ile Asn Glu Cys
    3815                3820                3825

Leu Arg Phe Gly Thr Cys Ser Gln Leu Cys Asn Asn Thr Lys Gly
    3830                3835                3840

Gly His Leu Cys Ser Cys Ala Arg Asn Phe Met Lys Thr His Asn
    3845                3850                3855

Thr Cys Lys Ala Glu Gly Ser Glu Tyr Gln Val Leu Tyr Ile Ala
    3860                3865                3870

Asp Asp Asn Glu Ile Arg Ser Leu Phe Pro Gly His Pro His Ser
    3875                3880                3885

Ala Tyr Glu Gln Ala Phe Gln Gly Asp Glu Ser Val Arg Ile Asp
    3890                3895                3900

Ala Met Asp Val His Val Lys Ala Gly Arg Val Tyr Trp Thr Asn
    3905                3910                3915

Trp His Thr Gly Thr Ile Ser Tyr Arg Ser Leu Pro Pro Ala Ala
    3920                3925                3930

Pro Pro Thr Thr Ser Asn Arg His Arg Arg Gln Ile Asp Arg Gly
    3935                3940                3945

Val Thr His Leu Asn Ile Ser Gly Leu Lys Met Pro Arg Gly Ile
    3950                3955                3960

Ala Ile Asp Trp Val Ala Gly Asn Val Tyr Trp Thr Asp Ser Gly
    3965                3970                3975

Arg Asp Val Ile Glu Val Ala Gln Met Lys Gly Glu Asn Arg Lys
    3980                3985                3990

Thr Leu Ile Ser Gly Met Ile Asp Glu Pro His Ala Ile Val Val
    3995                4000                4005

Asp Pro Leu Arg Gly Thr Met Tyr Trp Ser Asp Trp Gly Asn His
    4010                4015                4020

Pro Lys Ile Glu Thr Ala Ala Met Asp Gly Thr Leu Arg Glu Thr
    4025                4030                4035

Leu Val Gln Asp Asn Ile Gln Trp Pro Thr Gly Leu Ala Val Asp
    4040                4045                4050

Tyr His Asn Glu Arg Leu Tyr Trp Ala Asp Ala Lys Leu Ser Val
    4055                4060                4065

Ile Gly Ser Ile Arg Leu Asn Gly Thr Asp Pro Ile Val Ala Ala
    4070                4075                4080

Asp Ser Lys Arg Gly Leu Ser His Pro Phe Ser Ile Asp Val Phe
    4085                4090                4095
```

```
Glu Asp  Tyr Ile Tyr Gly Val  Thr Tyr Ile Asn Asn  Arg Val Phe
    4100                 4105                 4110

Lys Ile  His Lys Phe Gly His  Ser Pro Leu Val Asn  Leu Thr Gly
    4115                 4120                 4125

Gly Leu  Ser His Ala Ser Asp  Val Val Leu Tyr His  Gln His Lys
    4130                 4135                 4140

Gln Pro  Glu Val Thr Asn Pro  Cys Asp Arg Lys Lys  Cys Glu Trp
    4145                 4150                 4155

Leu Cys  Leu Leu Ser Pro Ser  Gly Pro Val Cys Thr  Cys Pro Asn
    4160                 4165                 4170

Gly Lys  Arg Leu Asp Asn Gly  Thr Cys Val Pro Val  Pro Ser Pro
    4175                 4180                 4185

Thr Pro  Pro Pro Asp Ala Pro  Arg Pro Gly Thr Cys  Asn Leu Gln
    4190                 4195                 4200

Cys Phe  Asn Gly Gly Ser Cys  Phe Leu Asn Ala Arg  Arg Gln Pro
    4205                 4210                 4215

Lys Cys  Arg Cys Gln Pro Arg  Tyr Thr Gly Asp Lys  Cys Glu Leu
    4220                 4225                 4230

Asp Gln  Cys Trp Glu His Cys  Arg Asn Gly Gly Thr  Cys Ala Ala
    4235                 4240                 4245

Ser Pro  Ser Gly Met Pro Thr  Cys Arg Cys Pro Thr  Gly Phe Thr
    4250                 4255                 4260

Gly Pro  Lys Cys Thr Gln Gln  Val Cys Ala Gly Tyr  Cys Ala Asn
    4265                 4270                 4275

Asn Ser  Thr Cys Thr Val Asn  Gln Gly Asn Gln Pro  Gln Cys Arg
    4280                 4285                 4290

Cys Leu  Pro Gly Phe Leu Gly  Asp Arg Cys Gln Tyr  Arg Gln Cys
    4295                 4300                 4305

Ser Gly  Tyr Cys Glu Asn Phe  Gly Thr Cys Gln Met  Ala Ala Asp
    4310                 4315                 4320

Gly Ser  Arg Gln Cys Arg Cys  Thr Ala Tyr Phe Glu  Gly Ser Arg
    4325                 4330                 4335

Cys Glu  Val Asn Lys Cys Ser  Arg Cys Leu Glu Gly  Ala Cys Val
    4340                 4345                 4350

Val Asn  Lys Gln Ser Gly Asp  Val Thr Cys Asn Cys  Thr Asp Gly
    4355                 4360                 4365

Arg Val  Ala Pro Ser Cys Leu  Thr Cys Val Gly His  Cys Ser Asn
    4370                 4375                 4380

Gly Gly  Ser Cys Thr Met Asn  Ser Lys Met Met Pro  Glu Cys Gln
    4385                 4390                 4395

Cys Pro  Pro His Met Thr Gly  Pro Arg Cys Glu Glu  His Val Phe
    4400                 4405                 4410

Ser Gln  Gln Gln Pro Gly His  Ile Ala Ser Ile Leu  Ile Pro Leu
    4415                 4420                 4425

Leu Leu  Leu Leu Leu Leu Val  Leu Val Ala Gly Val  Val Phe Trp
    4430                 4435                 4440

Tyr Lys  Arg Arg Val Gln Gly  Ala Lys Gly Phe Gln  His Gln Arg
    4445                 4450                 4455

Met Thr  Asn Gly Ala Met Asn  Val Glu Ile Gly Asn  Pro Thr Tyr
    4460                 4465                 4470

Lys Met  Tyr Glu Gly Gly Glu  Pro Asp Asp Val Gly  Gly Leu Leu
    4475                 4480                 4485

Asp Ala  Asp Phe Ala Leu Asp  Pro Asp Lys Pro Thr  Asn Phe Thr
```

```
    4490                4495                4500

Asn Pro  Val Tyr Ala Thr Leu  Tyr Met Gly Gly His  Gly Ser Arg
    4505                4510                4515

His Ser  Leu Ala Ser Thr Asp  Glu Lys Arg Glu Leu  Leu Gly Arg
    4520                4525                4530

Gly Pro  Glu Asp Glu Ile Gly  Asp Pro Leu Ala
    4535                4540


<210> SEQ ID NO 3
<211> LENGTH: 89
<212> TYPE: PRT
<213> ORGANISM: Homo sapiens

<400> SEQUENCE: 3

Leu Leu Leu Leu Leu Pro Leu Leu Ser Ala Leu Val Ala Ala Ala Ile
1               5                   10                  15

Asp Ala Pro Lys Thr Cys Ser Pro Lys Gln Phe Ala Cys Arg Asp Gln
            20                  25                  30

Ile Thr Cys Ile Ser Lys Gly Trp Arg Cys Asp Gly Glu Arg Asp Cys
        35                  40                  45

Pro Asp Gly Ser Asp Glu Ala Pro Glu Ile Cys Pro Gln Ser Lys Ala
    50                  55                  60

Gln Arg Cys Gln Pro Asn Glu His Asn Cys Leu Gly Thr Glu Leu Cys
65                  70                  75                  80

Val Pro Met Ser Arg Leu Cys Asn Gly
                85


<210> SEQ ID NO 4
<211> LENGTH: 378
<212> TYPE: PRT
<213> ORGANISM: Homo sapiens

<400> SEQUENCE: 4

Pro Pro Ile Phe Glu Ile Arg Met Tyr Asp Ala Gln Gln Gln Gln Val
1               5                   10                  15

Gly Thr Asn Lys Cys Arg Val Asn Asn Gly Gly Cys Ser Ser Leu Cys
            20                  25                  30

Leu Ala Thr Pro Gly Ser Arg Gln Cys Ala Cys Ala Glu Asp Gln Val
        35                  40                  45

Leu Asp Ala Asp Gly Val Thr Cys Leu Ala Asn Pro Ser Tyr Val Pro
    50                  55                  60

Pro Pro Gln Cys Gln Pro Gly Glu Phe Ala Cys Ala Asn Ser Arg Cys
65                  70                  75                  80

Ile Gln Glu Arg Trp Lys Cys Asp Gly Asp Asn Asp Cys Leu Asp Asn
                85                  90                  95

Ser Asp Glu Ala Pro Ala Leu Cys His Gln His Thr Cys Pro Ser Asp
            100                 105                 110

Arg Phe Lys Cys Glu Asn Asn Arg Cys Ile Pro Asn Arg Trp Leu Cys
        115                 120                 125

Asp Gly Asp Asn Asp Cys Gly Asn Ser Glu Asp Glu Ser Asn Ala Thr
    130                 135                 140

Cys Ser Ala Arg Thr Cys Pro Pro Asn Gln Phe Ser Cys Ala Ser Gly
145                 150                 155                 160

Arg Cys Ile Pro Ile Ser Trp Thr Cys Asp Leu Asp Asp Asp Cys Gly
                165                 170                 175

Asp Arg Ser Asp Glu Ser Ala Ser Cys Ala Tyr Pro Thr Cys Phe Pro
```

```
            180                 185                 190

Leu Thr Gln Phe Thr Cys Asn Asn Gly Arg Cys Ile Asn Ile Asn Trp
        195                 200                 205

Arg Cys Asp Asn Asp Asn Asp Cys Gly Asp Asn Ser Asp Glu Ala Gly
    210                 215                 220

Cys Ser His Ser Cys Ser Ser Thr Gln Phe Lys Cys Asn Ser Gly Arg
225                 230                 235                 240

Cys Ile Pro Glu His Trp Thr Cys Asp Gly Asp Asn Asp Cys Gly Asp
                245                 250                 255

Tyr Ser Asp Glu Thr His Ala Asn Cys Thr Asn Gln Ala Thr Arg Pro
            260                 265                 270

Pro Gly Gly Cys His Thr Asp Glu Phe Gln Cys Arg Leu Asp Gly Leu
        275                 280                 285

Cys Ile Pro Leu Arg Trp Arg Cys Asp Gly Asp Thr Asp Cys Met Asp
    290                 295                 300

Ser Ser Asp Glu Lys Ser Cys Glu Gly Val Thr His Val Cys Asp Pro
305                 310                 315                 320

Ser Val Lys Phe Gly Cys Lys Asp Ser Ala Arg Cys Ile Ser Lys Ala
                325                 330                 335

Trp Val Cys Asp Gly Asp Asn Asp Cys Glu Asp Asn Ser Asp Glu Glu
            340                 345                 350

Asn Cys Glu Ser Leu Ala Cys Arg Pro Pro Ser His Pro Cys Ala Asn
        355                 360                 365

Asn Thr Ser Val Cys Leu Pro Pro Asp Lys
    370                 375


<210> SEQ ID NO 5
<211> LENGTH: 382
<212> TYPE: PRT
<213> ORGANISM: Homo sapiens

<400> SEQUENCE: 5

Thr Asn Lys Cys Arg Val Asn Asn Gly Gly Cys Ser Ser Leu Cys Leu
1               5                   10                  15

Ala Thr Pro Gly Ser Arg Gln Cys Ala Cys Ala Glu Asp Gln Val Leu
            20                  25                  30

Asp Ala Asp Gly Val Thr Cys Leu Ala Asn Pro Ser Tyr Val Pro Pro
        35                  40                  45

Pro Gln Cys Gln Pro Gly Glu Phe Ala Cys Ala Asn Ser Arg Cys Ile
    50                  55                  60

Gln Glu Arg Trp Lys Cys Asp Gly Asp Asn Asp Cys Leu Asp Asn Ser
65                  70                  75                  80

Asp Glu Ala Pro Ala Leu Cys His Gln His Thr Cys Pro Ser Asp Arg
                85                  90                  95

Phe Lys Cys Glu Asn Asn Arg Cys Ile Pro Asn Arg Trp Leu Cys Asp
            100                 105                 110

Gly Asp Asn Asp Cys Gly Asn Ser Glu Asp Glu Ser Asn Ala Thr Cys
        115                 120                 125

Ser Ala Arg Thr Cys Pro Pro Asn Gln Phe Ser Cys Ala Ser Gly Arg
    130                 135                 140

Cys Ile Pro Ile Ser Trp Thr Cys Asp Leu Asp Asp Asp Cys Gly Asp
145                 150                 155                 160

Arg Ser Asp Glu Ser Ala Ser Cys Ala Tyr Pro Thr Cys Phe Pro Leu
                165                 170                 175
```

```
Thr Gln Phe Thr Cys Asn Asn Gly Arg Cys Ile Asn Ile Asn Trp Arg
            180                 185                 190

Cys Asp Asn Asp Asn Asp Cys Gly Asp Asn Ser Asp Glu Ala Gly Cys
        195                 200                 205

Ser His Ser Cys Ser Ser Thr Gln Phe Lys Cys Asn Ser Gly Arg Cys
    210                 215                 220

Ile Pro Glu His Trp Thr Cys Asp Gly Asp Asn Asp Cys Gly Asp Tyr
225                 230                 235                 240

Ser Asp Glu Thr His Ala Asn Cys Thr Asn Gln Ala Thr Arg Pro Pro
                245                 250                 255

Gly Gly Cys His Thr Asp Glu Phe Gln Cys Arg Leu Asp Gly Leu Cys
            260                 265                 270

Ile Pro Leu Arg Trp Arg Cys Asp Gly Asp Thr Asp Cys Met Asp Ser
        275                 280                 285

Ser Asp Glu Lys Ser Cys Glu Gly Val Thr His Val Cys Asp Pro Ser
    290                 295                 300

Val Lys Phe Gly Cys Lys Asp Ser Ala Arg Cys Ile Ser Lys Ala Trp
305                 310                 315                 320

Val Cys Asp Gly Asp Asn Asp Cys Glu Asp Asn Ser Asp Glu Glu Asn
                325                 330                 335

Cys Glu Ser Leu Ala Cys Arg Pro Pro Ser His Pro Cys Ala Asn Asn
            340                 345                 350

Thr Ser Val Cys Leu Pro Pro Asp Lys Leu Cys Asp Gly Asn Asp Asp
        355                 360                 365

Cys Gly Asp Gly Ser Asp Glu Gly Glu Leu Cys Asp Gln Cys
    370                 375                 380


<210> SEQ ID NO 6
<211> LENGTH: 462
<212> TYPE: PRT
<213> ORGANISM: Homo sapiens

<400> SEQUENCE: 6

Gln Gln Pro Met Gly Ile Ile Ala Val Ala Asn Asp Thr Asn Ser Cys
1               5                   10                  15

Glu Leu Ser Pro Cys Arg Ile Asn Asn Gly Gly Cys Gln Asp Leu Cys
            20                  25                  30

Leu Leu Thr His Gln Gly His Val Asn Cys Ser Cys Arg Gly Gly Arg
        35                  40                  45

Ile Leu Gln Asp Asp Leu Thr Cys Arg Ala Val Asn Ser Ser Cys Arg
    50                  55                  60

Ala Gln Asp Glu Phe Glu Cys Ala Asn Gly Glu Cys Ile Asn Phe Ser
65                  70                  75                  80

Leu Thr Cys Asp Gly Val Pro His Cys Lys Asp Lys Ser Asp Glu Lys
                85                  90                  95

Pro Ser Tyr Cys Asn Ser Arg Arg Cys Lys Lys Thr Phe Arg Gln Cys
            100                 105                 110

Ser Asn Gly Arg Cys Val Ser Asn Met Leu Trp Cys Asn Gly Ala Asp
        115                 120                 125

Asp Cys Gly Asp Gly Ser Asp Glu Ile Pro Cys Asn Lys Thr Ala Cys
    130                 135                 140

Gly Val Gly Glu Phe Arg Cys Arg Asp Gly Thr Cys Ile Gly Asn Ser
145                 150                 155                 160

Ser Arg Cys Asn Gln Phe Val Asp Cys Glu Asp Ala Ser Asp Glu Met
                165                 170                 175
```

```
Asn Cys Ser Ala Thr Asp Cys Ser Ser Tyr Phe Arg Leu Gly Val Lys
            180                 185                 190

Gly Val Leu Phe Gln Pro Cys Glu Arg Thr Ser Leu Cys Tyr Ala Pro
        195                 200                 205

Ser Trp Val Cys Asp Gly Ala Asn Asp Cys Gly Asp Tyr Ser Asp Glu
    210                 215                 220

Arg Asp Cys Pro Gly Val Lys Arg Pro Arg Cys Pro Leu Asn Tyr Phe
225                 230                 235                 240

Ala Cys Pro Ser Gly Arg Cys Ile Pro Met Ser Trp Thr Cys Asp Lys
                245                 250                 255

Glu Asp Asp Cys Glu His Gly Glu Asp Glu Thr His Cys Asn Lys Phe
            260                 265                 270

Cys Ser Glu Ala Gln Phe Glu Cys Gln Asn His Arg Cys Ile Ser Lys
        275                 280                 285

Gln Trp Leu Cys Asp Gly Ser Asp Asp Cys Gly Asp Gly Ser Asp Glu
    290                 295                 300

Ala Ala His Cys Glu Gly Lys Thr Cys Gly Pro Ser Ser Phe Ser Cys
305                 310                 315                 320

Pro Gly Thr His Val Cys Val Pro Glu Arg Trp Leu Cys Asp Gly Asp
                325                 330                 335

Lys Asp Cys Ala Asp Gly Ala Asp Glu Ser Ile Ala Ala Gly Cys Leu
            340                 345                 350

Tyr Asn Ser Thr Cys Asp Asp Arg Glu Phe Met Cys Gln Asn Arg Gln
        355                 360                 365

Cys Ile Pro Lys His Phe Val Cys Asp His Asp Arg Asp Cys Ala Asp
    370                 375                 380

Gly Ser Asp Glu Ser Pro Glu Cys Glu Tyr Pro Thr Cys Gly Pro Ser
385                 390                 395                 400

Glu Phe Arg Cys Ala Asn Gly Arg Cys Leu Ser Ser Arg Gln Trp Glu
                405                 410                 415

Cys Asp Gly Glu Asn Asp Cys His Asp Gln Ser Asp Glu Ala Pro Lys
            420                 425                 430

Asn Pro His Cys Thr Ser Gln Glu His Lys Cys Asn Ala Ser Ser Gln
        435                 440                 445

Phe Leu Cys Ser Ser Gly Arg Cys Val Ala Glu Ala Leu Leu
    450                 455                 460
```

<210> SEQ ID NO 7
<211> LENGTH: 491
<212> TYPE: PRT
<213> ORGANISM: Homo sapiens

<400> SEQUENCE: 7

```
Arg Pro Met Asp Leu His Val Phe His Ala Leu Arg Gln Pro Asp Val
1               5                   10                  15

Pro Asn His Pro Cys Lys Val Asn Asn Gly Gly Cys Ser Asn Leu Cys
            20                  25                  30

Leu Leu Ser Pro Gly Gly Gly His Lys Cys Ala Cys Pro Thr Asn Phe
        35                  40                  45

Tyr Leu Gly Ser Asp Gly Arg Thr Cys Val Ser Asn Cys Thr Ala Ser
    50                  55                  60

Gln Phe Val Cys Lys Asn Asp Lys Cys Ile Pro Phe Trp Trp Lys Cys
65                  70                  75                  80

Asp Thr Glu Asp Asp Cys Gly Asp His Ser Asp Glu Pro Pro Asp Cys
```

```
                85                  90                  95

Pro Glu Phe Lys Cys Arg Pro Gly Gln Phe Gln Cys Ser Thr Gly Ile
            100                 105                 110

Cys Thr Asn Pro Ala Phe Ile Cys Asp Gly Asp Asn Asp Cys Gln Asp
        115                 120                 125

Asn Ser Asp Glu Ala Asn Cys Asp Ile His Val Cys Leu Pro Ser Gln
    130                 135                 140

Phe Lys Cys Thr Asn Thr Asn Arg Cys Ile Pro Gly Ile Phe Arg Cys
145                 150                 155                 160

Asn Gly Gln Asp Asn Cys Gly Asp Gly Glu Asp Glu Arg Asp Cys Pro
                165                 170                 175

Glu Val Thr Cys Ala Pro Asn Gln Phe Gln Cys Ser Ile Thr Lys Arg
            180                 185                 190

Cys Ile Pro Arg Val Trp Val Cys Asp Arg Asp Asn Asp Cys Val Asp
        195                 200                 205

Gly Ser Asp Glu Pro Ala Asn Cys Thr Gln Met Thr Cys Gly Val Asp
    210                 215                 220

Glu Phe Arg Cys Lys Asp Ser Gly Arg Cys Ile Pro Ala Arg Trp Lys
225                 230                 235                 240

Cys Asp Gly Glu Asp Asp Cys Gly Asp Gly Ser Asp Glu Pro Lys Glu
                245                 250                 255

Glu Cys Asp Glu Arg Thr Cys Glu Pro Tyr Gln Phe Arg Cys Lys Asn
            260                 265                 270

Asn Arg Cys Val Pro Gly Arg Trp Gln Cys Asp Tyr Asp Asn Asp Cys
        275                 280                 285

Gly Asp Asn Ser Asp Glu Glu Ser Cys Thr Pro Arg Pro Cys Ser Glu
    290                 295                 300

Ser Glu Phe Ser Cys Ala Asn Gly Arg Cys Ile Ala Gly Arg Trp Lys
305                 310                 315                 320

Cys Asp Gly Asp His Asp Cys Ala Asp Gly Ser Asp Glu Lys Asp Cys
                325                 330                 335

Thr Pro Arg Cys Asp Met Asp Gln Phe Gln Cys Lys Ser Gly His Cys
            340                 345                 350

Ile Pro Leu Arg Trp Arg Cys Asp Ala Asp Ala Asp Cys Met Asp Gly
        355                 360                 365

Ser Asp Glu Glu Ala Cys Gly Thr Gly Val Arg Thr Cys Pro Leu Asp
    370                 375                 380

Glu Phe Gln Cys Asn Asn Thr Leu Cys Lys Pro Leu Ala Trp Lys Cys
385                 390                 395                 400

Asp Gly Glu Asp Asp Cys Gly Asp Asn Ser Asp Glu Asn Pro Glu Glu
                405                 410                 415

Cys Ala Arg Phe Val Cys Pro Pro Asn Arg Pro Phe Arg Cys Lys Asn
            420                 425                 430

Asp Arg Val Cys Leu Trp Ile Gly Arg Gln Cys Asp Gly Thr Asp Asn
        435                 440                 445

Cys Gly Asp Gly Thr Asp Glu Glu Asp Cys Glu Pro Pro Thr Ala His
    450                 455                 460

Thr Thr His Cys Lys Asp Lys Lys Glu Phe Leu Cys Arg Asn Gln Arg
465                 470                 475                 480

Cys Leu Ser Ser Ser Leu Arg Cys Asn Met Phe
                485                 490
```

<210> SEQ ID NO 8

```
<211> LENGTH: 448
<212> TYPE: PRT
<213> ORGANISM: Homo sapiens

<400> SEQUENCE: 8

Val Ser Asn Cys Thr Ala Ser Gln Phe Val Cys Lys Asn Asp Lys Cys
1               5                   10                  15

Ile Pro Phe Trp Trp Lys Cys Asp Thr Glu Asp Asp Cys Gly Asp His
            20                  25                  30

Ser Asp Glu Pro Pro Asp Cys Pro Glu Phe Lys Cys Arg Pro Gly Gln
        35                  40                  45

Phe Gln Cys Ser Thr Gly Ile Cys Thr Asn Pro Ala Phe Ile Cys Asp
    50                  55                  60

Gly Asp Asn Asp Cys Gln Asp Asn Ser Asp Glu Ala Asn Cys Asp Ile
65                  70                  75                  80

His Val Cys Leu Pro Ser Gln Phe Lys Cys Thr Asn Thr Asn Arg Cys
                85                  90                  95

Ile Pro Gly Ile Phe Arg Cys Asn Gly Gln Asp Asn Cys Gly Asp Gly
            100                 105                 110

Glu Asp Glu Arg Asp Cys Pro Glu Val Thr Cys Ala Pro Asn Gln Phe
        115                 120                 125

Gln Cys Ser Ile Thr Lys Arg Cys Ile Pro Arg Val Trp Val Cys Asp
    130                 135                 140

Arg Asp Asn Asp Cys Val Asp Gly Ser Asp Glu Pro Ala Asn Cys Thr
145                 150                 155                 160

Gln Met Thr Cys Gly Val Asp Glu Phe Arg Cys Lys Asp Ser Gly Arg
                165                 170                 175

Cys Ile Pro Ala Arg Trp Lys Cys Asp Gly Glu Asp Asp Cys Gly Asp
            180                 185                 190

Gly Ser Asp Glu Pro Lys Glu Glu Cys Asp Glu Arg Thr Cys Glu Pro
        195                 200                 205

Tyr Gln Phe Arg Cys Lys Asn Asn Arg Cys Val Pro Gly Arg Trp Gln
    210                 215                 220

Cys Asp Tyr Asp Asn Asp Cys Gly Asp Asn Ser Asp Glu Glu Ser Cys
225                 230                 235                 240

Thr Pro Arg Pro Cys Ser Glu Ser Glu Phe Ser Cys Ala Asn Gly Arg
                245                 250                 255

Cys Ile Ala Gly Arg Trp Lys Cys Asp Gly Asp His Asp Cys Ala Asp
            260                 265                 270

Gly Ser Asp Glu Lys Asp Cys Thr Pro Arg Cys Asp Met Asp Gln Phe
        275                 280                 285

Gln Cys Lys Ser Gly His Cys Ile Pro Leu Arg Trp Arg Cys Asp Ala
    290                 295                 300

Asp Ala Asp Cys Met Asp Gly Ser Asp Glu Glu Ala Cys Gly Thr Gly
305                 310                 315                 320

Val Arg Thr Cys Pro Leu Asp Glu Phe Gln Cys Asn Asn Thr Leu Cys
                325                 330                 335

Lys Pro Leu Ala Trp Lys Cys Asp Gly Glu Asp Asp Cys Gly Asp Asn
            340                 345                 350

Ser Asp Glu Asn Pro Glu Glu Cys Ala Arg Phe Val Cys Pro Pro Asn
        355                 360                 365

Arg Pro Phe Arg Cys Lys Asn Asp Arg Val Cys Leu Trp Ile Gly Arg
    370                 375                 380

Gln Cys Asp Gly Thr Asp Asn Cys Gly Asp Gly Thr Asp Glu Glu Asp
```

```
385                 390                 395                 400

Cys Glu Pro Pro Thr Ala His Thr Thr His Cys Lys Asp Lys Lys Glu
                405                 410                 415

Phe Leu Cys Arg Asn Gln Arg Cys Leu Ser Ser Ser Leu Arg Cys Asn
            420                 425                 430

Met Phe Asp Asp Cys Gly Asp Gly Ser Asp Glu Glu Asp Cys Ser Ile
        435                 440                 445


<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9

cgagcgaccu ccuaucuuuu u                                               21


<210> SEQ ID NO 10
<211> LENGTH: 626
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ile Phe Leu Ala Thr Leu Pro Leu Phe Trp Ile Met Ile Ser Ala
1               5                   10                  15

Ser Arg Gly Gly His Trp Gly Ala Trp Met Pro Ser Thr Ile Ser Ala
            20                  25                  30

Phe Glu Gly Thr Cys Val Ser Ile Pro Cys Arg Phe Asp Phe Pro Asp
        35                  40                  45

Glu Leu Arg Pro Ala Val Val His Gly Val Trp Tyr Phe Asn Ser Pro
    50                  55                  60

Tyr Pro Lys Asn Tyr Pro Pro Val Val Phe Lys Ser Arg Thr Gln Val
65                  70                  75                  80

Val His Glu Ser Phe Gln Gly Arg Ser Arg Leu Leu Gly Asp Leu Gly
                85                  90                  95

Leu Arg Asn Cys Thr Leu Leu Leu Ser Thr Leu Ser Pro Glu Leu Gly
            100                 105                 110

Gly Lys Tyr Tyr Phe Arg Gly Asp Leu Gly Gly Tyr Asn Gln Tyr Thr
        115                 120                 125

Phe Ser Glu His Ser Val Leu Asp Ile Val Asn Thr Pro Asn Ile Val
    130                 135                 140

Val Pro Pro Glu Val Val Ala Gly Thr Glu Val Glu Val Ser Cys Met
145                 150                 155                 160

Val Pro Asp Asn Cys Pro Glu Leu Arg Pro Glu Leu Ser Trp Leu Gly
                165                 170                 175

His Glu Gly Leu Gly Glu Pro Thr Val Leu Gly Arg Leu Arg Glu Asp
            180                 185                 190

Glu Gly Thr Trp Val Gln Val Ser Leu Leu His Phe Val Pro Thr Arg
        195                 200                 205

Glu Ala Asn Gly His Arg Leu Gly Cys Gln Ala Ala Phe Pro Asn Thr
    210                 215                 220

Thr Leu Gln Phe Glu Gly Tyr Ala Ser Leu Asp Val Lys Tyr Pro Pro
225                 230                 235                 240
```

-continued

```
Val Ile Val Glu Met Asn Ser Ser Val Glu Ala Ile Glu Gly Ser His
                245                 250                 255

Val Ser Leu Leu Cys Gly Ala Asp Ser Asn Pro Pro Pro Leu Leu Thr
            260                 265                 270

Trp Met Arg Asp Gly Met Val Leu Arg Glu Ala Val Ala Lys Ser Leu
        275                 280                 285

Tyr Leu Asp Leu Glu Glu Val Thr Pro Gly Glu Asp Gly Val Tyr Ala
    290                 295                 300

Cys Leu Ala Glu Asn Ala Tyr Gly Gln Asp Asn Arg Thr Val Glu Leu
305                 310                 315                 320

Ser Val Met Tyr Ala Pro Trp Lys Pro Thr Val Asn Gly Thr Val Val
                325                 330                 335

Ala Val Glu Gly Glu Thr Val Ser Ile Leu Cys Ser Thr Gln Ser Asn
            340                 345                 350

Pro Asp Pro Ile Leu Thr Ile Phe Lys Glu Lys Gln Ile Leu Ala Thr
        355                 360                 365

Val Ile Tyr Glu Ser Gln Leu Gln Leu Glu Leu Pro Ala Val Thr Pro
    370                 375                 380

Glu Asp Asp Gly Glu Tyr Trp Cys Val Ala Glu Asn Gln Tyr Gly Gln
385                 390                 395                 400

Arg Ala Thr Ala Phe Asn Leu Ser Val Glu Phe Ala Pro Ile Ile Leu
                405                 410                 415

Leu Glu Ser His Cys Ala Ala Ala Arg Asp Thr Val Gln Cys Leu Cys
            420                 425                 430

Val Val Lys Ser Asn Pro Glu Pro Ser Val Ala Phe Glu Leu Pro Ser
        435                 440                 445

Arg Asn Val Thr Val Asn Glu Thr Glu Arg Glu Phe Val Tyr Ser Glu
    450                 455                 460

Arg Ser Gly Leu Leu Leu Thr Ser Ile Leu Thr Ile Arg Gly Gln Ala
465                 470                 475                 480

Gln Ala Pro Pro Arg Val Ile Cys Thr Ser Arg Asn Leu Tyr Gly Thr
                485                 490                 495

Gln Ser Leu Glu Leu Pro Phe Gln Gly Ala His Arg Leu Met Trp Ala
            500                 505                 510

Lys Ile Gly Pro Val Gly Ala Val Val Ala Phe Ala Ile Leu Ile Ala
        515                 520                 525

Ile Val Cys Tyr Ile Thr Gln Thr Arg Arg Lys Lys Asn Val Thr Glu
    530                 535                 540

Ser Ser Ser Phe Ser Gly Gly Asp Asn Pro His Val Leu Tyr Ser Pro
545                 550                 555                 560

Glu Phe Arg Ile Ser Gly Ala Pro Asp Lys Tyr Glu Ser Glu Lys Arg
                565                 570                 575

Leu Gly Ser Glu Arg Arg Leu Leu Gly Leu Arg Gly Glu Ser Pro Glu
            580                 585                 590

Leu Asp Leu Ser Tyr Ser His Ser Asp Leu Gly Lys Arg Pro Thr Lys
        595                 600                 605

Asp Ser Tyr Thr Leu Thr Glu Glu Leu Ala Glu Tyr Ala Glu Ile Arg
    610                 615                 620

Val Lys
625
```